United States Patent
Reboud-Ravaux et al.

(10) Patent No.: US 9,532,973 B2
(45) Date of Patent: *Jan. 3, 2017

(54) USE OF COUMARIN DERIVATIVES FOR THE PREPARATION OF DRUGS FOR TREATING SKIN DISEASES

(71) Applicants: UNIVERSITE PIERRE ET MARIE CURIE (PARIS 6), Paris (FR); UNIVERSITE DE LIEGE, Angleur (BE); Karla Hadot, Limours (FR); Adrien Pagano, Limours (FR)

(72) Inventors: Michele Reboud-Ravaux, Paris (FR); Chahrazade Yerroum-El Amri, Ermont (FR); Xiao Tan, Villejuif (FR); Lixian Qin, Paris (FR); Maurice Pagano, Limours (FR); Alain Hovnanian, Vincennes (FR); Laetitia Furio, Montrouge (FR); Bernard Pirotte, Oupeye (BE)

(73) Assignees: UNIVERSITE PIERRE ET MARIE CURIE (PARIS 6), Paris (FR); UNIVERSITE DE LIEGE, Angleur (BE)

( * ) Notice: Subject to any disclaimer, the term of this patent is extended or adjusted under 35 U.S.C. 154(b) by 0 days.

This patent is subject to a terminal disclaimer.

(21) Appl. No.: 14/643,442

(22) Filed: Mar. 10, 2015

(65) Prior Publication Data
US 2015/0182499 A1     Jul. 2, 2015

Related U.S. Application Data

(60) Division of application No. 14/155,633, filed on Jan. 15, 2014, now Pat. No. 9,006,466, which is a continuation-in-part of application No. PCT/EP2012/063851, filed on Jul. 13, 2012.

(30) Foreign Application Priority Data

Jul. 15, 2011   (EP) .................................... 11305931

(51) Int. Cl.
| | |
|---|---|
| *C07D 311/02* | (2006.01) |
| *A61K 31/37* | (2006.01) |
| *C07D 311/14* | (2006.01) |
| *C07D 405/12* | (2006.01) |
| *C07D 311/12* | (2006.01) |
| *A61K 31/4433* | (2006.01) |
| *A61K 31/4725* | (2006.01) |

(52) U.S. Cl.
CPC ........... *A61K 31/37* (2013.01); *A61K 31/4433* (2013.01); *A61K 31/4725* (2013.01); *C07D 311/12* (2013.01); *C07D 311/14* (2013.01); *C07D 405/12* (2013.01)

(58) Field of Classification Search
CPC .................................................. A61K 31/4433
See application file for complete search history.

(56) References Cited

U.S. PATENT DOCUMENTS 6,355,658 B1 * 3/2002 Reboud-Ravaux et al. .. 514/337

OTHER PUBLICATIONS

Tan et al. Journal of Medicinal Chemistry, 2015, 598-612.*
Pochet et al. Journal of Medicinal Chemistry (1996), 39(13), 2579-2585.

* cited by examiner

*Primary Examiner* — Nizal Chandrakumar
(74) *Attorney, Agent, or Firm* — Young & Thompson

(57) ABSTRACT

A compound of formula (I-1)

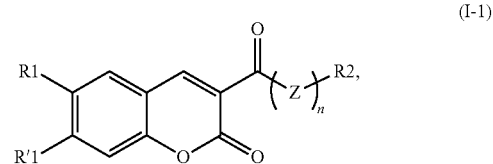

Figure 4:
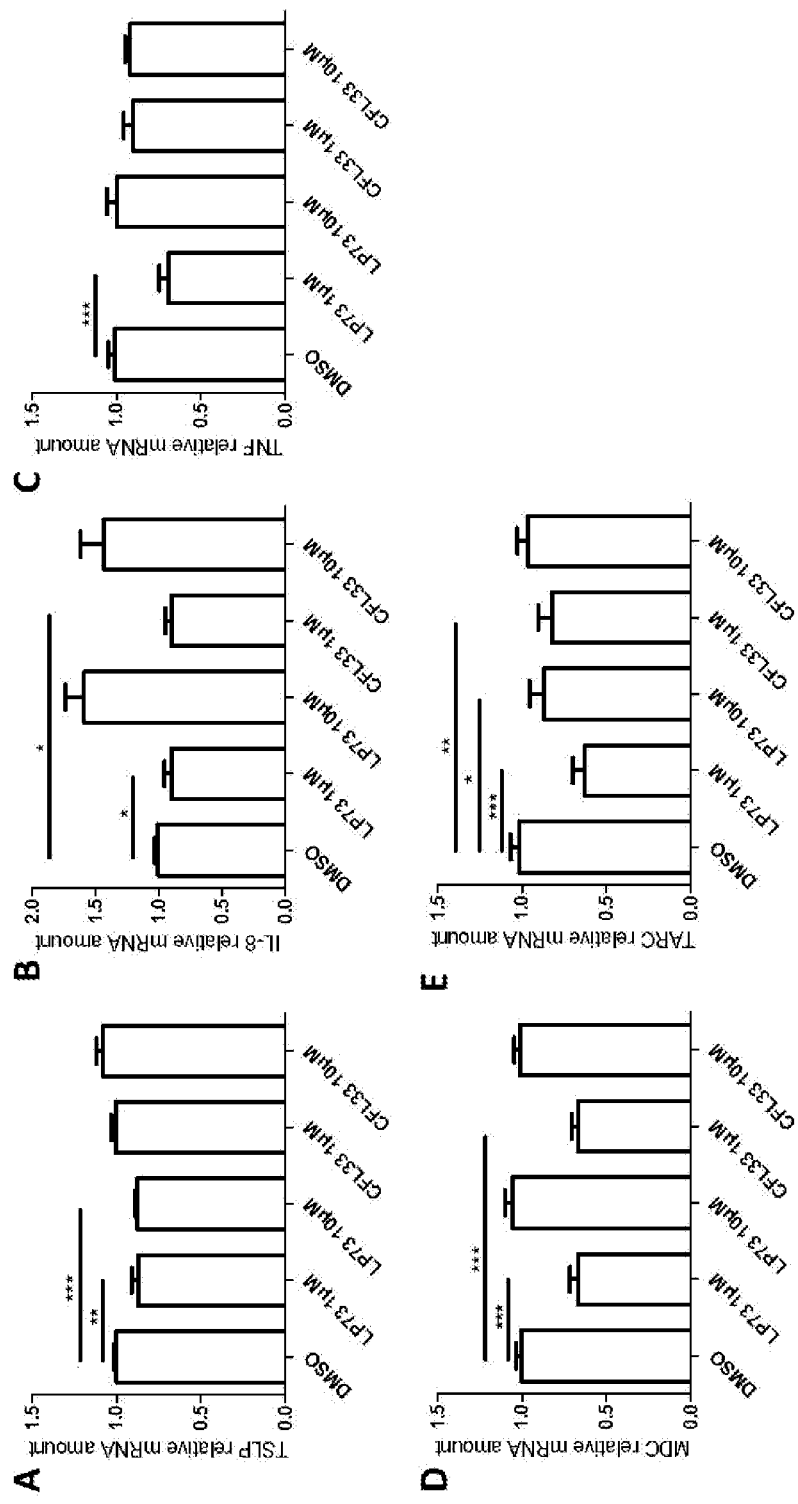

wherein n equals 0 or 1, Z represents O or S, R1 represents one group chosen among the group consisting of hydrogen, C1-C7 alkyl, substituted, or not, by a halogen, a hydroxyl or a —O—R12 group, wherein R12 is a C1-C7 alkyl, a group —CH$_2$—O—CO—R5 wherein R5 is chosen among a hydrogen atom and a C1-C7 alkyl, substituted or not by at least one halogen, a group —O—R13, wherein R13 is chosen among hydrogen and a C1-C7 alkyl, an amine or a —CH$_2$-amine, R'1 represents a group chosen among hydrogen and —O—R14, wherein R14 is chosen among hydrogen and a C1-C7 alkyl, and R2 is chosen among the group consisting of a C1-C7 alkyl, a C3-C6 cycloalkyl, an aryl group, and an heteroaryl group for the treatment of pathologies involving excess activity of at least one member of the kallikrein family.

4 Claims, 4 Drawing Sheets

Figure 1 : activation cascade involving kallikreins 5, 7 and 14.
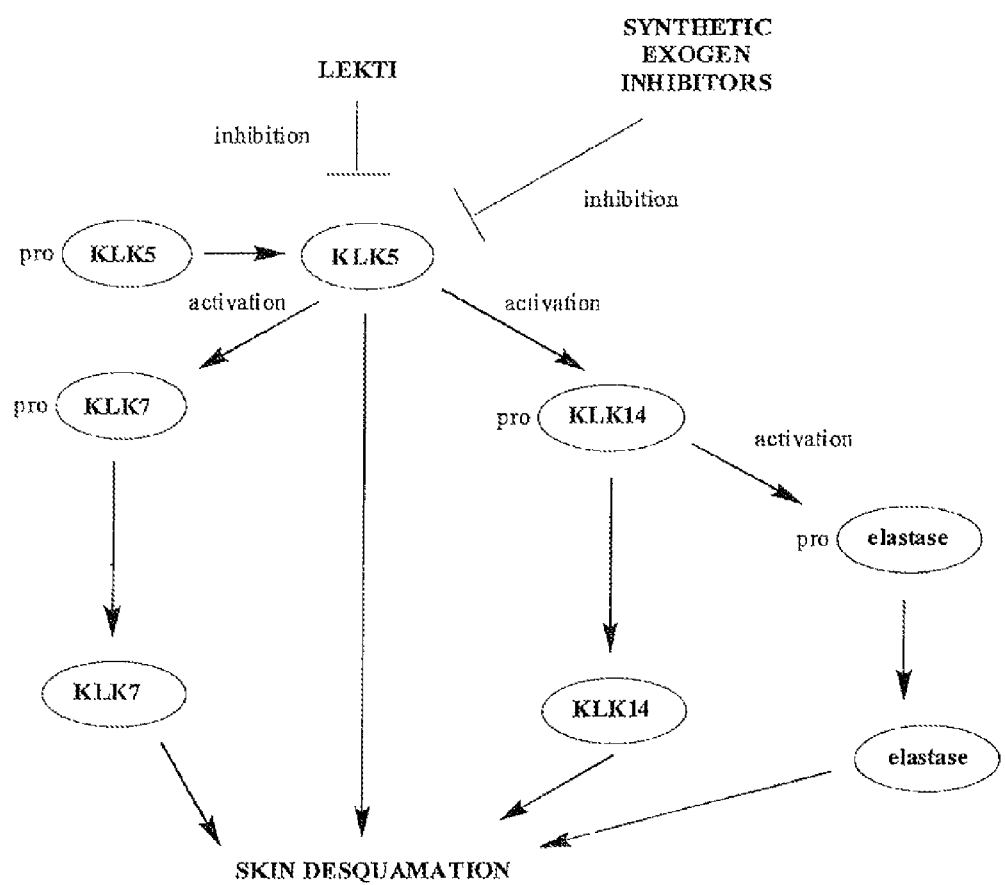

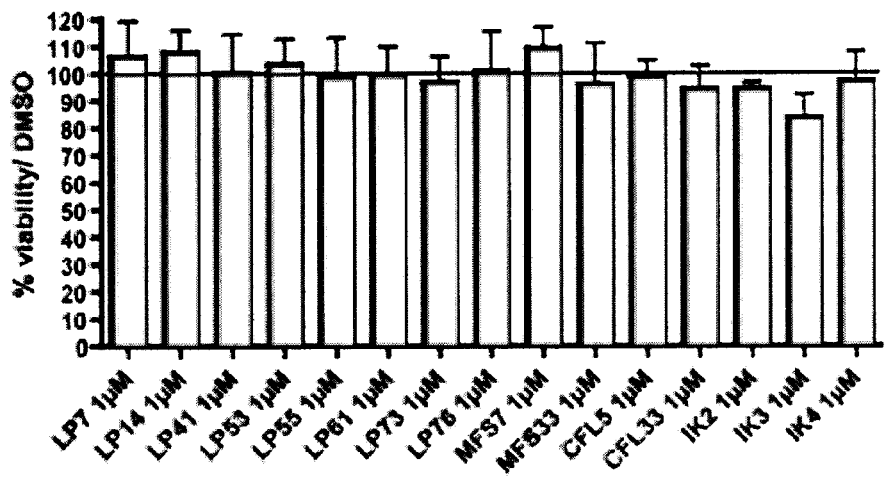
Figure 2 : mean cell viability after treatment +/- SD compared to mean viability of cells treated with the vehicle only (DMSO), at 1 µM
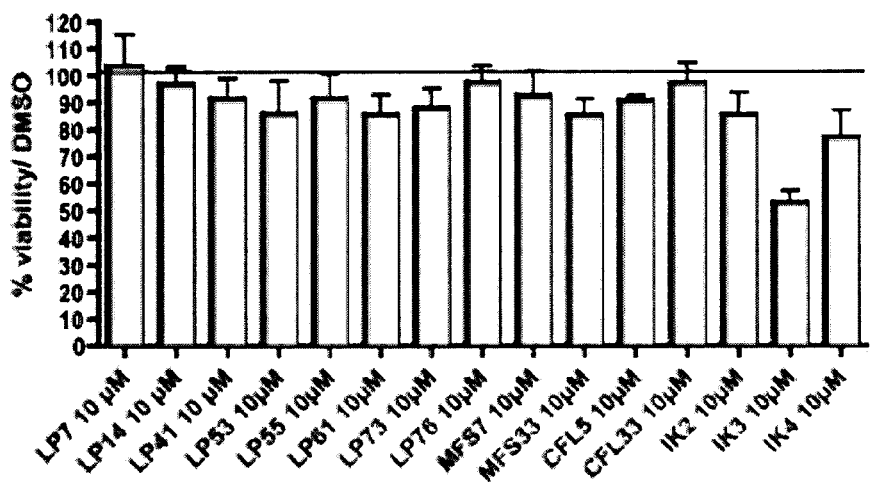
Figure 3 : mean cell viability after treatment +/- SD compared to mean viability of cells treated with the vehicle only (DMSO), at 10 µM

USE OF COUMARIN DERIVATIVES FOR THE PREPARATION OF DRUGS FOR TREATING SKIN DISEASES

The invention relates to the use of coumarin derivatives for the preparation of drugs for treating skin diseases.

Coumarin is a benzopyran found in many plants. It was first synthesized by William H. Perkin in 1868 (W. H. Perkin, *J. Chem. Soc.* 1868, 21, p 53) and its first use in perfumes since 1882 is due to its sweet odor, readily recognised as the scent of sweet grass and sweet clover. In the pharmaceutical industry, coumarin and other benzopyrans have numerous applications (Riveiro, M. E., De Kimpe, N., Moglioni A., Vasquez, R., Monczor, F., Shayo, C., Davio, C. *Curr. Med. Chem.*, 2010, 17(13), 1525-38; Wu, L., Wang, X., Xu, W., Farzaneh, F., Xu, R., *Curr. Med. Chem*, 2009, 16(32), 4236-60). For example, some derivatives are known as antitumoral compounds (Liu, X. H., Liu, H. F., Chen, J., Yang, Y., Song, B. A., Bai, L. S., Liu, J. X., Zhu, H. L., and Qi, X. B., *Bioorg Med Chem Lett*, 2010, 20, 5705-5708; Maresca, A., Temperini, C., Vu, H., Pham, N. B., Poulsen, S. A., Scozzafava, A., Quinn, R. J., and Supuran, C. T., *J Am Chem Soc*, 2009, 131, 3057-3062; Maresca, A., and Supuran, C. T. *Bioorg Med Chem Lett*, 2010, 20, 4511-4514; Starčević S, Kocbek P, Hribar G, Lanišnik Rižner T, Gobec S. Chem Biol Interac. 2011, 191(1-3):60-5, as neuroprotector compounds (Liu, W. B., Zhou, J., Qu, Y, Li, X., Lu, C. T., Xie, K. L., Sun, X. L., and Fei, Z., *Neurochem Int*, 2010, 57, 206-215), as antibacterial compounds (Parvez, A., Meshram, J., Tiwari, V., Sheik, J., Dongre, R., Youssoufi, M. H., and Ben Hadda, T. *Eur J Med Chem*, 2010, 45, 4370-4378), as anti-Alzheimer compounds (Pisani, L., Catto, M., Giangreco, I., Leonetti, F., Nicolotti, O., Stefanachi, A., Cellamare, S., and Carotti, A., *Chem Med Chem*, 2010, 5, 1616-1630; Fallarero, A., Oinonen, P., Gupta, S., Blom, P., Galkin, A., Mohan, C. G, and Vuorela, P. M., *Pharmacol Res*, 2008, 58, 215-221; Shelton, C. C., Zhu, L., Chau, D., Yang, L., Wang, R., Djaballah, H., Zheng, H., and Li, Y. M. *Proc Natl Acad Sci USA*, 2009, 106, 20228-20233), anti-VIH compounds (Huang, L., Yuan, X., Yu, D., Lee, K. H., and Chen, C. H., *Virology*, 2005, 332, 623-628.; Yu, D., Suzuki, M., Xie, L., Morris-Natschke, S. L., and Lee, K. H. *Med Res Rev*, 2003, 23, 322-345).

Coumarin derivative compounds are already known as serine protease inhibitors (WO9855472; Pochet L., Doucet C., Schynts M., Thierry N., Boggetto N., Pirotte B., Jiang K. I., Masereel B., de Tullio P., Delarge J., Reboud-Ravaux M., *J. Med. Chem*, 1996, 39, 2579-2585; Doucet C., Pochet L., Thierry N., Pirotte B., Delarge J., Reboud-Ravaux M., *J. Med. Chem.*, 1999, 42, 4161-4171).

Some of the compounds used in this patent definitively inactivate the α-chymotrypsin whereas human leukocyte elastase and human thrombin are temporarily inactivated.

Among the skin pathologies, Netherton syndrome (Comel C., <<Ichtyosis linearis circumflexa, *Dermatologica*, 1949, 98, 133-136; Netherton E. W., <<a unique case of trichorrexis invaginata>>, *Arch Dermatol*, 1958, 78, 483-487; Hovnanian A. et al, *Mol Biol Cell*, 2007, 18, 3607-3619; Hovnanian A. et al, *Nat Med*, 2007, 13, 975-80; Hovnanian A. et al, *Nat Genet*, 2005, 37, 56-65; Hovnanian A. et al, *Nat Genet*, 2000, 25, 141-142; Hovnanian A. et al, *J. Clin. Invest*, 2010, 120871-120882), is an inherited disease caused by a genetic abnormality in one chromosome. It entails abnormal skin desquamation and inflammatory phenomenons. Babies born with the syndrome have red and scaly skin, which can easily get infected, and they fail to thrive in their first years of life. They also have abnormal 'bamboo-type' hair. Netherton syndrome is a long-term debilitating and life-threatening condition because of the skin infections associated with the changes of the physical appearance of the patients and effects on the patients' mental state.

At the time of designation, Netherton syndrome affected approximately 0.05 in 10,000 people in the European Union.

There is no known cure at the moment for the Netherton syndrome, only several things can be done such as relieving the symptoms. Moisturising products are very helpful to minimise the scaling/cracking and anti-infective treatments are useful when appropriate because the skin is very susceptible to infection. Steroids can also be used.

This skin pathology may appear if the endogenous protein inhibitor LEKTI (lympho-epithelial Kazal type inhibitor) which controls the activity of a specific kind of serine protease belonging to the kallikrein family, is not active (Chavanas S., Bodemer C., Rochat A., Hamel-Teillac D., Ali M., Irvine A. D., *Nat Genet* 2000, 25, 141-142; Deraison C., Bonnart C., Lopez E, Besson C., Robinson R., Jayakumar A., *Mol Biol Cell*, 2007, 18, 3607-3619).

One of the aim of the invention is to provide coumarin derivatives able to treat skin diseases, in particular orphan skin diseases.

One of the aim of the invention is to provide pharmaceutical compositions for the treatment of pathologies involving an excess of activity of at least one member of the kallikrein family, in particular kallikrein-5 (KLK5), kallikrein-7 (KLK7) or kallikrein-14 (KLK14).

Another aim of the invention is to provide prevention or treatment of skin pathologies consisting of Netherton syndrome and atopic dermatitis, eczema, peeling skin syndrome, psoriasis, in particular Netherton syndrome.

Thus, the present invention relates to compounds of formula (I) as presented below:

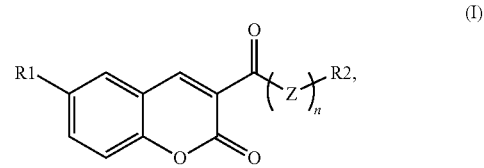

wherein n equals 0 or 1,
and wherein
if n=1, Z represents O or S,
R1 represents at least one group chosen among the group consisting of:
hydrogen
a linear or branched, saturated or not, C1-C7 alkyl, preferably a methyl group, substituted, or not, by a halogen chosen among Cl, F, I and Br,
a group —CH$_2$—O—CO—R5, wherein R5 is chosen among a hydrogen atom, and a linear or branched, saturated or not, C1-C7 alkyl, substituted or not by at least one halogen chosen among Cl, F, I and Br, and
an amine

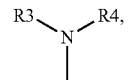

or a salt thereof, wherein R3 and R4, independently from each other, are chosen among hydrogen and a linear or branched, saturated or not, C1-C5 alkyl, and
R2 is chosen among the group consisting of:
- a linear or branched, saturated or not, C1-C7 alkyl, preferably a C1-C3 alkyl,
- a C3-C6 cycloalkyl, preferably a C4-C6 cycloalkyl, more preferably a cyclohexyl,
- an aryl group, preferably a phenyl group, possibly mono or polysubstituted, in particular disubstituted, by
  - a halogen chosen among Cl, F, I and Br, or
  - a linear or branched, saturated or not, C1-C7 alkyl, or
  - a group —CO—R6, R6 being chosen among the group consisting of: —OH, —NH$_2$, or salt thereof, and —O—R7, R7 being a linear or branched, saturated or not, C1-C7 alkyl, or
  - a group —O—R8, R8 being a linear or branched, saturated or not, C1-C7 alkyl, or
  - a group —NO$_2$,
  - a combination of the above,
and
- an heteroaryl group, preferably a pyridyl or an isoquinolinyl, possibly mono or polysubstituted, in particular disubstituted, by
  - a halogen chosen among Cl, F, I and Br, or
  - a linear or branched, saturated or not, C1-C7 alkyl, or
  - a group —CO—R6, R6 being chosen among the group consisting of: —OH, —NH$_2$, or salt thereof, and —O—R7, R7 being a linear or branched, saturated or not, C1-C7 alkyl, or
  - a group —O—R8, R8 being a linear or branched, saturated or not, C1-C7 alkyl, or
  - a combination of the above, provided that
when n=0, then R1 can only represent a linear or branched, saturated or not, C1-C7 alkyl, preferably a methyl group, possibly substituted by an halogen, such that
  if R1=CH$_3$ or CH$_2$—X, wherein X is an halogen, then R2 is a methyl group or a cycloalkyl group, preferably a cyclohexyl group,
when n=1,
  if R1=H, then R2 can only represent an isoquinolinyl or a phenyl substituted by two halogens, and
  if R1≠H, then if R2 is an aryl or an hetero aryl substituted by one linear or branched, saturated or not, C1-C7 alkyl, said aryl or heteroaryl is also substituted by at least another group, which is different from a C1-C7 alkyl,
for its use for the treatment of pathologies involving an excess of activity of at least one member of the kallikrein family, preferably belonging to the group consisting of KLK5, KLK7 and KLK14.

By the expression "if R1≠H, then if R2 is an aryl or an hetero aryl substituted by one linear or branched, saturated or not, C1-C7 alkyl, said aryl or heteroaryl is also substituted by at least another group different from a C1-C7 alkyl" is meant that if n=1, and if R1 is different from hydrogen and if R2 is an aryl or an hetero aryl substituted by one linear or branched, saturated or not, C1-C7 alkyl, then R2 has to be substituted by at least another group different from a C1-C7 alkyl.

The kallikreins were first named by E. Werle who reported in 1934 finding a substance in the pancreas of men and various animals in such great amounts that the pancreas could be taken for its site of origin. He named it kallikrein, by derivation from the Greek word for pancreas. It is clear that the fifteen known kallikreins are serine proteases with sufficient structural and functional similarities to be classified as a family.

Among the different members of this family of serine proteases, the focus is on kallikreins named KLK5, KLK7, KLK14, which are involved in skin desquamation and inflammatory phenomenons.

The present invention also relates to compounds of formula (I) as presented below:

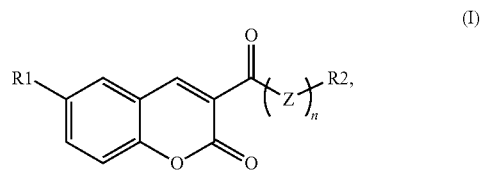

wherein n equals 0 or 1,
and wherein
  if n=1, Z represents O or S,
  R1 represents at least one group chosen among the group consisting of:
    hydrogen
    a linear or branched, saturated or not, C1-C7 alkyl, preferably a methyl group, substituted, or not, by a halogen chosen among Cl, F, I and Br,
    a group —CH$_2$—O—CO—R5, wherein R5 is chosen among a hydrogen atom, and a linear or branched, saturated or not, C1-C7 alkyl, substituted or not by at least one halogen chosen among Cl, F, I and Br, and
    an amine

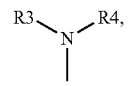

or a salt thereof, wherein R3 and R4, independently from each other, are chosen among hydrogen and a linear or branched, saturated or not, C1-C5 alkyl,
and
R2 is chosen among the group consisting of:
- a linear or branched, saturated or not, C1-C7 alkyl, preferably a C1-C3 alkyl,
- a C3-C6 cycloalkyl, preferably a C4-C6 cycloalkyl, more preferably a cyclohexyl,
- an aryl group, preferably a phenyl or a naphthyl group, possibly mono or or polysubstituted, in particular disubstituted, by
  - a halogen chosen among Cl, F, I and Br, or
  - a linear or branched, saturated or not, C1-C7 alkyl, or
  - a group —CO—R6, R6 being chosen among the group consisting of: —OH, —NH$_2$, or salt thereof, and —O—R7, R7 being a linear or branched, saturated or not, C1-C7 alkyl, or
  - a group —O—R8, R8 being a linear or branched, saturated or not, C1-C7 alkyl, or
  - a group —NO$_2$,
  - a combination of the above,
and
- an heteroaryl group, preferably a pyridyl or an isoquinolinyl, possibly mono or polysubstituted, in particular disubstituted, by a halogen chosen among Cl, F, I and Br, or
a linear or branched, saturated or not, C1-C7 alkyl, or
a group —CO—R6, R6 being chosen among the group consisting of: —OH, —NH$_2$, or salt thereof, and —O—R7, R7 being a linear or branched, saturated or not, C1-C7 alkyl, or
a group —O—R8, R8 being a linear or branched, saturated or not, C1-C7 alkyl, or
a combination of the above,
provided that
when n=0, then R1 can only represent a linear or branched, saturated or not, C1-C7 alkyl, preferably a methyl group, possibly substituted by an halogen, such that
if R1=CH$_3$ or CH$_2$—X, wherein X is an halogen, then R2 is a methyl group or a cycloalkyl group, preferably a cyclohexyl group,
when n=1,
if R1=H, then R2 can only represent an isoquinolinyl or a naphthyl, or a phenyl substituted by two halogens, and
if R1≠H, then if R2 is an aryl different from a naphthyl, or an hetero aryl, substituted by one linear or branched, saturated or not, C1-C7 alkyl, said aryl or heteroaryl is also substituted by at least another group, which is different from a C1-C7 alkyl,
for its use for the treatment of pathologies involving an excess of activity of at least one member of the kallikrein family, preferably belonging to the group consisting of KLK5, KLK7 and KLK14.

The present invention also relates to compounds of formula (I-1) as presented below:

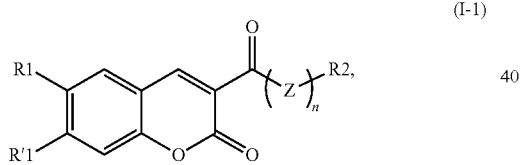

(I-1)

wherein n equals 0 or 1,
and wherein
if n=1, Z represents O or S,
R1 represents at least one group chosen among the group consisting of:
hydrogen
a linear or branched, saturated or not, C1-C7 alkyl, preferably a methyl group, substituted, or not, by a halogen chosen among Cl, F, I and Br,
a linear or branched, saturated or not, C1-C7 alkyl, preferably a methyl group, substituted by a hydroxyl or a —O—R12 group, wherein R12 is a linear or branched, saturated or not, C1-C7 alkyl, preferably a hydroxyl,
a group —CH$_2$—O—CO—R5, wherein R5 is chosen among a hydrogen atom, and a linear or branched, saturated or not, C1-C7 alkyl, substituted or not by at least one halogen chosen among Cl, F, I and Br,
a group —O—R13, wherein R13 is chosen among hydrogen and a linear or branched, saturated or not, C1-C7 alkyl, R13 being preferably a hydrogen,
an amine

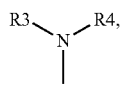

or a salt thereof, wherein R3 and R4, independently from each other, are chosen among hydrogen and a linear or branched, saturated or not, C1-C5 alkyl, and
a group

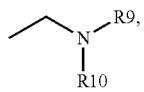

or a salt thereof, wherein R9 and R10, independently from each other, are chosen among:
hydrogen,
a linear or branched, saturated or not, C1-C5 alkyl,
—CO—R5, wherein R5 is chosen among a hydrogen atom, and a linear or branched, saturated or not, C1-C7 alkyl, substituted or not by at least one halogen chosen among Cl, F, I and Br,
—SO$_2$—R11, wherein R11 is a linear or branched, saturated or not, C1-C7 alkyl,
R'1 represents a group chosen among hydrogen and —O—R14, wherein R14 is chosen among hydrogen and a linear or branched, saturated or not, C1-C7 alkyl, R14 being preferably a hydrogen, R'1 being preferably a hydrogen, provided that R'1 represents hydrogen when R1 does not represent a —O—R13 group,
and
R2 is chosen among the group consisting of:
a linear or branched, saturated or not, C1-C7 alkyl, preferably a C1-C3 alkyl,
a C3-C6 cycloalkyl, preferably a C4-C6 cycloalkyl, more preferably a cyclohexyl,
an aryl group, preferably a phenyl group, possibly mono or polysubstituted, in particular disubstituted, by
a halogen chosen among Cl, F, I and Br, or
a linear or branched, saturated or not, C1-C7 alkyl, or
a group —CO—R6, R6 being chosen among the group consisting of: —OH, —NH$_2$, or salt thereof, and —O—R7, R7 being a linear or branched, saturated or not, C1-C7 alkyl, or
a group —O—R8, R8 being a linear or branched, saturated or not, C1-C7 alkyl, or
a group —NO$_2$,
a group —CN,
a combination of the above,
and
an heteroaryl group, preferably a pyridyl or an isoquinolinyl, possibly mono or polysubstituted, in particular disubstituted, by
a halogen chosen among Cl, F, I and Br, or
a linear or branched, saturated or not, C1-C7 alkyl, or
a group —CO—R6, R6 being chosen among the group consisting of: —OH, —NH$_2$, or salt thereof, and —O—R7, R7 being a linear or branched, saturated or not, C1-C7 alkyl, or
a group —O—R8, R8 being a linear or branched, saturated or not, C1-C7 alkyl, or
a combination of the above, provided that
when n=0, then R1 can only represent a linear or branched, saturated or not, C1-C7 alkyl, preferably a methyl group, possibly substituted by an halogen, such that
if R1=CH$_3$ or CH$_2$—X, wherein X is an halogen, then R2 is a methyl group or a cycloalkyl group, preferably a cyclohexyl group,
when n=1,
if R1=H, then R2 can only represent an isoquinolinyl or a phenyl substituted by two halogens, and
if R1≠H, then if R2 is an aryl or an hetero aryl substituted by one linear or branched, saturated or not, C1-C7 alkyl, said aryl or heteroaryl is also substituted by at least another group different from a C1-C7 alkyl,
for its use for the treatment of pathologies involving an excess of activity of at least one member of the kallikrein family, preferably belonging to the group consisting of KLK5, KLK7 and KLK14.

The present invention also relates to compounds of formula (I-1) as presented below:

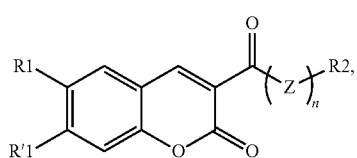
(I-1)

wherein n equals 0 or 1,
and wherein
if n=1, Z represents O or S,
R1 represents at least one group chosen among the group consisting of:
hydrogen
a linear or branched, saturated or not, C1-C7 alkyl, preferably a methyl group, substituted, or not, by a halogen chosen among Cl, F, I and Br,
a linear or branched, saturated or not, C1-C7 alkyl, preferably a methyl group, substituted by a hydroxyl or a —O—R12 group, wherein R12 is a linear or branched, saturated or not, C1-C7 alkyl, preferably a hydroxyl,
a group —CH$_2$—O—CO—R5, wherein R5 is chosen among a hydrogen atom, and a linear or branched, saturated or not, C1-C7 alkyl, substituted or not by at least one halogen chosen among Cl, F, I and Br,
a group —O—R13, wherein R13 is chosen among hydrogen and a linear or branched, saturated or not, C1-C7 alkyl, R13 being preferably a hydrogen,
an amine

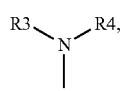

or a salt thereof, wherein R3 and R4, independently from each other, are chosen among hydrogen and a linear or branched, saturated or not, C1-C5 alkyl, and
a group

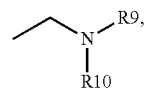

or a salt thereof, wherein R9 and R10, independently from each other, are chosen among:
hydrogen,
a linear or branched, saturated or not, C1-C5 alkyl,
—CO—R5, wherein R5 is chosen among a hydrogen atom, and a linear or branched, saturated or not, C1-C7 alkyl, substituted or not by at least one halogen chosen among Cl, F, I and Br,
—SO$_2$—R11, wherein R11 is a linear or branched, saturated or not, C1-C7 alkyl,
R'1 represents a group chosen among hydrogen and —O—R14, wherein R14 is chosen among hydrogen and a linear or branched, saturated or not, C1-C7 alkyl, R14 being preferably a hydrogen, R'1 being preferably a hydrogen, provided that R'1 represents hydrogen when R1 does not represent a —O—R13 group,
and
R2 is chosen among the group consisting of:
a linear or branched, saturated or not, C1-C7 alkyl, preferably a C1-C3 alkyl,
a C3-C6 cycloalkyl, preferably a C4-C6 cycloalkyl, more preferably a cyclohexyl,
an aryl group, preferably a phenyl or a naphthyl group, possibly mono or or polysubstituted, in particular disubstituted, by
a halogen chosen among Cl, F, I and Br, or
a linear or branched, saturated or not, C1-C7 alkyl, or
a group —CO—R6, R6 being chosen among the group consisting of: —OH, —NH$_2$, or salt thereof, and —O—R7, R7 being a linear or branched, saturated or not, C1-C7 alkyl, or
a group —O—R8, R8 being a linear or branched, saturated or not, C1-C7 alkyl, or
a group —NO$_2$,
a group —CN,
a combination of the above,
and
an heteroaryl group, preferably a pyridyl or an isoquinolinyl, possibly mono or polysubstituted, in particular disubstituted, by
a halogen chosen among Cl, F, I and Br, or
a linear or branched, saturated or not, C1-C7 alkyl, or
a group —CO—R6, R6 being chosen among the group consisting of: —OH, —NH$_2$, or salt thereof, and —O—R7, R7 being a linear or branched, saturated or not, C1-C7 alkyl, or
a group —O—R8, R8 being a linear or branched, saturated or not, C1-C7 alkyl, or
a combination of the above,
provided that
when n=0, then R1 can only represent a linear or branched, saturated or not, C1-C7 alkyl, preferably a methyl group, possibly substituted by an halogen, such that
if R1=CH$_3$ or CH$_2$—X, wherein X is an halogen, then R2 is a methyl group or a cycloalkyl group, preferably a cyclohexyl group, when n=1,
  if R1=H, then R2 can only represent an isoquinolinyl or a naphthyl, or a phenyl substituted by two halogens, and
  if R1≠H, then if R2 is an aryl different from a naphthyl, or an hetero aryl, substituted by one linear or branched, saturated or not, C1-C7 alkyl, said aryl or heteroaryl is also substituted by at least another group, which is different from a C1-C7 alkyl,
for its use for the treatment of pathologies involving an excess of activity of at least one member of the kallikrein family, preferably belonging to the group consisting of KLK5, KLK7 and KLK14.

According to another embodiment, the present invention relates to the above mentioned compounds wherein said pathologies are skin pathologies.

The use of the coumarin derivatives of the invention may be a way for treating skin pathologies involving an excess of activity of at least one member of the kallikrein family, belonging to the group consisting of KLK5, KLK7 and KLK14.

The activation cascade involving these kallikreins is represented in FIG. 1.

According to another embodiment, the present invention relates to the above mentioned compounds wherein said pathologies belong to the group consisting of Netherton syndrome, atopic dermatitis, psoriasis, eczema and peeling skin syndrome, preferably Netherton syndrome.

According to another embodiment, the present invention relates to the above mentioned compounds wherein said pathologies belong to the group consisting of Netherton syndrome, psoriasis, atopic eczema and allergic contact dermatitis, preferably Netherton syndrome.

Netherton syndrome, inherited skin disease, is caused by a genetic abnormality. The SPINK5 chromosome is responsible for LEKTI enzyme inhibitor (Chavanas S., Bodemer C., Rochat A., Hamel-Teillac D., Ali M., Irvine A. D., <<Mutations in SPINK5, encoding a serine protease inhibitor, cause Netherton syndrom>>, *Nat Genet* 2000, 25, 141-142; Magert H. J., Standker L., Kneutzmann P., "LEKTI, a novel 15-domain type of human serine proteinase inhibitor, *J Biol Chem*, 1999, 274, 21499-21502; Deraison C., Bonnart C., Lopez E, Besson C., Robinson R., Jayakumar A., <<LEKTI fragments specifically inhibit KLK5, KLK7 and KLK14 and control desquamation through a pH-dependent interaction>>, *Mol Biol Cell,* 2007, 18, 3607-3619).

According to another embodiment, the present invention relates to the above mentioned compounds wherein said at kallikrein family member protein is chosen among the group consisting of kallikrein-5, kallikrein-7 and kallikrein-14.

According to another embodiment, the present invention relates to the above mentioned compounds having the following formula (Ia):

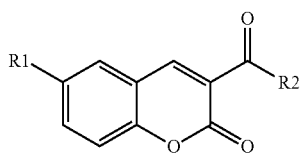

(Ia)

wherein
R1 represents a linear or branched, saturated or not, C1-C7 alkyl, preferably a methyl group, possibly substituted by a halogen, and R2 represents a methyl group, a cycloalkyl or an aryl group, preferably a cyclohexyl or a phenyl group.

According to another embodiment, the present invention relates to the above mentioned compound:

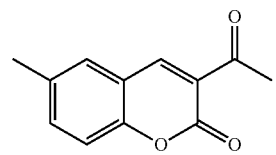

(D9)

In this case, in the general formula, n=0.

According to another embodiment, the present invention relates to the above mentioned compounds having the following formula (Ib):

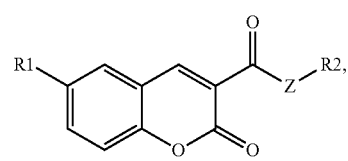

(Ib)

wherein
  Z represents O or S,
  R1 represents at least one group chosen among the group consisting of:
    a hydrogen
    a linear or branched, saturated or not, C1-C7 alkyl, preferably a methyl group, substituted, or not, by a halogen chosen among Cl, F, I and Br,
    a group —CH₂—O—CO—R5, wherein R5 is chosen among a hydrogen atom and a linear or branched, saturated or not, C1-C7 alkyl, substituted or not by at least one halogen chosen among Cl, F, I and Br, and
    an amine

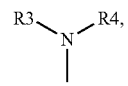

or a salt thereof, wherein R3 and R4, independently from each other, are chosen among hydrogen and a linear or branched, saturated or not, C1-05 alkyl,
  and
  R2 is chosen among the group consisting of:
    a linear or branched, saturated or not, C1-C7 alkyl, preferably a C1-C3 alkyl,
    a C3-C6 cycloalkyl, preferably a C4-C6 cycloalkyl, more preferably a cyclohexyl,
    an aryl group, preferably a phenyl group, possibly mono or polysubstituted, in particular disubstituted, by
      a halogen chosen among Cl, F, I and Br, or
      a linear or branched, saturated or not, C1-C7 alkyl, or
      a group —CO—R6, R6 being chosen among the group consisting of: —OH, —NH₂, or salt thereof, and —O—R7, R7 being a linear or branched, saturated or not, C1-C7 alkyl, or a group —O—R8, R8 being a linear or branched, saturated or not, C1-C7 alkyl, or
a group —NO$_2$,
a combination of the above,
and
an heteroaryl group, preferably a pyridyl or an isoquinolinyl, possibly mono or polysubstituted, in particular disubstituted, by
a halogen chosen among Cl, F, I and Br, or
a linear or branched, saturated or not, C1-C7 alkyl, or
a group —CO—R6, R6 being chosen among the group consisting of: —OH, —NH$_2$, or salt thereof, and —O—R7, R7 being a linear or branched, saturated or not, C1-C7 alkyl, or
a group —O—R8, R8 being a linear or branched, saturated or not, C1-C7 alkyl, or
a combination of the above,
provided that
if R1=H, then R2 can only represent an isoquinolinyl or a phenyl substituted by two halogens, and
if R1≠H, if R2 is an aryl or an hetero aryl substituted by one a linear or branched, saturated or not, C1-C7 alkyl, said aryl or heteroaryl is also substituted by at least another group different from a C1-C7 alkyl.

In this case, in the general formula, n=1, Z being oxygen or sulfur atom.

According to another embodiment, the present invention relates to the above mentioned compounds having the following formula (Ib):

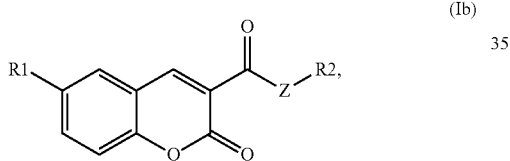

(Ib)

wherein
Z represents O or S,
R1 represents at least one group chosen among the group consisting of:
a hydrogen
a linear or branched, saturated or not, C1-C7 alkyl, preferably a methyl group, substituted, or not, by a halogen chosen among Cl, F, I and Br,
a group —CH$_2$—O—CO—R5, wherein R5 is chosen among a hydrogen atom and a linear or branched, saturated or not, C1-C7 alkyl, substituted or not by at least one halogen chosen among Cl, F, I and Br, and
an amine

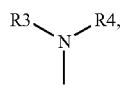

or a salt thereof, wherein R3 and R4, independently from each other, are chosen among hydrogen and a linear or branched, saturated or not, C1-C5 alkyl,
and
R2 is chosen among the group consisting of:
a linear or branched, saturated or not, C1-C7 alkyl, preferably a C1-C3 alkyl,
a C3-C6 cycloalkyl, preferably a C4-C6 cycloalkyl, more preferably a cyclohexyl,
an aryl group, preferably a phenyl or a naphthyl group, possibly mono or or polysubstituted, in particular disubstituted, by
a halogen chosen among Cl, F, I and Br, or
a linear or branched, saturated or not, C1-C7 alkyl, or
a group —CO—R6, R6 being chosen among the group consisting of: —OH, —NH$_2$, or salt thereof, and —O—R7, R7 being a linear or branched, saturated or not, C1-C7 alkyl, or
a group —O—R8, R8 being a linear or branched, saturated or not, C1-C7 alkyl, or
a group —NO$_2$,
a combination of the above,
and
an heteroaryl group, preferably a pyridyl or an isoquinolinyl, possibly mono or polysubstituted, in particular disubstituted, by
a halogen chosen among Cl, F, I and Br, or
a linear or branched, saturated or not, C1-C7 alkyl, or
a group —CO—R6, R6 being chosen among the group consisting of: —OH, —NH$_2$, or salt thereof, and —O—R7, R7 being a linear or branched, saturated or not, C1-C7 alkyl, or
a group —O—R8, R8 being a linear or branched, saturated or not, C1-C7 alkyl, or
a combination of the above,
provided that
if R1=H, then R2 can only represent an isoquinolinyl or a naphthyl, or a phenyl substituted by two halogens, and
if R1≠H, then if R2 is an aryl different from a naphthyl, or an hetero aryl, substituted by one linear or branched, saturated or not, C1-C7 alkyl, said aryl or heteroaryl is also substituted by at least another group, which is different from a C1-C7 alkyl,
for its use for the treatment of pathologies involving an excess of activity of at least one member of the kallikrein family, preferably belonging to the group consisting of KLK5, KLK7 and KLK14.

According to another embodiment, the present invention relates to the above mentioned compounds having the following formula (I-1b):

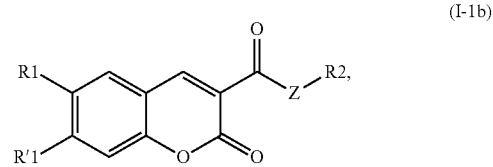

(I-1b)

wherein
Z represents O or S,
R1 represents at least one group chosen among the group consisting of:
hydrogen
a linear or branched, saturated or not, C1-C7 alkyl, preferably a methyl group, substituted, or not, by a halogen chosen among Cl, F, I and Br,
a linear or branched, saturated or not, C1-C7 alkyl, preferably a methyl group, substituted by a hydroxyl or a —O—R12 group, wherein R12 is a linear or branched, saturated or not, C1-C7 alkyl, preferably a hydroxyl, a group —CH2—O—CO—R5, wherein R5 is chosen among a hydrogen atom, and a linear or branched, saturated or not, C1-C7 alkyl, substituted or not by at least one halogen chosen among Cl, F, I and Br, a group —O—R13, wherein R13 is chosen among hydrogen and a linear or branched, saturated or not, C1-C7 alkyl, R13 being preferably a hydrogen, an amine

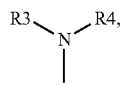

or a salt thereof, wherein R3 and R4, independently from each other, are chosen among hydrogen and a linear or branched, saturated or not, C1-C5 alkyl, and a group

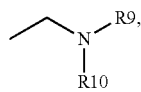

or a salt thereof, wherein R9 and R10, independently from each other, are chosen among:
hydrogen,
a linear or branched, saturated or not, C1-C5 alkyl,
—CO—R5, wherein R5 is chosen among a hydrogen atom, and a linear or branched, saturated or not, C1-C7 alkyl, substituted or not by at least one halogen chosen among Cl, F, I and Br,
—SO2—R11, wherein R11 is a linear or branched, saturated or not, C1-C7 alkyl, R'1 represents a group chosen among hydrogen and —O—R14, wherein R14 is chosen among hydrogen and a linear or branched, saturated or not, C1-C7 alkyl, R14 being preferably a hydrogen, R'1 being preferably a hydrogen, provided that R'1 represents hydrogen when R1 does not represent a —O—R13 group, and R2 is chosen among the group consisting of:
a linear or branched, saturated or not, C1-C7 alkyl, preferably a C1-C3 alkyl,
a C3-C6 cycloalkyl, preferably a C4-C6 cycloalkyl, more preferably a cyclohexyl,
an aryl group, preferably a phenyl group, possibly mono or polysubstituted, in particular disubstituted, by
a halogen chosen among Cl, F, I and Br, or
a linear or branched, saturated or not, C1-C7 alkyl, or
a group —CO—R6, R6 being chosen among the group consisting of: —OH, —NH2, or salt thereof, and —O—R7, R7 being a linear or branched, saturated or not, C1-C7 alkyl, or
a group —O—R8, R8 being a linear or branched, saturated or not, C1-C7 alkyl, or
a group —NO2,
a group —CN,
a combination of the above, and an heteroaryl group, preferably a pyridyl or an isoquinolinyl, possibly mono or polysubstituted, in particular disubstituted, by
a halogen chosen among Cl, F, I and Br, or
a linear or branched, saturated or not, C1-C7 alkyl, or
a group —CO—R6, R6 being chosen among the group consisting of: —OH, —NH2, or salt thereof, and —O—R7, R7 being a linear or branched, saturated or not, C1-C7 alkyl, or
a group —O—R8, R8 being a linear or branched, saturated or not, C1-C7 alkyl, or
a combination of the above, provided that
if R1=H, then R2 can only represent an isoquinolinyl or a phenyl substituted by two halogens, and
if R1≠H, if R2 is an aryl or an hetero aryl substituted by one a linear or branched, saturated or not, C1-C7 alkyl, said aryl or heteroaryl is also substituted by at least another group different from a C1-C7 alkyl.

According to another embodiment, the present invention relates to the above mentioned compounds having the following formula (I-1b):

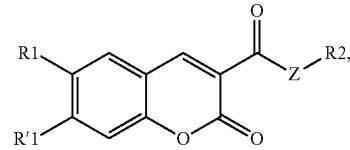

(I-1b)

wherein
Z represents O or S,
R1 represents at least one group chosen among the group consisting of:
hydrogen
a linear or branched, saturated or not, C1-C7 alkyl, preferably a methyl group, substituted, or not, by a halogen chosen among Cl, F, I and Br,
a linear or branched, saturated or not, C1-C7 alkyl, preferably a methyl group, substituted by a hydroxyl or a —O—R12 group, wherein R12 is a linear or branched, saturated or not, C1-C7 alkyl, preferably a hydroxyl,
a group —CH2—O—CO—R5, wherein R5 is chosen among a hydrogen atom, and a linear or branched, saturated or not, C1-C7 alkyl, substituted or not by at least one halogen chosen among Cl, F, I and Br,
a group —O—R13, wherein R13 is chosen among hydrogen and a linear or branched, saturated or not, C1-C7 alkyl, R13 being preferably a hydrogen,
an amine

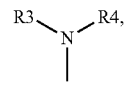

or a salt thereof, wherein R3 and R4, independently from each other, are chosen among hydrogen and a linear or branched, saturated or not, C1-C5 alkyl, and a group

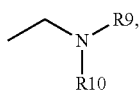

or a salt thereof, wherein R9 and R10, independently from each other, are chosen among:
hydrogen,
a linear or branched, saturated or not, C1-C5 alkyl,
—CO—R5, wherein R5 is chosen among a hydrogen atom, and a linear or branched, saturated or not, C1-C7 alkyl, substituted or not by at least one halogen chosen among Cl, F, I and Br,
—$SO_2$—R11, wherein R11 is a linear or branched, saturated or not, C1-C7 alkyl, R'1 represents a group chosen among hydrogen and —O—R14, wherein R14 is chosen among hydrogen and a linear or branched, saturated or not, C1-C7 alkyl, R14 being preferably a hydrogen, R'1 being preferably a hydrogen, provided that R'1 represents hydrogen when R1 does not represent a —O—R13 group,
and
R2 is chosen among the group consisting of:
a linear or branched, saturated or not, C1-C7 alkyl, preferably a C1-C3 alkyl,
a C3-C6 cycloalkyl, preferably a C4-C6 cycloalkyl, more preferably a cyclohexyl,
an aryl group, preferably a phenyl or a naphthyl group, possibly mono or or polysubstituted, in particular disubstituted, by
a halogen chosen among Cl, F, I and Br, or
a linear or branched, saturated or not, C1-C7 alkyl, or
a group —CO—R6, R6 being chosen among the group consisting of: —OH, —$NH_2$, or salt thereof, and —O—R7, R7 being a linear or branched, saturated or not, C1-C7 alkyl, or
a group —O—R8, R8 being a linear or branched, saturated or not, C1-C7 alkyl, or
a group —$NO_2$,
a group —CN,
a combination of the above,
and
an heteroaryl group, preferably a pyridyl or an isoquinolinyl, possibly mono or polysubstituted, in particular disubstituted, by
a halogen chosen among Cl, F, I and Br, or
a linear or branched, saturated or not, C1-C7 alkyl, or
a group —CO—R6, R6 being chosen among the group consisting of: —OH, —$NH_2$, or salt thereof, and —O—R7, R7 being a linear or branched, saturated or not, C1-C7 alkyl, or
a group —O—R8, R8 being a linear or branched, saturated or not, C1-C7 alkyl, or
a combination of the above,
provided that
if R1=H, then R2 can only represent an isoquinolinyl or a naphthyl, or a phenyl substituted by two halogens, and
if R1≠H, then if R2 is an aryl different from a naphthyl, or an hetero aryl, substituted by one linear or branched, saturated or not, C1-C7 alkyl, said aryl or heteroaryl is also substituted by at least another group, which is different from a C1-C7 alkyl,
for its use for the treatment of pathologies involving an excess of activity of at least one member of the kallikrein family, preferably belonging to the group consisting of KLK5, KLK7 and KLK14.

The present invention also relates to compounds of formula (I-h1) as presented below:

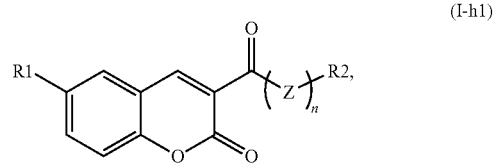

(I-h1)

wherein n equals 0 or 1,
and wherein
if n=1, Z represents O or S,
R1 represents —$CH_2$—Br or —$CH_2$—F,
R2 is chosen among the group consisting of:
a linear or branched, saturated or not, C1-C7 alkyl, preferably a C1-C3 alkyl,
a C3-C6 cycloalkyl, preferably a C4-C6 cycloalkyl, more preferably a cyclohexyl,
an aryl group, preferably a phenyl or a naphthyl group, possibly mono or or polysubstituted, in particular disubstituted, by
a halogen chosen among Cl, F, I and Br, or
a linear or branched, saturated or not, C1-C7 alkyl, or
a group —CO—R6, R6 being chosen among the group consisting of: —OH, —$NH_2$, or salt thereof, and —O—R7, R7 being a linear or branched, saturated or not, C1-C7 alkyl, or
a group —O—R8, R8 being a linear or branched, saturated or not, C1-C7 alkyl, or
a group —$NO_2$,
a group —CN,
a combination of the above,
and
an heteroaryl group, preferably a pyridyl or an isoquinolinyl, possibly mono or polysubstituted, in particular disubstituted, by
a halogen chosen among Cl, F, I and Br, or
a linear or branched, saturated or not, C1-C7 alkyl, or
a group —CO—R6, R6 being chosen among the group consisting of: —OH, —$NH_2$, or salt thereof, and —O—R7, R7 being a linear or branched, saturated or not, C1-C7 alkyl, or
a group —O—R8, R8 being a linear or branched, saturated or not, C1-C7 alkyl, or
a combination of the above,
provided that
when n=0, R2 is a methyl group or a cycloalkyl group, preferably a cyclohexyl group,
when n=1, if R2 is an aryl different from a naphthyl, or an hetero aryl, substituted by one linear or branched, saturated or not, C1-C7 alkyl, said aryl or heteroaryl is also substituted by at least another group different from a C1-C7 alkyl,
for its use for the treatment of pathologies involving an excess of activity of at least one member of the kallikrein family, preferably belonging to the group consisting of KLK5, KLK7 and KLK14.

According to another embodiment, the present invention relates to the above mentioned compounds having the following formula (I-h2):

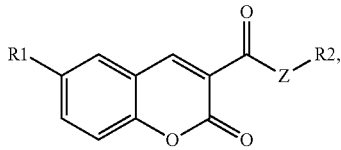

(I-h2)

wherein
Z represents O or S,
R1 represents —CH₂—Br or —CH₂—F,
R2 is chosen among the group consisting of:
    a linear or branched, saturated or not, C1-C7 alkyl, preferably a C1-C3 alkyl,
    a C3-C6 cycloalkyl, preferably a C4-C6 cycloalkyl, more preferably a cyclohexyl,
    an aryl group, preferably a phenyl or a naphthyl group, possibly mono or or polysubstituted, in particular disubstituted, by
        a halogen chosen among Cl, F, I and Br, or
        a linear or branched, saturated or not, C1-C7 alkyl, or
        a group —CO—R6, R6 being chosen among the group consisting of: —OH, —NH₂, or salt thereof, and —O—R7, R7 being a linear or branched, saturated or not, C1-C7 alkyl, or
        a group —O—R8, R8 being a linear or branched, saturated or not, C1-C7 alkyl, or
        a group —NO₂,
        a group —CN,
        a combination of the above,
    and
    an heteroaryl group, preferably a pyridyl or an isoquinolinyl, possibly mono or polysubstituted, in particular disubstituted, by
        a halogen chosen among Cl, F, I and Br, or
        a linear or branched, saturated or not, C1-C7 alkyl, or
        a group —CO—R6, R6 being chosen among the group consisting of: —OH, —NH₂, or salt thereof, and —O—R7, R7 being a linear or branched, saturated or not, C1-C7 alkyl, or
        a group —O—R8, R8 being a linear or branched, saturated or not, C1-C7 alkyl, or
        a combination of the above,
    provided that
    if R2 is an aryl different from a naphthyl, or an hetero aryl, substituted by one linear or branched, saturated or not, C1-C7 alkyl, said aryl or heteroaryl is also substituted by at least another group, which is different from a C1-C7 alkyl,
for its use for the treatment of pathologies involving an excess of activity of at least one member of the kallikrein family, preferably belonging to the group consisting of KLK5, KLK7 and KLK14.

According to another embodiment, the present invention relates to the above mentioned compounds having the following formula (I-h3):

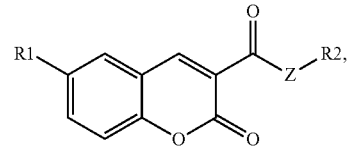

(I-h3)

wherein
Z represents O or S,
R1 represents —CH₂—Br or —CH₂—F,
R2 is an aryl group, preferably a phenyl or a naphthyl group, possibly mono or or polysubstituted, in particular disubstituted, by
    a halogen chosen among Cl, F, I and Br, or
    a linear or branched, saturated or not, C1-C7 alkyl, or
    a group —CO—R6, R6 being chosen among the group consisting of: —OH, —NH₂, or salt thereof, and —O—R7, R7 being a linear or branched, saturated or not, C1-C7 alkyl, or
    a group —O—R8, R8 being a linear or branched, saturated or not, C1-C7 alkyl, or
    a group —NO₂,
    a group —CN,
    a combination of the above,
provided that
if R2 is an aryl different from a naphthyl, or an hetero aryl, substituted by one linear or branched, saturated or not, C1-C7 alkyl, said aryl or heteroaryl is also substituted by at least another group, which is different from a C1-C7 alkyl,
for its use for the treatment of pathologies involving an excess of activity of at least one member of the kallikrein family, preferably belonging to the group consisting of KLK5, KLK7 and KLK14.

According to another embodiment, the present invention relates to the above mentioned compounds having the following formula (I-n1):

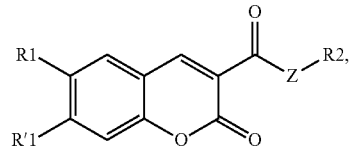

(I-n1)

wherein
Z represents O or S,
R1 represents at least one group chosen among the group consisting of:
    hydrogen
    a linear or branched, saturated or not, C1-C7 alkyl, preferably a methyl group, substituted, or not, by a halogen chosen among Cl, F, I and Br,
    a linear or branched, saturated or not, C1-C7 alkyl, preferably a methyl group, substituted by a hydroxyl or a —O—R12 group, wherein R12 is a linear or branched, saturated or not, C1-C7 alkyl, preferably a hydroxyl,
    a group —CH₂—O—CO—R5, wherein R5 is chosen among a hydrogen atom, and a linear or branched, saturated or not, C1-C7 alkyl, substituted or not by at least one halogen chosen among Cl, F, I and Br, a group —O—R13, wherein R13 is chosen among hydrogen and a linear or branched, saturated or not, C1-C7 alkyl, R13 being preferably a hydrogen, an amine

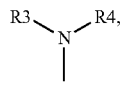

or a salt thereof, wherein R3 and R4, independently from each other, are chosen among hydrogen and a linear or branched, saturated or not, C1-C5 alkyl, and a group

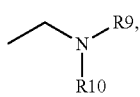

or a salt thereof, wherein R9 and R10, independently from each other, are chosen among:

hydrogen, a linear or branched, saturated or not, C1-C5 alkyl,

—CO—R5, wherein R5 is chosen among a hydrogen atom, and a linear or branched, saturated or not, C1-C7 alkyl, substituted or not by at least one halogen chosen among Cl, F, I and Br, —SO$_2$—R11, wherein R11 is a linear or branched, saturated or not, C1-C7 alkyl, R'1 represents a group chosen among hydrogen and —O—R14, wherein R14 is chosen among hydrogen and a linear or branched, saturated or not, C1-C7 alkyl, R14 being preferably a hydrogen, R'1 being preferably a hydrogen, provided that R'1 represents hydrogen when R1 does not represent a —O—R13 group, and R2 is a naphthyl group, in particular a 1-naphthyl or a 2-naphthyl group, possibly mono or polysubstituted, in particular disubstituted, by a halogen chosen among Cl, F, I and Br, or a linear or branched, saturated or not, C1-C7 alkyl, or a group —CO—R6, R6 being chosen among the group consisting of: —OH, —NH$_2$, or salt thereof, and —O—R7, R7 being a linear or branched, saturated or not, C1-C7 alkyl, or a group —O—R8, R8 being a linear or branched, saturated or not, C1-C7 alkyl, or a group —NO$_2$, a group —CN, a combination of the above, for its use for the treatment of pathologies involving an excess of activity of at least one member of the kallikrein family, preferably belonging to the group consisting of KLK5, KLK7 and KLK14.

According to another embodiment, the present invention relates to the above mentioned compounds having the following formula (I-n2):

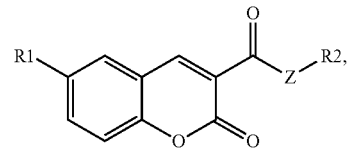

(I-n2)

wherein

Z represents O or S,

R1 represents at least one group chosen among the group consisting of:

hydrogen a linear or branched, saturated or not, C1-C7 alkyl, preferably a methyl group, substituted, or not, by a halogen chosen among Cl, F, I and Br, a linear or branched, saturated or not, C1-C7 alkyl, preferably a methyl group, substituted by a hydroxyl or a —O—R12 group, wherein R12 is a linear or branched, saturated or not, C1-C7 alkyl, preferably a hydroxyl, a group —CH$_2$—O—CO—R5, wherein R5 is chosen among a hydrogen atom, and a linear or branched, saturated or not, C1-C7 alkyl, substituted or not by at least one halogen chosen among Cl, F, I and Br, a group —O—R13, wherein R13 is chosen among hydrogen and a linear or branched, saturated or not, C1-C7 alkyl, R13 being preferably a hydrogen, an amine

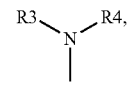

or a salt thereof, wherein R3 and R4, independently from each other, are chosen among hydrogen and a linear or branched, saturated or not, C1-C5 alkyl, and a group

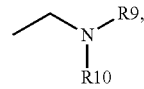

or a salt thereof, wherein R9 and R10, independently from each other, are chosen among:

hydrogen, a linear or branched, saturated or not, C1-C5 alkyl,

—CO—R5, wherein R5 is chosen among a hydrogen atom, and a linear or branched, saturated or not, C1-C7 alkyl, substituted or not by at least one halogen chosen among Cl, F, I and Br, —SO$_2$—R11, wherein R11 is a linear or branched, saturated or not, C1-C7 alkyl, R2 is a naphthyl group, in particular a 1-naphthyl or a 2-naphthyl group, possibly mono or polysubstituted, in particular disubstituted, by a halogen chosen among Cl, F, I and Br, or a linear or branched, saturated or not, C1-C7 alkyl, or a group —CO—R6, R6 being chosen among the group consisting of: —OH, —NH$_2$, or salt thereof, and —O—R7, R7 being a linear or branched, saturated or not, C1-C7 alkyl, or a group —O—R8, R8 being a linear or branched, saturated or not, C1-C7 alkyl, or a group —NO$_2$, a group —CN, a combination of the above, for its use for the treatment of pathologies involving an excess of activity of at least one member of the kallikrein family, preferably belonging to the group consisting of KLK5, KLK7 and KLK14.

According to another embodiment, the present invention relates to the above mentioned compounds having the following formula (I-n3):

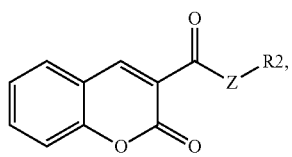

(I-n3)

wherein

Z represents O or S,

R2 is a naphthyl group, in particular a 1-naphthyl or a 2-naphthyl group, possibly mono or polysubstituted, in particular disubstituted, by a halogen chosen among Cl, F, I and Br, or a linear or branched, saturated or not, C1-C7 alkyl, or a group —CO—R6, R6 being chosen among the group consisting of: —OH, —NH$_2$, or salt thereof, and —O—R7, R7 being a linear or branched, saturated or not, C1-C7 alkyl, or a group —O—R8, R8 being a linear or branched, saturated or not, C1-C7 alkyl, or a group —NO$_2$, a group —CN, a combination of the above, for its use for the treatment of pathologies involving an excess of activity of at least one member of the kallikrein family, preferably belonging to the group consisting of KLK5, KLK7 and KLK14.

According to another embodiment, the present invention relates to the above mentioned compounds belonging to the group consisting of:

MFS36

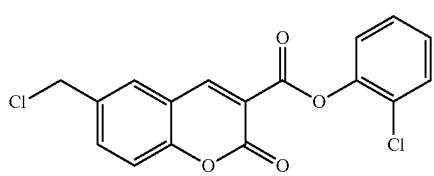

LP15

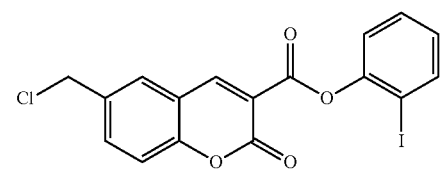

-continued

IK11

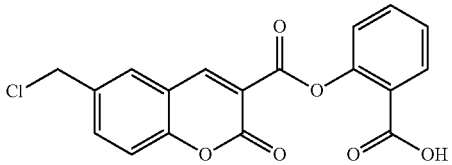

IK1

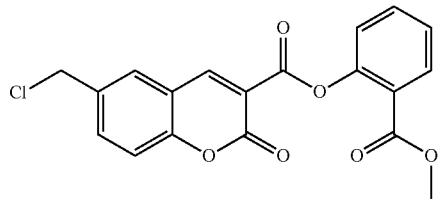

LP60

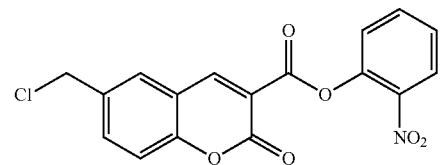

IK5

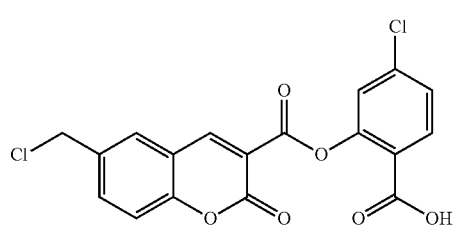

LP73

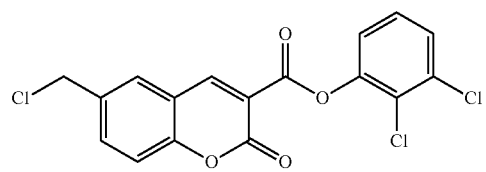

LP53

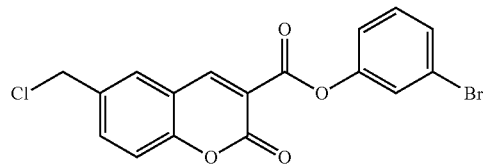

LP8

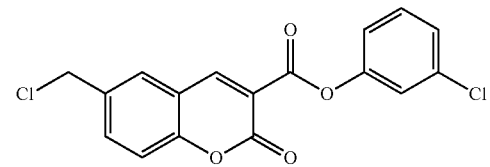

LP46

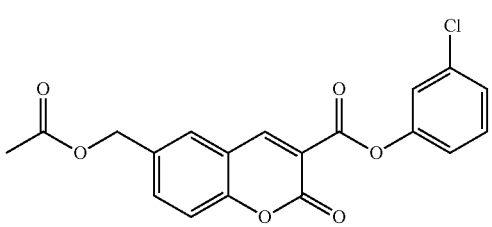

CFL16
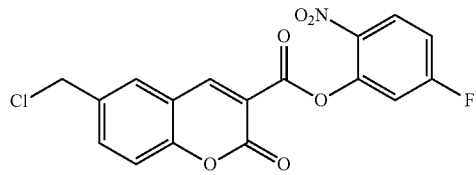
LP75
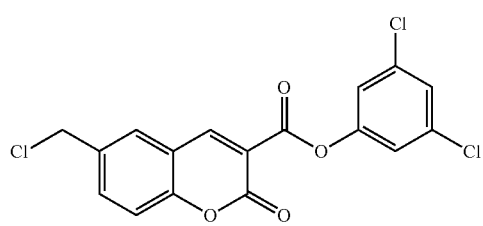
LP61
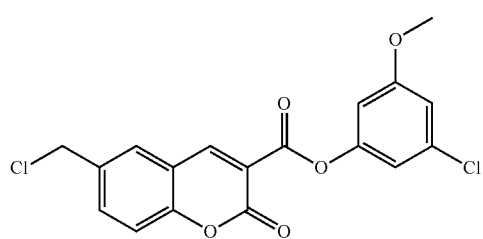
CFL25
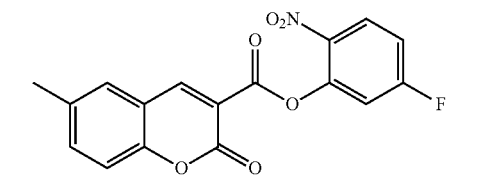
IK8
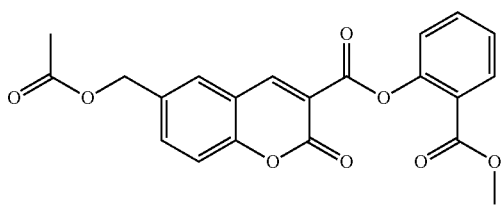
CFL4
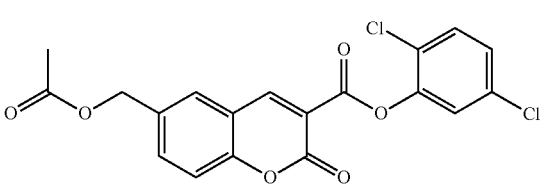
LP7
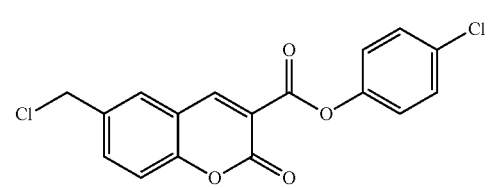
LP16
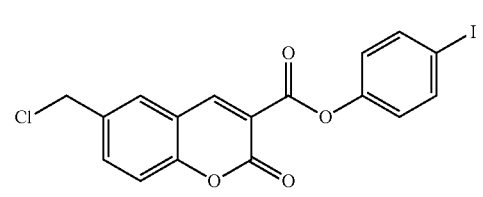
LP18
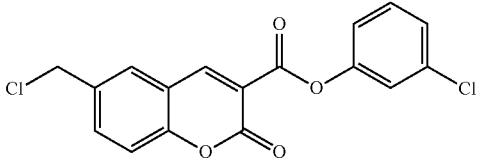
D5
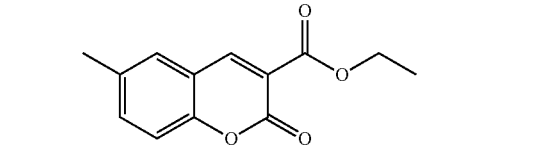
MFS2
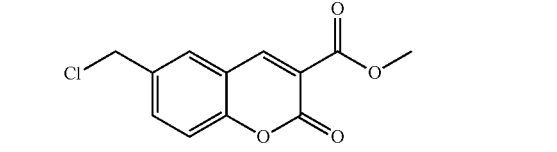
MFS3
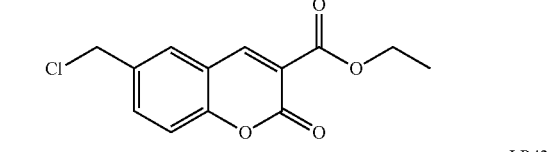
LP43
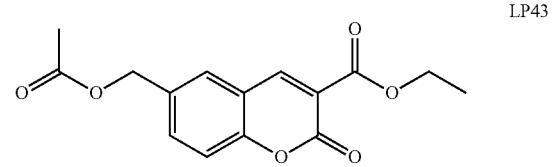
(CFL7)
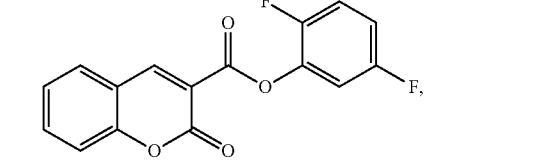
(D9)
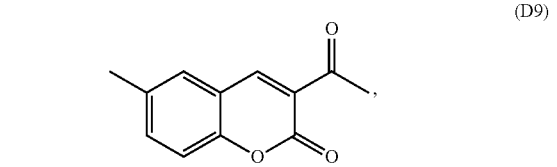
(LP2)
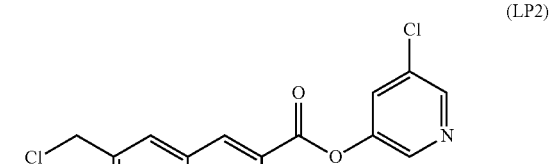
(LP42)
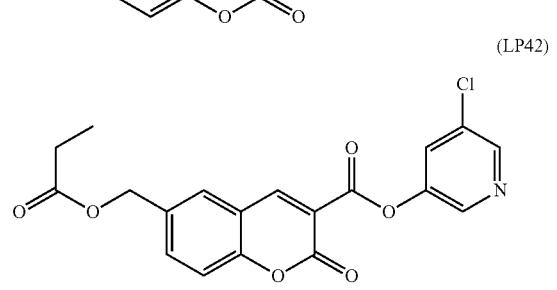

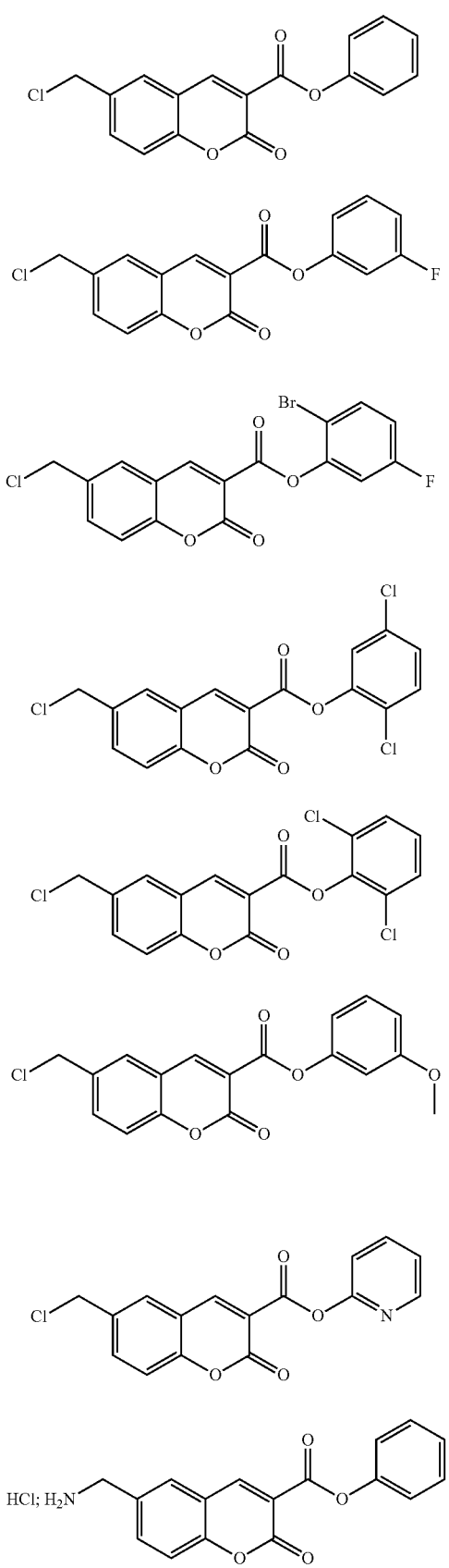
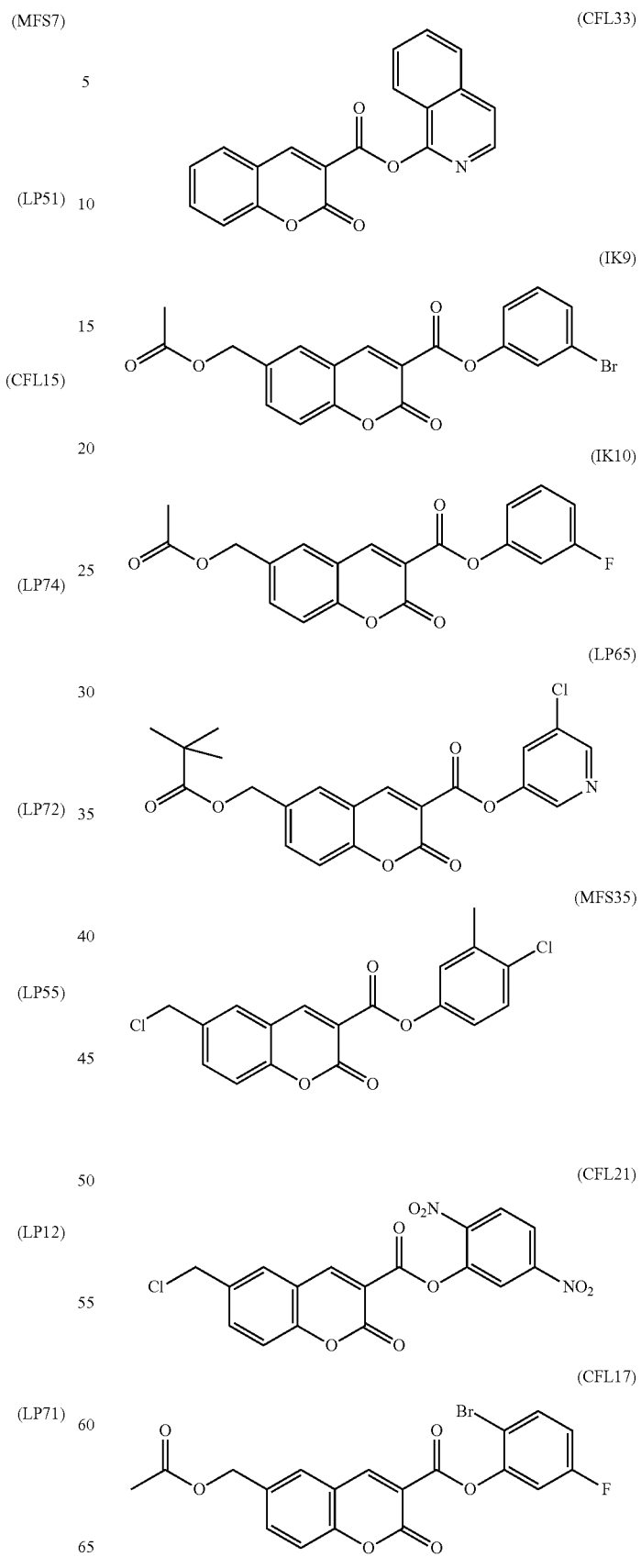

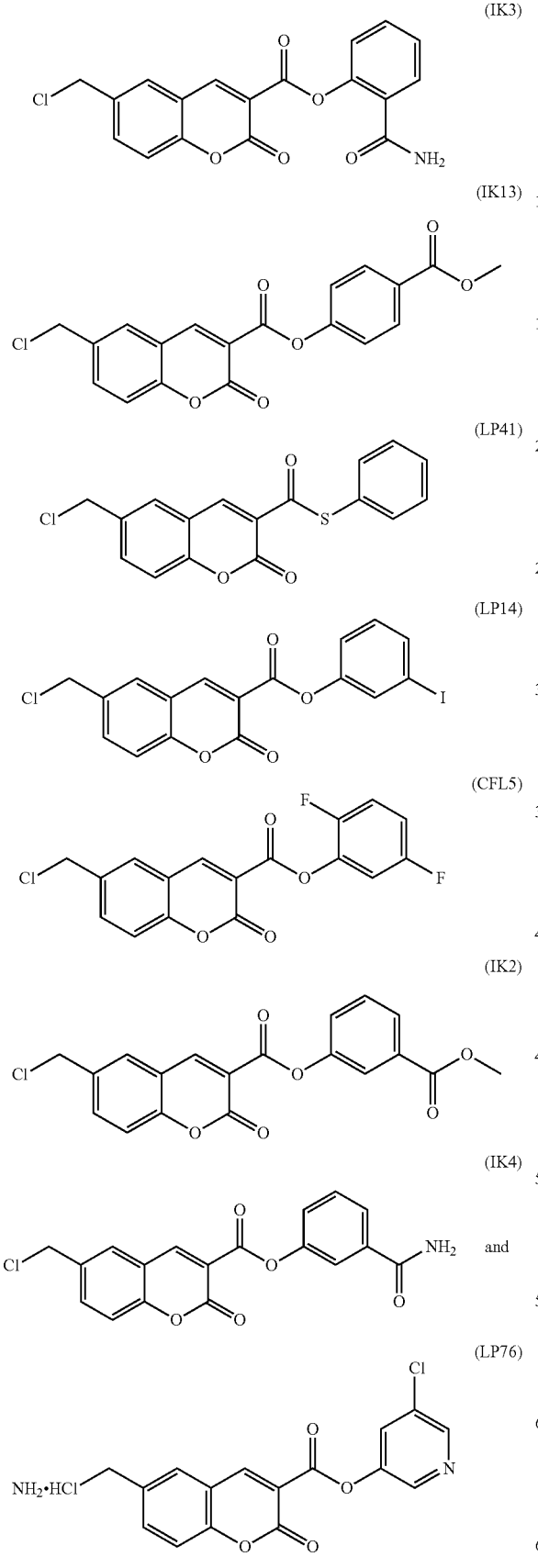
According to another embodiment, the present invention relates to the above mentioned compounds belonging to the group consisting of:
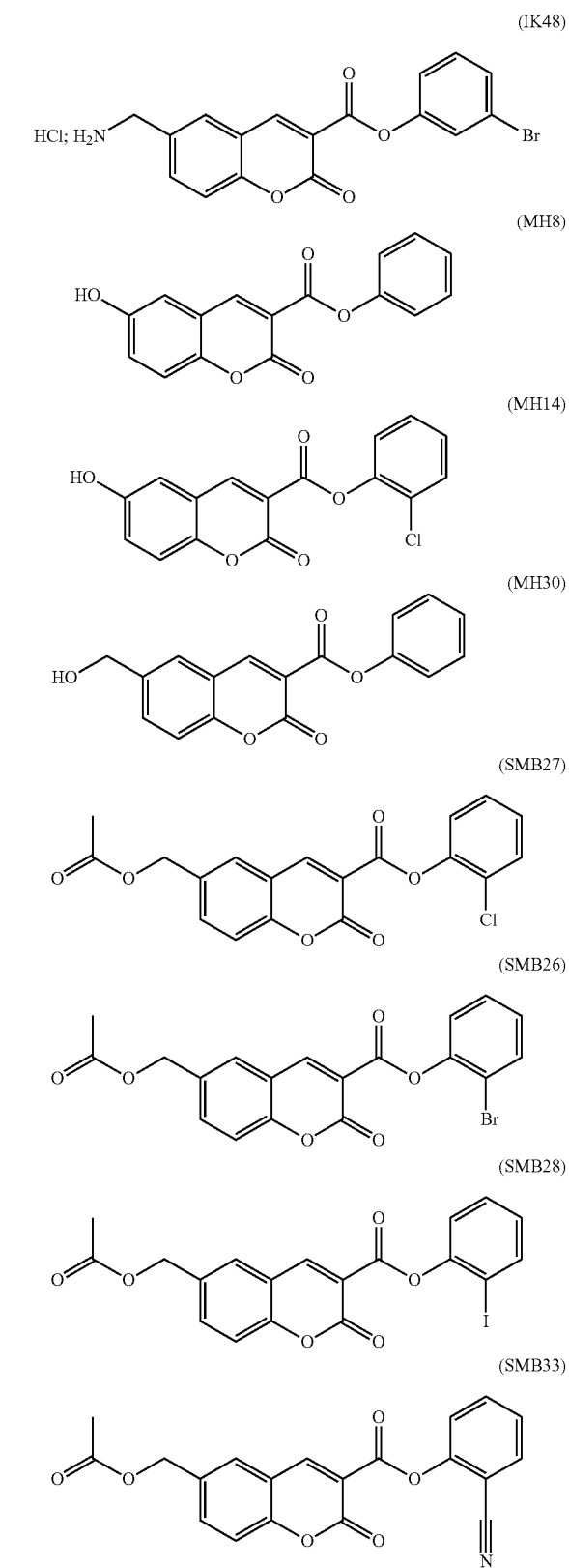

(IK53)
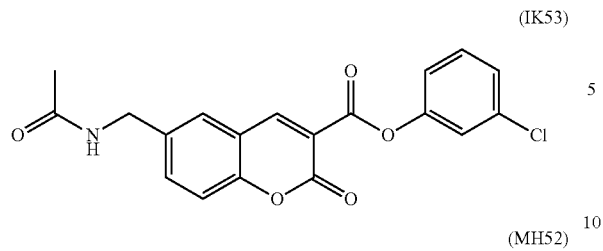

(MH52)
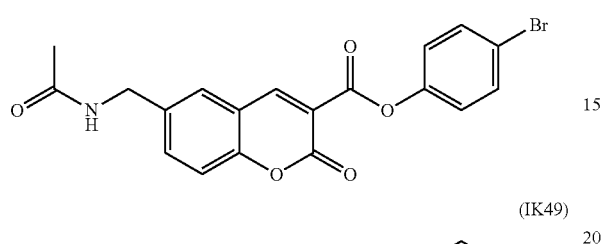

(IK49)
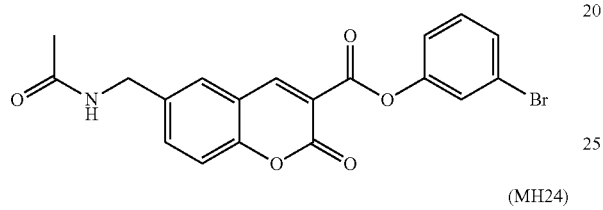

(MH24)
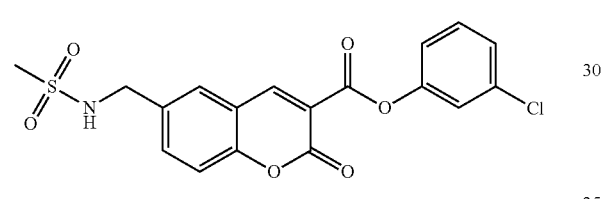

(MH22)
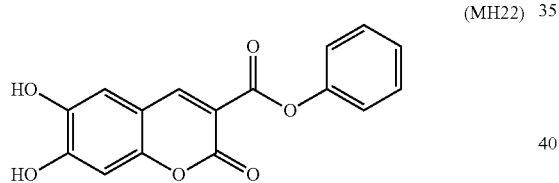

According to another embodiment, the present invention relates to the above mentioned compounds belonging to the group consisting of:

(MFS33)
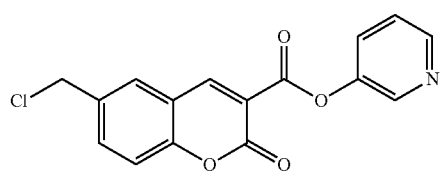

(JFR1)
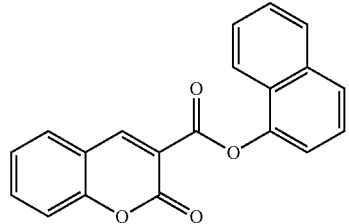

(JFR2)
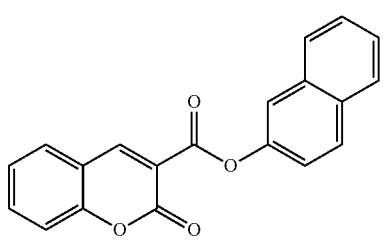

(JFR5)
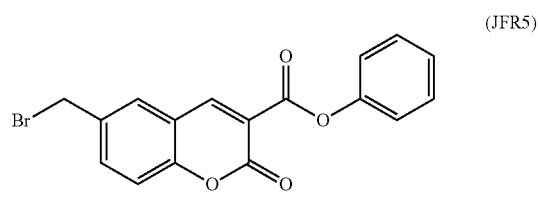

(JFR7)
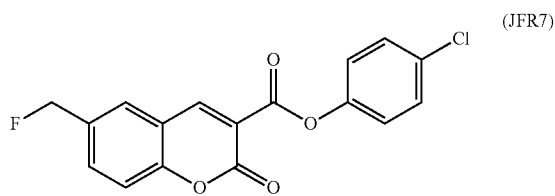

(JFR8)
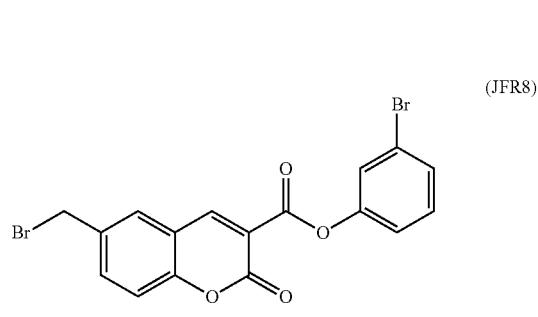

(JFR9)
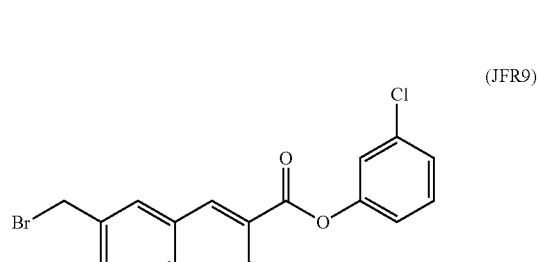

(JFR11.)

The above mentioned compounds present an inhibitory activity against at least one kallikrein, among KLK5, KLK7 and KLK14, or even a combination of two or three of said kallikreins.

According to another embodiment, the present invention relates to the above mentioned compounds having the following formula (II):

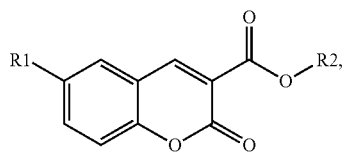

wherein
R1 represents —CH$_2$—Cl or —CH$_2$OCOC$_2$H$_5$, and
R2 represents
  a pyridyl substituted by a Cl, or
  a phenyl substituted, or not, either by a group —OCH$_3$ or by one or two halogens chosen among Cl, Br or I.

Compounds having the formula (II) and the above mentioned significations for R1 and R2 present an inhibitory activity against KLK7.

The coumarin derivatives of formula II are enzyme inhibitors, molecules that binds to enzymes and decreases their activity.

A test to show the inhibitory activity consists in incubating KLK7 and a coumarin derivative and then determining the activity of KLK7 by comparison of the initial rates to those obtained in control experiments without coumarin derivative. The values of "IC50" (inhibitor concentrations giving 50% inhibition) express the inhibitory activity.

According to another embodiment, the present invention relates to the above mentioned compounds having the following formula (II):

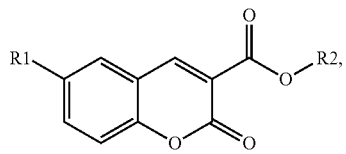

wherein
R1 represents:
  a group —O—R13, wherein R13 is chosen among hydrogen and a linear or branched, saturated or not, C1-C7 alkyl, R13 being preferably a hydrogen,
  —CH$_2$—Cl,
  —CH$_2$OCOC$_2$H$_5$, or
  a group

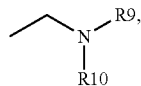

or a salt thereof, wherein R9 and R10, independently from each other, are chosen among:
  hydrogen,
  a linear or branched, saturated or not, C1-C5 alkyl,
  —CO—R5, wherein R5 is chosen among a hydrogen atom, and a linear or branched, saturated or not, C1-C7 alkyl, substituted or not by at least one halogen chosen among Cl, F, I and Br,
  —SO$_2$—R11, wherein R11 is a linear or branched, saturated or not, C1-C7 alkyl,
and
R2 represents
  a pyridyl substituted by a Cl, or
  a phenyl substituted, or not, either by a group —OCH$_3$ or by one or two halogens chosen among Cl, Br or I, providing at least one of R9 and R10 represents —CO—R5 or —SO$_2$—R11, preferably R9 being —CO—R5 and R10 being hydrogen or R9 being —SO$_2$—R11 and R10 being hydrogen.

Compounds having the formula (II) and the above mentioned significations for R1 and R2 present an inhibitory activity against KLK7.

The coumarin derivatives of formula II are enzyme inhibitors, molecules that binds to enzymes and decreases their activity.

According to another embodiment, the present invention relates to the above mentioned compounds having the following formula (II):

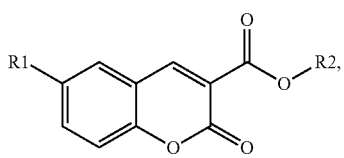

wherein
R1 represents:
  an hydrogen,
  a group —O—R13, wherein R13 is chosen among hydrogen and a linear or branched, saturated or not, C1-C7 alkyl, R13 being preferably a hydrogen,
  —CH$_2$—Cl,
  —CH$_2$—Br,
  —CH$_2$—F,
  —CH$_2$OCOC$_2$H$_5$, or
  a group

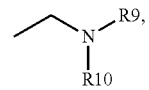

or a salt thereof, wherein R9 and R10, independently from each other, are chosen among:
  hydrogen,
  a linear or branched, saturated or not, C1-C5 alkyl,
  —CO—R5, wherein R5 is chosen among a hydrogen atom, and a linear or branched, saturated or not, C1-C7 alkyl, substituted or not by at least one halogen chosen among Cl, F, I and Br,
  —SO$_2$—R11, wherein R11 is a linear or branched, saturated or not, C1-C7 alkyl,
and
R2 represents
  a pyridyl substituted by a Cl, or
  a phenyl substituted, or not, either by a group —OCH$_3$ or by one or two halogens chosen among Cl, Br, F or I, or
  a naphthyl substituted, or not, either by a group —OCH$_3$ or by one or two halogens chosen among Cl, Br, F or I, providing that:
at least one of R9 and R10 represents —CO—R5 or —SO$_2$—R11, preferably R9 being —CO—R5 and R10 being hydrogen or R9 being —SO$_2$—R11 and R10 being hydrogen,
if R1=H, R2 can only represent a naphthyl.

Compounds having the formula (II) and the above mentioned significations for R1 and R2 present an inhibitory activity against KLK7.

The coumarin derivatives of formula II are enzyme inhibitors, molecules that binds to enzymes and decreases their activity.

According to another embodiment, the present invention relates to the above mentioned compounds chosen among the group consisting of:

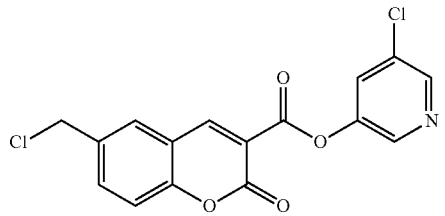
(LP2)

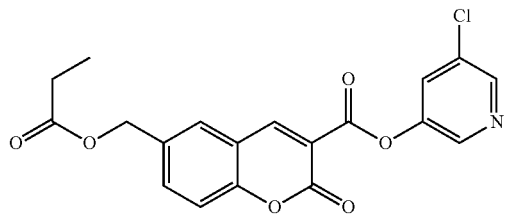
(LP42)

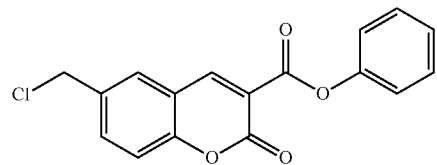
(MFS7)

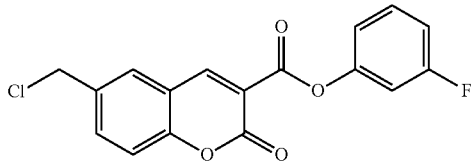
(LP51)

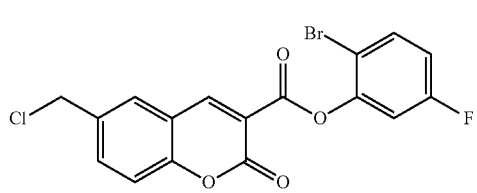
(CFL15)

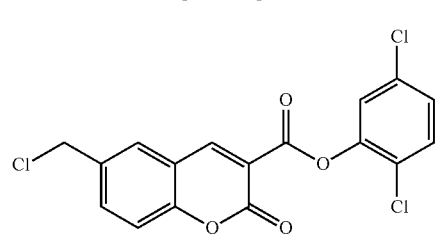
(LP74)

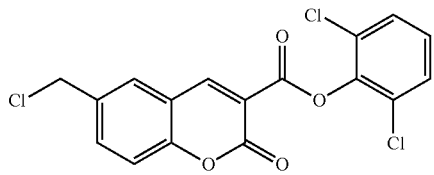
(LP72)

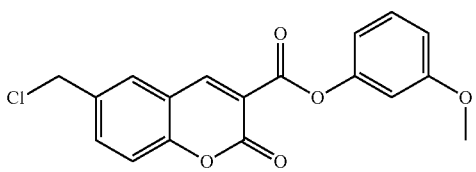
(LP55)

Compounds above show an inhibitory activity against KLK7.

According to another embodiment, the present invention relates to the above mentioned compounds belonging to the group consisting of:

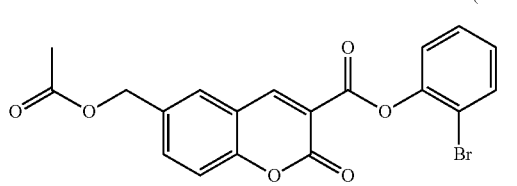
(SMB26)

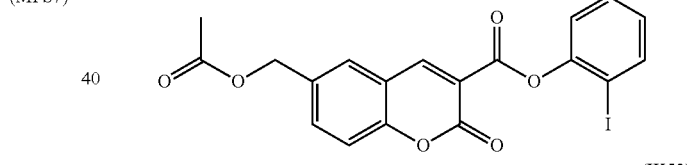
(SMB28)

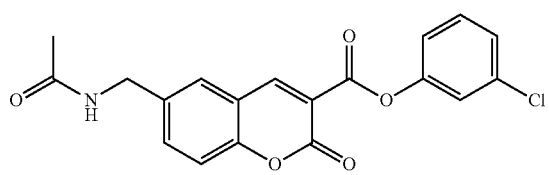
(IK53)

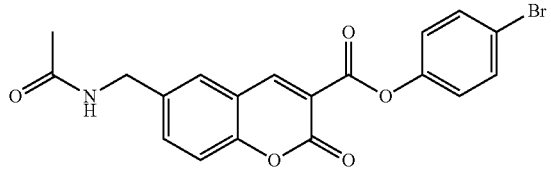
(MH52)

(IK49)

-continued (MH8)
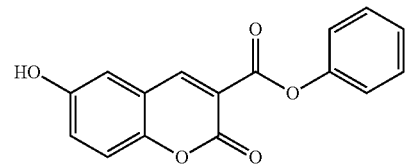

(MH14)
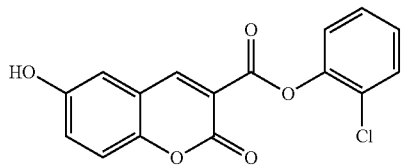

(MH24)
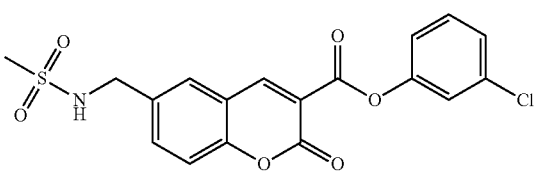

Compounds above show an inhibitory activity against KLK7.

According to another embodiment, the present invention relates to the above mentioned compounds belonging to the group consisting of:

(JFR1)
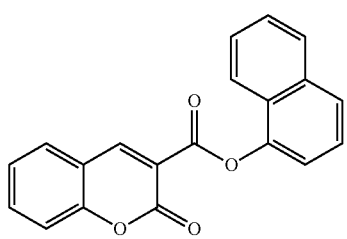

(JFR2)
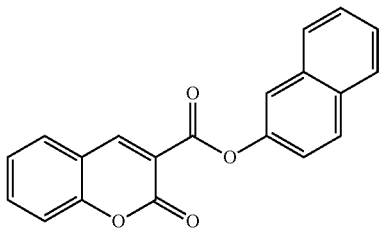

(JFR5)
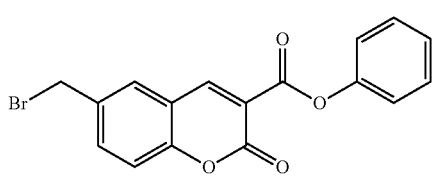

(JFR7)
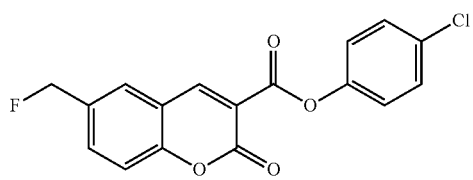

-continued (JFR8)
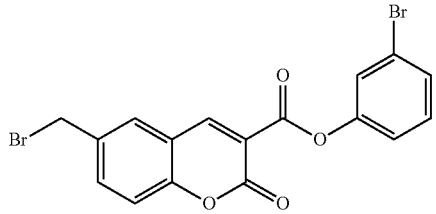

(JFR9)
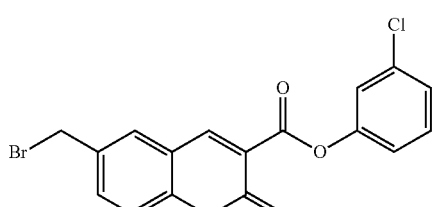

(JFR11)
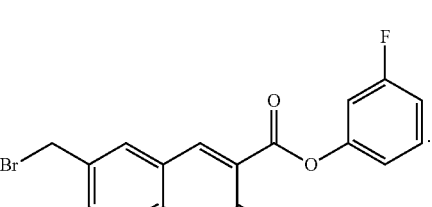

Compounds above show an inhibitory activity against KLK7.

According to another embodiment, the present invention relates to the above mentioned compounds having the following formula (II):

(II)
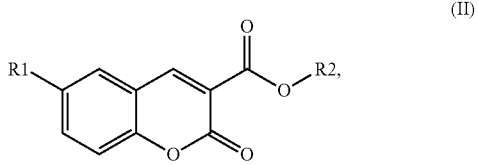

wherein
R1 represents —CH$_2$—Cl, —CH$_2$OCOCH$_3$, —CH$_3$, —NH$_2$, and its salts thereof, or H, and
R2 represents:
  an isoquinolinyl, or
  —CH$_3$, or
  a pyridyl, or
  a phenyl, substituted or not by a halogen,
provided that
  if R1=H, R2 can only represent an isoquinolinyl, and
  if R1=CH$_3$, R2 can only represent a CH$_3$.

Compounds having the formula (II) and the significations for R1 and R2 noted above show an inhibitory activity against KLK5.

A test to show the inhibitory activity consists in incubating KLK5 and a coumarin derivative and then determining the activity of KLK5 by comparison of the initial rates to those obtained in control experiments without coumarin derivative. The values of "IC50" (inhibitor concentrations giving 50% inhibition) express the inhibitory activity.

According to another embodiment, the present invention relates to the above mentioned compounds having the following formula (II):

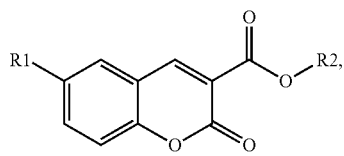
(II)

wherein
R1 represents —CH$_2$—Cl, —CH$_2$OCOCH$_3$, —CH$_3$, —CH$_2$—NH$_2$, and its salts thereof, or H, and
R2 represents:
  an isoquinolinyl, or
  —CH$_3$, or
  a pyridyl, or
  a phenyl, substituted or not by a halogen,
  provided that
    if R1=H, R2 can only represent an isoquinolinyl, and
    if R1=CH$_3$, R2 can only represent a CH$_3$.

Compounds having the formula (II) and the significations for R1 and R2 noted above show an inhibitory activity against KLK5.

According to another embodiment, the present invention relates to the above mentioned compounds having the following formula (II):

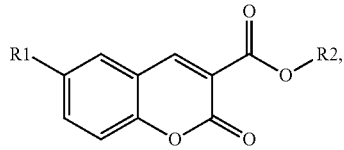
(II)

wherein
R1 represents —CH$_2$—Cl, —CH$_2$—Br, —CH$_2$—F, —CH$_2$OCOCH$_3$, —CH$_3$, —CH$_2$—NH$_2$, and its salts thereof, or H, and
R2 represents:
  an isoquinolinyl, or
  —CH$_3$, or
  a pyridyl, or
  a phenyl, substituted or not by a halogen,
  provided that
    if R1=H, R2 can only represent an isoquinolinyl, and
    if R1=CH$_3$, R2 can only represent a CH$_3$.

Compounds having the formula (II) and the significations for R1 and R2 noted above show an inhibitory activity against KLK5.

According to another embodiment, the present invention relates to the above mentioned compounds chosen among the group consisting of:

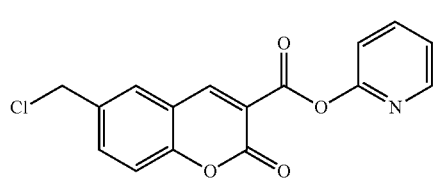
(LP12)

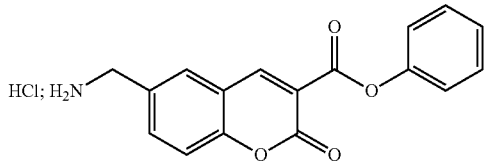
(LP71)

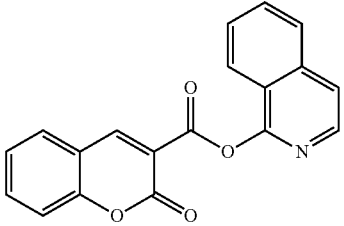
(CFL33)

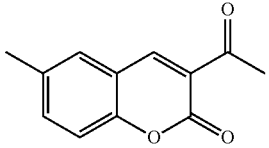
(D9)

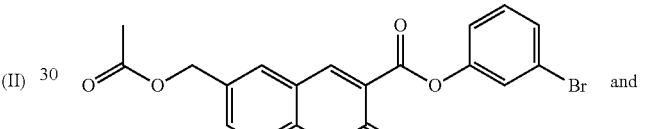
(IK9)

and

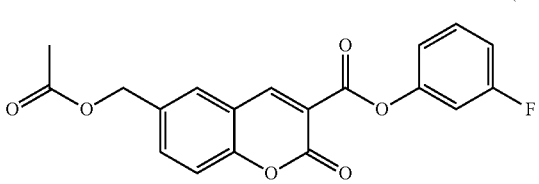
(IK10)

Compounds above show an inhibitory activity against KLK5.

According to another embodiment, the present invention relates to the above mentioned compounds chosen among the group consisting of:

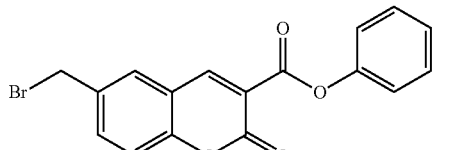
(JFR5)

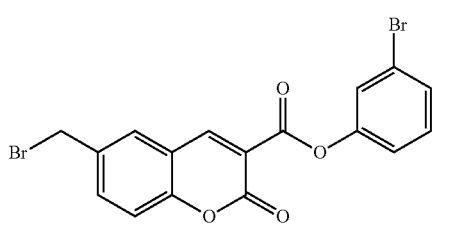
(JFR8)

-continued

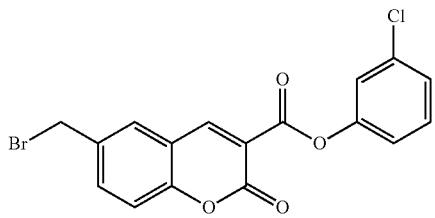
(JFR9)

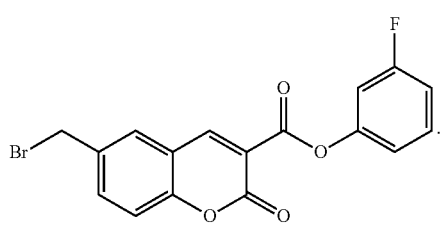
(JFR11)

Compounds above show an inhibitory activity against KLK5.

According to another embodiment, the present invention relates to the above mentioned compounds having the following formula (II):

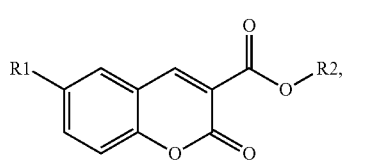
(II)

wherein
R1 represents —CH$_2$OCOC(CH$_3$)$_3$, —CH$_2$OCOCH$_3$ or —CH$_2$Cl, and
R2 represents a pyridyl or a phenyl, said pyridyl or phenyl being mono or bisubstituted by one or two groups chosen among a halogen, an amide, an acid, a —CH$_3$ or a —NO$_2$.

Compounds having the formula (II) and the significations for R1 and R2 noted above show an inhibitory activity against KLK14.

A test to show the inhibitory activity consists in incubating KLK14 and a coumarin derivative and then determining the activity of KLK14 by comparison of the initial rates to those obtained in control experiments, without coumarin derivative. The values of "IC50" (inhibitor concentrations giving 50% inhibition) express the inhibitory activity.

According to another embodiment, the present invention relates to the above mentioned compounds having the following formula (II):

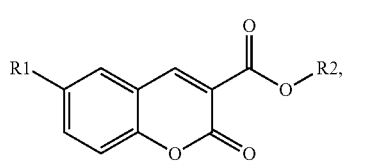
(II)

wherein
R1 represents —CH$_2$OCOC(CH$_3$)$_3$, —CH$_2$OCOCH$_3$ or —CH$_2$Cl, and
R2 represents a pyridyl or a phenyl, said pyridyl or phenyl being mono or bisubstituted by one or two groups chosen among a halogen, an amide, an acid, a —CH$_3$, a —NO$_2$ or a —CN.

Compounds having the formula (II) and the significations for R1 and R2 noted above show an inhibitory activity against KLK14.

According to another embodiment, the present invention relates to the above mentioned compounds having the following formula (II):

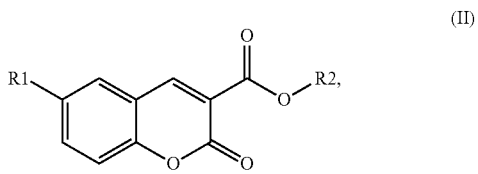
(II)

wherein
R1 represents —CH$_2$OCOC(CH$_3$)$_3$, —CH$_2$OCOCH$_3$, —CH$_2$Cl, —CH$_2$—Br or —CH$_2$—F, and
R2 represents a pyridyl or a phenyl, said pyridyl or phenyl being mono or bisubstituted by one or two groups chosen among a halogen, an amide, an acid, a —CH$_3$, a —NO$_2$ or a —CN, in particular by one halogen.

Compounds having the formula (II) and the significations for R1 and R2 noted above show an inhibitory activity against KLK14.

According to another embodiment, the present invention relates to the above mentioned compounds chosen among the group consisting of:

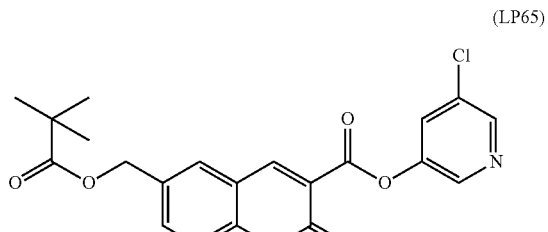
(LP65)

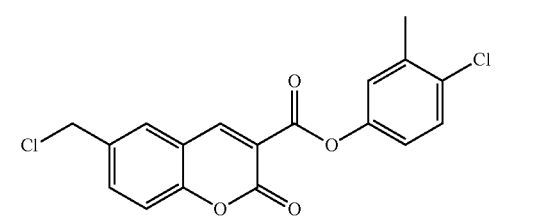
(MFS35)

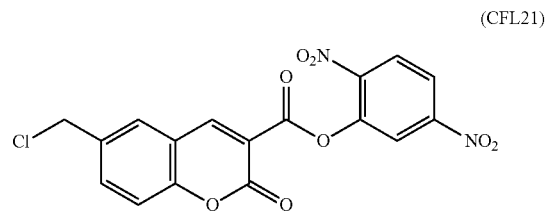
(CFL21)

(CFL17)

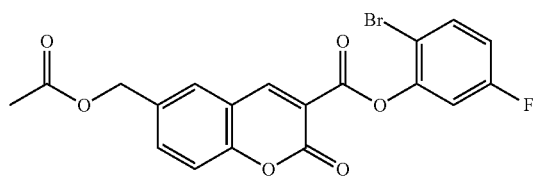

(IK3)

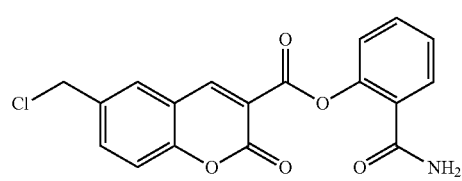
and (IK13)

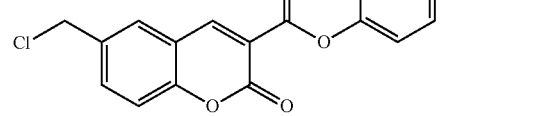

Compounds above show an inhibitory activity against KLK14.

According to another embodiment, the present invention relates to the above mentioned compound:

(SMB33)

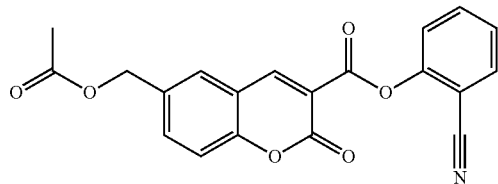

Compound above shows an inhibitory activity against KLK14.

According to another embodiment, the present invention relates to the above mentioned compounds chosen among the group consisting of:

(JFR5)

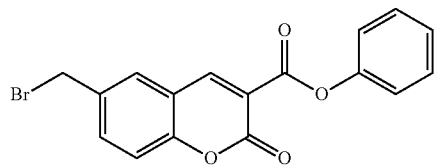

(JFR8)

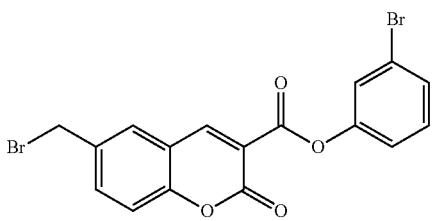

(JFR9)

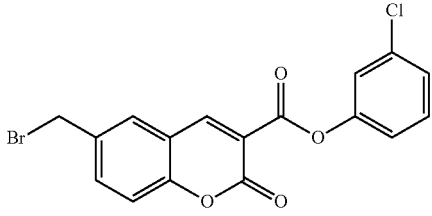

(JFR11)

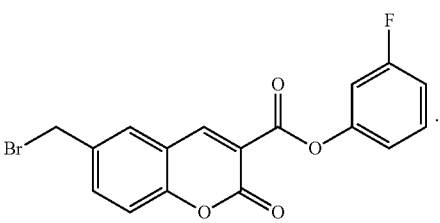

Compounds above show an inhibitory activity against KLK14.

According to another embodiment, the present invention relates to the above mentioned compounds having the following formula (Ib):

(Ib)

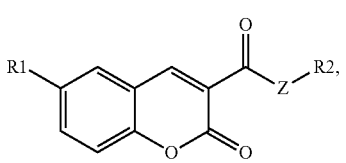

wherein

Z represents O or S,

R1 represents —CH$_2$Cl or —NH$_2$ or its salt thereof, and

R2 represents a pyridyl or a phenyl, said pyridyl or phenyl being substituted or not by one or two halogens, one amide or one ester.

According to another embodiment, the present invention relates to the above mentioned compounds having the following formula (Ib):

(Ib)

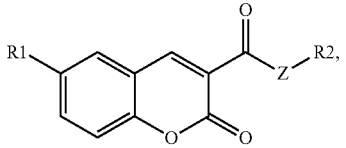

wherein

Z represents O or S,

R1 represents —CH$_2$Cl or —CH$_2$—NH$_2$ or its salt thereof, and

R2 represents a pyridyl or a phenyl, said pyridyl or phenyl being substituted or not by one or two halogens, one amide or one ester.

According to another embodiment, the present invention relates to the above mentioned compounds chosen among the group consisting of:

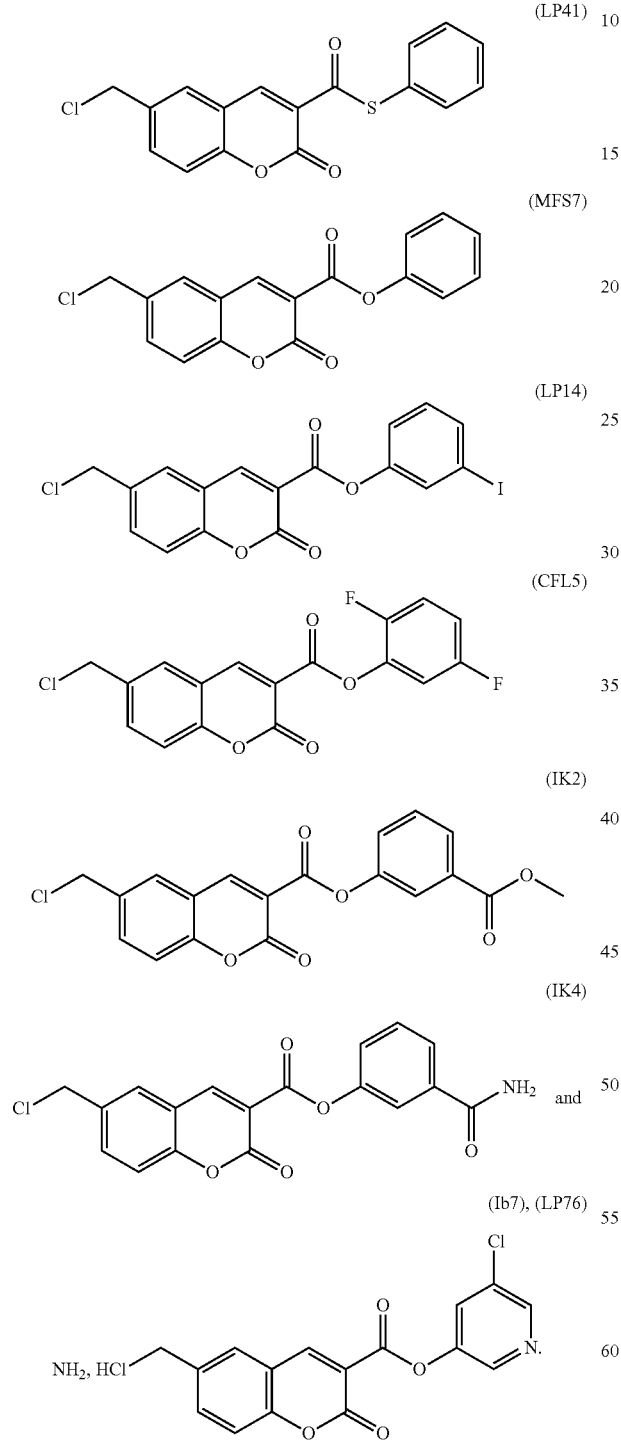

According to another embodiment, the present invention relates to compounds of formula (I-1) as presented below:

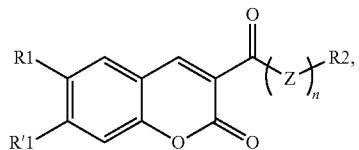

wherein n equals 0 or 1,
and wherein
  if n=1, Z represents O or S,
  R1 represents at least one group chosen among the group consisting of:
    hydrogen
    a linear or branched, saturated or not, C1-C7 alkyl, preferably a methyl group, substituted, or not, by a halogen chosen among Cl, F, I and Br,
    a linear or branched, saturated or not, C1-C7 alkyl, preferably a methyl group, substituted by a hydroxyl or a —O—R12 group, wherein R12 is a linear or branched, saturated or not, C1-C7 alkyl, preferably a hydroxyl,
    a group —CH$_2$—O—CO—R5, wherein R5 is chosen among a hydrogen atom, and a linear or branched, saturated or not, C1-C7 alkyl, substituted or not by at least one halogen chosen among Cl, F, I and Br,
    a group —O—R13, wherein R13 is chosen among hydrogen and a linear or branched, saturated or not, C1-C7 alkyl, R13 being preferably a hydrogen,
    an amine

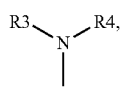

or a salt thereof, wherein R3 and R4, independently from each other, are chosen among hydrogen and a linear or branched, saturated or not, C1-C5 alkyl,
    a group

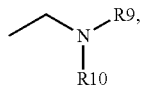

or a salt thereof, wherein R9 and R10, independently from each other, are chosen among:
    hydrogen,
    a linear or branched, saturated or not, C1-C5 alkyl,
    —CO—R5, wherein R5 is chosen among a hydrogen atom, and a linear or branched, saturated or not, C1-C7 alkyl, substituted or not by at least one halogen chosen among Cl, F, I and Br,
    —SO$_2$—R11, wherein R11 is a linear or branched, saturated or not, C1-C7 alkyl,
  R'1 represents a group chosen among hydrogen and —O—R14, wherein R14 is chosen among hydrogen and a linear or branched, saturated or not, C1-C7 alkyl, R14 being preferably a hydrogen, R'1 being preferably a hydrogen,
  provided that R'1 represents hydrogen when R1 does not represent a —O—R13 group, and R2 is chosen among the group consisting of:
- a linear or branched, saturated or not, C1-C7 alkyl, preferably a C1-C3 alkyl,
- a C3-C6 cycloalkyl, preferably a C4-C6 cycloalkyl, more preferably a cyclohexyl,
- an aryl group, preferably a phenyl group, possibly mono or polysubstituted, in particular disubstituted, by
  - a halogen chosen among Cl, F, I and Br, or
  - a linear or branched, saturated or not, C1-C7 alkyl, or
  - a group —CO—R6, R6 being chosen among the group consisting of: —OH, —NH$_2$, or salt thereof, and —O—R7, R7 being a linear or branched, saturated or not, C1-C7 alkyl, or
  - a group —O—R8, R8 being a linear or branched, saturated or not, C1-C7 alkyl, or
  - a group —NO$_2$,
  - a group —CN,
  - a combination of the above, and
- an heteroaryl group, preferably a pyridyl or an isoquinolinyl, possibly mono or polysubstituted, in particular disubstituted, by
  - a halogen chosen among Cl, F, I and Br, or
  - a linear or branched, saturated or not, C1-C7 alkyl, or
  - a group —CO—R6, R6 being chosen among the group consisting of: —OH, —NH$_2$, or salt thereof, and —O—R7, R7 being a linear or branched, saturated or not, C1-C7 alkyl, or
  - a group —O—R8, R8 being a linear or branched, saturated or not, C1-C7 alkyl, or
  - a combination of the above, provided that
when n=0, then R1 can only represent a linear or branched, saturated or not, C1-C7 alkyl, preferably a methyl group, possibly substituted by an halogen, such that
  if R1=CH$_3$ or CH$_2$—X, wherein X is an halogen, then R2 is a methyl group or a cycloalkyl group, preferably a cyclohexyl group,
when n=1,
  if R1=H, then R2 can only represent an isoquinolinyl or a phenyl substituted by two halogens, and
  if R1≠H, then if R2 is an aryl or an hetero aryl substituted by one linear or branched, saturated or not, C1-C7 alkyl, said aryl or heteroaryl is also substituted by at least another group different from a C1-C7 alkyl, for its use for the treatment of pathologies involving an excess of activity of at least one member of the kallikrein family, preferably belonging to the group consisting of KLK5, KLK7 and KLK14,
aforesaid pathologies belonging to the group consisting of Netherton syndrome, psoriasis, atopic eczema and allergic contact dermatitis.

According to another embodiment, the present invention relates to compounds of formula (I-1) as presented below:

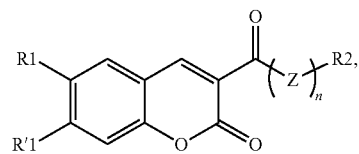

(I-1)

wherein n equals 0 or 1,
and wherein
  if n=1, Z represents O or S,
  R1 represents at least one group chosen among the group consisting of:
    hydrogen
    a linear or branched, saturated or not, C1-C7 alkyl, preferably a methyl group, substituted, or not, by a halogen chosen among Cl, F, I and Br,
    a linear or branched, saturated or not, C1-C7 alkyl, preferably a methyl group, substituted by a hydroxyl or a —O—R12 group, wherein R12 is a linear or branched, saturated or not, C1-C7 alkyl, preferably a hydroxyl,
    a group —CH$_2$—O—CO—R5, wherein R5 is chosen among a hydrogen atom, and a linear or branched, saturated or not, C1-C7 alkyl, substituted or not by at least one halogen chosen among Cl, F, I and Br,
    a group —O—R13, wherein R13 is chosen among hydrogen and a linear or branched, saturated or not, C1-C7 alkyl, R13 being preferably a hydrogen,
    an amine

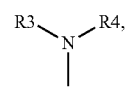

or a salt thereof, wherein R3 and R4, independently from each other, are chosen among hydrogen and a linear or branched, saturated or not, C1-C5 alkyl,
a group

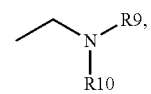

or a salt thereof, wherein R9 and R10, independently from each other, are chosen among:
  hydrogen,
  a linear or branched, saturated or not, C1-C5 alkyl,
  —CO—R5, wherein R5 is chosen among a hydrogen atom, and a linear or branched, saturated or not, C1-C7 alkyl, substituted or not by at least one halogen chosen among Cl, F, I and Br,
  —SO$_2$—R11, wherein R11 is a linear or branched, saturated or not, C1-C7 alkyl,
R'1 represents a group chosen among hydrogen and —O—R14, wherein R14 is chosen among hydrogen and a linear or branched, saturated or not, C1-C7 alkyl, R14 being preferably a hydrogen, R'1 being preferably a hydrogen,
provided that R'1 represents hydrogen when R1 does not represent a —O—R13 group, and R2 is chosen among the group consisting of:
- a linear or branched, saturated or not, C1-C7 alkyl, preferably a C1-C3 alkyl,
- a C3-C6 cycloalkyl, preferably a C4-C6 cycloalkyl, more preferably a cyclohexyl,
- an aryl group, preferably a phenyl or a naphthyl group, possibly mono or or polysubstituted, in particular disubstituted, by
  - a halogen chosen among Cl, F, I and Br, or
  - a linear or branched, saturated or not, C1-C7 alkyl, or
  - a group —CO—R6, R6 being chosen among the group consisting of: —OH, —NH$_2$, or salt thereof, and —O—R7, R7 being a linear or branched, saturated or not, C1-C7 alkyl, or
  - a group —O—R8, R8 being a linear or branched, saturated or not, C1-C7 alkyl, or
  - a group —NO$_2$,
  - a group —CN,
  - a combination of the above, and
- an heteroaryl group, preferably a pyridyl or an isoquinolinyl, possibly mono or polysubstituted, in particular disubstituted, by
  - a halogen chosen among Cl, F, I and Br, or
  - a linear or branched, saturated or not, C1-C7 alkyl, or
  - a group —CO—R6, R6 being chosen among the group consisting of: —OH, —NH$_2$, or salt thereof, and —O—R7, R7 being a linear or branched, saturated or not, C1-C7 alkyl, or
  - a group —O—R8, R8 being a linear or branched, saturated or not, C1-C7 alkyl, or
  - a combination of the above, provided that
when n=0, then R1 can only represent a linear or branched, saturated or not, C1-C7 alkyl, preferably a methyl group, possibly substituted by an halogen, such that
  if R1=CH$_3$ or CH$_2$—X, wherein X is an halogen, then R2 is a methyl group or a cycloalkyl group, preferably a cyclohexyl group,
when n=1,
  if R1=H, then R2 can only represent an isoquinolinyl or a naphthyl, or a phenyl substituted by two halogens, and
  if R1≠H, then if R2 is an aryl different from a naphthyl, or an hetero aryl, substituted by one linear or branched, saturated or not, C1-C7 alkyl, said aryl or heteroaryl is also substituted by at least another group, which is different from a C1-C7 alkyl,
for its use for the treatment of pathologies involving an excess of activity of at least one member of the kallikrein family, preferably belonging to the group consisting of KLK5, KLK7 and KLK14,
aforesaid pathologies belonging to the group consisting of Netherton syndrome, psoriasis, atopic eczema and allergic contact dermatitis.

According to another embodiment, the present invention relates to compounds of formula (I-1) as presented below:

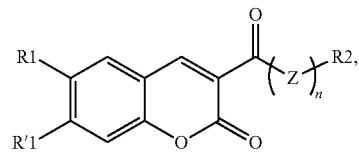

(I-1)

wherein n equals 0 or 1,
and wherein
  if n=1, Z represents O or S,
  R1 represents at least one group chosen among the group consisting of:
  - hydrogen
  - a linear or branched, saturated or not, C1-C7 alkyl, preferably a methyl group, substituted, or not, by a halogen chosen among Cl, F, I and Br,
  - a linear or branched, saturated or not, C1-C7 alkyl, preferably a methyl group, substituted by a hydroxyl or a —O—R12 group, wherein R12 is a linear or branched, saturated or not, C1-C7 alkyl, preferably a hydroxyl,
  - a group —CH$_2$—O—CO—R5, wherein R5 is chosen among a hydrogen atom, and a linear or branched, saturated or not, C1-C7 alkyl, substituted or not by at least one halogen chosen among Cl, F, I and Br,
  - a group —O—R13, wherein R13 is chosen among hydrogen and a linear or branched, saturated or not, C1-C7 alkyl, R13 being preferably a hydrogen,
  - an amine

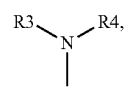

or a salt thereof, wherein R3 and R4, independently from each other, are chosen among hydrogen and a linear or branched, saturated or not, C1-C5 alkyl,
  - a group

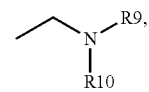

or a salt thereof, wherein R9 and R10, independently from each other, are chosen among:
  - hydrogen,
  - a linear or branched, saturated or not, C1-C5 alkyl,
  - —CO—R5, wherein R5 is chosen among a hydrogen atom, and a linear or branched, saturated or not, C1-C7 alkyl, substituted or not by at least one halogen chosen among Cl, F, I and Br,
  - —SO$_2$—R11, wherein R11 is a linear or branched, saturated or not, C1-C7 alkyl,
  R'1 represents a group chosen among hydrogen and —O—R14, wherein R14 is chosen among hydrogen and a linear or branched, saturated or not, C1-C7 alkyl, R14 being preferably a hydrogen, R'1 being preferably a hydrogen,
  provided that R'1 represents hydrogen when R1 does not represent a —O—R13 group, and
R2 is chosen among the group consisting of:
- a linear or branched, saturated or not, C1-C7 alkyl, preferably a C1-C3 alkyl,
- a C3-C6 cycloalkyl, preferably a C4-C6 cycloalkyl, more preferably a cyclohexyl,
- an aryl group, preferably a phenyl group, possibly mono or polysubstituted, in particular disubstituted, by
  - a halogen chosen among Cl, F, I and Br, or
  - a linear or branched, saturated or not, C1-C7 alkyl, or
  - a group —CO—R6, R6 being chosen among the group consisting of: —OH, —NH$_2$, or salt thereof, and —O—R7, R7 being a linear or branched, saturated or not, C1-C7 alkyl, or
  - a group —O—R8, R8 being a linear or branched, saturated or not, C1-C7 alkyl, or
  - a group —NO$_2$,
  - a group —CN,
  - a combination of the above,
  and
- an heteroaryl group, preferably a pyridyl or an isoquinolinyl, possibly mono or polysubstituted, in particular disubstituted, by
  - a halogen chosen among Cl, F, I and Br, or
  - a linear or branched, saturated or not, C1-C7 alkyl, or
  - a group —CO—R6, R6 being chosen among the group consisting of: —OH, —NH$_2$, or salt thereof, and —O—R7, R7 being a linear or branched, saturated or not, C1-C7 alkyl, or
  - a group —O—R8, R8 being a linear or branched, saturated or not, C1-C7 alkyl, or
  - a combination of the above, provided that
when n=0, then R1 can only represent a linear or branched, saturated or not, C1-C7 alkyl, preferably a methyl group, possibly substituted by an halogen, such that
  if R1=CH$_3$ or CH$_2$—X, wherein X is an halogen, then R2 is a methyl group or a cycloalkyl group, preferably a cyclohexyl group,
when n=1,
  if R1=H, then R2 can only represent an isoquinolinyl or a phenyl substituted by two halogens, and
  if R1≠H, then if R2 is an aryl or an hetero aryl substituted by one linear or branched, saturated or not, C1-C7 alkyl, said aryl or heteroaryl is also substituted by at least another group different from a C1-C7 alkyl,
for its use for the treatment of pathologies involving an excess of activity of at least one member of the kallikrein family, preferably belonging to the group consisting of KLK5, KLK7 and KLK14,
aforesaid pathologies being Netherton syndrome.

According to another embodiment, the present invention relates to compounds of formula (I-1) as presented below:

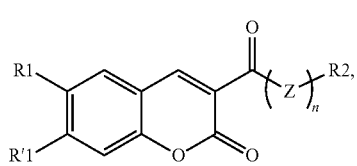

(I-1)

wherein n equals 0 or 1,
and wherein
if n=1, Z represents O or S,
R1 represents at least one group chosen among the group consisting of:
- hydrogen
- a linear or branched, saturated or not, C1-C7 alkyl, preferably a methyl group, substituted, or not, by a halogen chosen among Cl, F, I and Br,
- a linear or branched, saturated or not, C1-C7 alkyl, preferably a methyl group, substituted by a hydroxyl or a —O—R12 group, wherein R12 is a linear or branched, saturated or not, C1-C7 alkyl, preferably a hydroxyl,
- a group —CH$_2$—O—CO—R5, wherein R5 is chosen among a hydrogen atom, and a linear or branched, saturated or not, C1-C7 alkyl, substituted or not by at least one halogen chosen among Cl, F, I and Br,
- a group —O—R13, wherein R13 is chosen among hydrogen and a linear or branched, saturated or not, C1-C7 alkyl, R13 being preferably a hydrogen,
- an amine

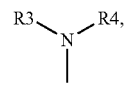

or a salt thereof, wherein R3 and R4, independently from each other, are chosen among hydrogen and a linear or branched, saturated or not, C1-C5 alkyl,
- a group

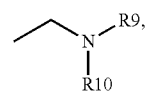

or a salt thereof, wherein R9 and R10, independently from each other, are chosen among:
- hydrogen,
- a linear or branched, saturated or not, C1-C5 alkyl,
- —CO—R5, wherein R5 is chosen among a hydrogen atom, and a linear or branched, saturated or not, C1-C7 alkyl, substituted or not by at least one halogen chosen among Cl, F, I and Br,
- —SO$_2$—R11, wherein R11 is a linear or branched, saturated or not, C1-C7 alkyl, R'1 represents a group chosen among hydrogen and —O—R14, wherein R14 is chosen among hydrogen and a linear or branched, saturated or not, C1-C7 alkyl, R14 being preferably a hydrogen, R'1 being preferably a hydrogen,
provided that R'1 represents hydrogen when R1 does not represent a —O—R13 group,
and
R2 is chosen among the group consisting of:
- a linear or branched, saturated or not, C1-C7 alkyl, preferably a C1-C3 alkyl,
- a C3-C6 cycloalkyl, preferably a C4-C6 cycloalkyl, more preferably a cyclohexyl,
- an aryl group, preferably a phenyl or a naphthyl group, possibly mono or or polysubstituted, in particular disubstituted, by a halogen chosen among Cl, F, I and Br, or
a linear or branched, saturated or not, C1-C7 alkyl, or
a group —CO—R6, R6 being chosen among the group consisting of: —OH, —NH$_2$, or salt thereof, and —O—R7, R7 being a linear or branched, saturated or not, C1-C7 alkyl, or
a group —O—R8, R8 being a linear or branched, saturated or not, C1-C7 alkyl, or
a group —NO$_2$,
a group —CN,
a combination of the above,
and
an heteroaryl group, preferably a pyridyl or an isoquinolinyl, possibly mono or polysubstituted, in particular disubstituted, by
a halogen chosen among Cl, F, I and Br, or
a linear or branched, saturated or not, C1-C7 alkyl, or
a group —CO—R6, R6 being chosen among the group consisting of: —OH, —NH$_2$, or salt thereof, and —O—R7, R7 being a linear or branched, saturated or not, C1-C7 alkyl, or
a group —O—R8, R8 being a linear or branched, saturated or not, C1-C7 alkyl, or
a combination of the above,
provided that
when n=0, then R1 can only represent a linear or branched, saturated or not, C1-C7 alkyl, preferably a methyl group, possibly substituted by an halogen, such that
if R1=CH$_3$ or CH$_2$—X, wherein X is an halogen, then R2 is a methyl group or a cycloalkyl group, preferably a cyclohexyl group,
when n=1,
if R1=H, then R2 can only represent an isoquinolinyl or a naphthyl, or a phenyl substituted by two halogens, and
if R1≠H, then if R2 is an aryl different from a naphthyl, or an hetero aryl, substituted by one linear or branched, saturated or not, C1-C7 alkyl, said aryl or heteroaryl is also substituted by at least another group, which is different from a C1-C7 alkyl,
for its use for the treatment of pathologies involving an excess of activity of at least one member of the kallikrein family, preferably belonging to the group consisting of KLK5, KLK7 and KLK14,
aforesaid pathologies being Netherton syndrome.

According to another embodiment, the present invention relates to compounds of formula (I-1) as presented below:

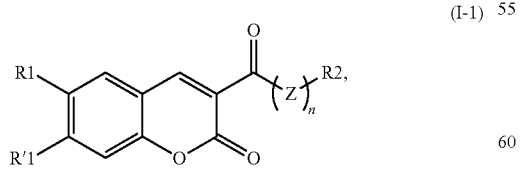

(I-1)

wherein n equals 0 or 1,
and wherein
if n=1, Z represents O or S,
R1 represents at least one group chosen among the group consisting of:
hydrogen
a linear or branched, saturated or not, C1-C7 alkyl, preferably a methyl group, substituted, or not, by a halogen chosen among Cl, F, I and Br,
a linear or branched, saturated or not, C1-C7 alkyl, preferably a methyl group, substituted by a hydroxyl or a —O—R12 group, wherein R12 is a linear or branched, saturated or not, C1-C7 alkyl, preferably a hydroxyl,
a group —CH$_2$—O—CO—R5, wherein R5 is chosen among a hydrogen atom, and a linear or branched, saturated or not, C1-C7 alkyl, substituted or not by at least one halogen chosen among Cl, F, I and Br,
a group —O—R13, wherein R13 is chosen among hydrogen and a linear or branched, saturated or not, C1-C7 alkyl, R13 being preferably a hydrogen,
an amine

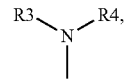

or a salt thereof, wherein R3 and R4, independently from each other, are chosen among hydrogen and a linear or branched, saturated or not, C1-C5 alkyl,
a group

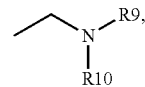

or a salt thereof, wherein R9 and R10, independently from each other, are chosen among:
hydrogen,
a linear or branched, saturated or not, C1-C5 alkyl,
—CO—R5, wherein R5 is chosen among a hydrogen atom, and a linear or branched, saturated or not, C1-C7 alkyl, substituted or not by at least one halogen chosen among Cl, F, I and Br,
—SO$_2$—R11, wherein R11 is a linear or branched, saturated or not, C1-C7 alkyl,
R'1 represents a group chosen among hydrogen and —O—R14, wherein R14 is chosen among hydrogen and a linear or branched, saturated or not, C1-C7 alkyl, R14 being preferably a hydrogen, R'1 being preferably a hydrogen,
provided that R'1 represents hydrogen when R1 does not represent a —O—R13 group,
and
R2 is chosen among the group consisting of:
a linear or branched, saturated or not, C1-C7 alkyl, preferably a C1-C3 alkyl,
a C3-C6 cycloalkyl, preferably a C4-C6 cycloalkyl, more preferably a cyclohexyl,
an aryl group, preferably a phenyl group, possibly mono or polysubstituted, in particular disubstituted, by
a halogen chosen among Cl, F, I and Br, or
a linear or branched, saturated or not, C1-C7 alkyl, or
a group —CO—R6, R6 being chosen among the group consisting of: —OH, —NH$_2$, or salt thereof, and —O—R7, R7 being a linear or branched, saturated or not, C1-C7 alkyl, or a group —O—R8, R8 being a linear or branched, saturated or not, C1-C7 alkyl, or
a group —NO$_2$,
a group —CN,
a combination of the above,
and
an heteroaryl group, preferably a pyridyl or an isoquinolinyl, possibly mono or polysubstituted, in particular disubstituted, by
a halogen chosen among Cl, F, I and Br, or
a linear or branched, saturated or not, C1-C7 alkyl, or
a group —CO—R6, R6 being chosen among the group consisting of: —OH, —NH$_2$, or salt thereof, and —O—R7, R7 being a linear or branched, saturated or not, C1-C7 alkyl, or
a group —O—R8, R8 being a linear or branched, saturated or not, C1-C7 alkyl, or
a combination of the above,
provided that
when n=0, then R1 can only represent a linear or branched, saturated or not, C1-C7 alkyl, preferably a methyl group, possibly substituted by an halogen, such that
if R1=CH$_3$ or CH$_2$—X, wherein X is an halogen, then R2 is a methyl group or a cycloalkyl group, preferably a cyclohexyl group,
when n=1,
if R1=H, then R2 can only represent an isoquinolinyl or a phenyl substituted by two halogens, and
if R1≠H, then if R2 is an aryl or an hetero aryl substituted by one linear or branched, saturated or not, C1-C7 alkyl, said aryl or heteroaryl is also substituted by at least another group different from a C1-C7 alkyl,
for its use for the treatment of pathologies involving an excess of activity of at least one member of the kallikrein family, preferably belonging to the group consisting of KLK5, KLK7 and KLK14,
aforesaid pathologies belonging to the group consisting of psoriasis, atopic eczema and allergic contact dermatitis.

According to another embodiment, the present invention relates to compounds of formula (I-1) as presented below:

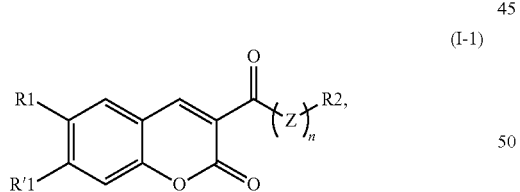

(I-1)

wherein n equals 0 or 1,
and wherein
if n=1, Z represents O or S,
R1 represents at least one group chosen among the group consisting of:
hydrogen
a linear or branched, saturated or not, C1-C7 alkyl, preferably a methyl group, substituted, or not, by a halogen chosen among Cl, F, I and Br,
a linear or branched, saturated or not, C1-C7 alkyl, preferably a methyl group, substituted by a hydroxyl or a —O—R12 group, wherein R12 is a linear or branched, saturated or not, C1-C7 alkyl, preferably a hydroxyl,
a group —CH$_2$—O—CO—R5, wherein R5 is chosen among a hydrogen atom, and a linear or branched, saturated or not, C1-C7 alkyl, substituted or not by at least one halogen chosen among Cl, F, I and Br,
a group —O—R13, wherein R13 is chosen among hydrogen and a linear or branched, saturated or not, C1-C7 alkyl, R13 being preferably a hydrogen,
an amine

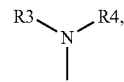

or a salt thereof, wherein R3 and R4, independently from each other, are chosen among hydrogen and a linear or branched, saturated or not, C1-C5 alkyl,
a group

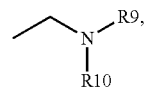

or a salt thereof, wherein R9 and R10, independently from each other, are chosen among:
hydrogen,
a linear or branched, saturated or not, C1-C5 alkyl,
—CO—R5, wherein R5 is chosen among a hydrogen atom, and a linear or branched, saturated or not, C1-C7 alkyl, substituted or not by at least one halogen chosen among Cl, F, I and Br,
—SO$_2$—R11, wherein R11 is a linear or branched, saturated or not, C1-C7 alkyl,
R'1 represents a group chosen among hydrogen and —O—R14, wherein R14 is chosen among hydrogen and a linear or branched, saturated or not, C1-C7 alkyl, R14 being preferably a hydrogen, R'1 being preferably a hydrogen,
provided that R'1 represents hydrogen when R1 does not represent a —O—R13 group,
and
R2 is chosen among the group consisting of:
a linear or branched, saturated or not, C1-C7 alkyl, preferably a C1-C3 alkyl,
a C3-C6 cycloalkyl, preferably a C4-C6 cycloalkyl, more preferably a cyclohexyl,
an aryl group, preferably a phenyl or a naphthyl group, possibly mono or or polysubstituted, in particular disubstituted, by
a halogen chosen among Cl, F, I and Br, or
a linear or branched, saturated or not, C1-C7 alkyl, or
a group —CO—R6, R6 being chosen among the group consisting of: —OH, —NH$_2$, or salt thereof, and —O—R7, R7 being a linear or branched, saturated or not, C1-C7 alkyl, or
a group —O—R8, R8 being a linear or branched, saturated or not, C1-C7 alkyl, or
a group —NO$_2$,
a group —CN,
a combination of the above,
and
an heteroaryl group, preferably a pyridyl or an isoquinolinyl, possibly mono or polysubstituted, in particular disubstituted, by a halogen chosen among Cl, F, I and Br, or
a linear or branched, saturated or not, C1-C7 alkyl, or
a group —CO—R6, R6 being chosen among the group consisting of: —OH, —NH$_2$, or salt thereof, and —O—R7, R7 being a linear or branched, saturated or not, C1-C7 alkyl, or
a group —O—R8, R8 being a linear or branched, saturated or not, C1-C7 alkyl, or
a combination of the above,
provided that
when n=0, then R1 can only represent a linear or branched, saturated or not, C1-C7 alkyl, preferably a methyl group, possibly substituted by an halogen, such that
if R1=CH$_3$ or CH$_2$—X, wherein X is an halogen, then R2 is a methyl group or a cycloalkyl group, preferably a cyclohexyl group,
when n=1,
if R1=H, then R2 can only represent an isoquinolinyl or a naphthyl, or a phenyl substituted by two halogens, and
if R1≠H, then if R2 is an aryl different from a naphthyl, or an hetero aryl, substituted by one linear or branched, saturated or not, C1-C7 alkyl, said aryl or heteroaryl is also substituted by at least another group, which is different from a C1-C7 alkyl,
for its use for the treatment of pathologies involving an excess of activity of at least one member of the kallikrein family, preferably belonging to the group consisting of KLK5, KLK7 and KLK14,
aforesaid pathologies belonging to the group consisting of psoriasis, atopic eczema and allergic contact dermatitis.

According to another embodiment, the present invention relates to compounds of formula (I-1b) as presented below:

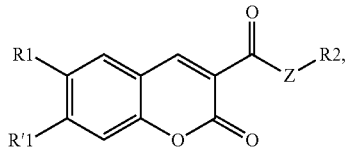
(I-1b)

wherein
Z represents O or S,
R1 represents at least one group chosen among the group consisting of:
a linear or branched, saturated or not, C1-C7 alkyl, preferably a methyl group, substituted by a hydroxyl or a —O—R12 group, wherein R12 is a linear or branched, saturated or not, C1-C7 alkyl, preferably a hydroxyl,
a group —O—R13, wherein R13 is chosen among hydrogen and a linear or branched, saturated or not, C1-C7 alkyl, R13 being preferably a hydrogen,
an amine

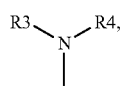

or a salt thereof, wherein R3 and R4, independently from each other, are chosen among hydrogen and a linear or branched, saturated or not, C1-C5 alkyl, a group

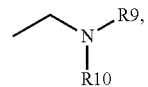

or a salt thereof, wherein R9 and R10, independently from each other, are chosen among:
hydrogen,
a linear or branched, saturated or not, C1-C5 alkyl,
—CO—R5, wherein R5 is chosen among a hydrogen atom, and a linear or branched, saturated or not, C1-C7 alkyl, substituted or not by at least one halogen chosen among Cl, F, I and Br,
—SO$_2$—R11, wherein R11 is a linear or branched, saturated or not, C1-C7 alkyl,
R'1 represents a group chosen among hydrogen and —O—R14, wherein R14 is chosen among hydrogen and a linear or branched, saturated or not, C1-C7 alkyl, R14 being preferably a hydrogen, R'1 being preferably a hydrogen,
provided that R'1 represents hydrogen when R1 does not represent a —O—R13 group,
and
R2 is chosen among the group consisting of:
a linear or branched, saturated or not, C1-C7 alkyl, preferably a C1-C3 alkyl,
a C3-C6 cycloalkyl, preferably a C4-C6 cycloalkyl, more preferably a cyclohexyl,
an aryl group, preferably a phenyl group, possibly mono or polysubstituted, in particular disubstituted, by
a halogen chosen among Cl, F, I and Br, or
a linear or branched, saturated or not, C1-C7 alkyl, or
a group —CO—R6, R6 being chosen among the group consisting of: —OH, —NH$_2$, or salt thereof, and —O—R7, R7 being a linear or branched, saturated or not, C1-C7 alkyl, or
a group —O—R8, R8 being a linear or branched, saturated or not, C1-C7 alkyl, or
a group —NO$_2$,
a group —CN,
a combination of the above,
and
an heteroaryl group, preferably a pyridyl or an isoquinolinyl, possibly mono or polysubstituted, in particular disubstituted, by
a halogen chosen among Cl, F, I and Br, or
a linear or branched, saturated or not, C1-C7 alkyl, or
a group —CO—R6, R6 being chosen among the group consisting of: —OH, —NH$_2$, or salt thereof, and —O—R7, R7 being a linear or branched, saturated or not, C1-C7 alkyl, or
a group —O—R8, R8 being a linear or branched, saturated or not, C1-C7 alkyl, or
a combination of the above,
provided that:
if R2 is an aryl or an hetero aryl substituted by one a linear or branched, saturated or not, C1-C7 alkyl, said aryl or heteroaryl is also substituted by at least another group different from a C1-C7 alkyl,
if R1 represents a group

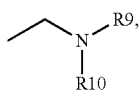

wherein R9 and R10 are independently chosen among hydrogen and a linear or branched, saturated or not, C1-C5 alkyl, or a salt thereof, R2 is different from a pyridyl, and represents in particular a phenyl, for its use for the treatment of pathologies involving an excess of activity of at least one member of the kallikrein family, preferably belonging to the group consisting of KLK5, KLK7 and KLK14, aforesaid pathologies belonging to the group consisting of psoriasis, atopic eczema and allergic contact dermatitis.

According to another embodiment, the present invention relates to compounds of formula (I-1b) as presented below:

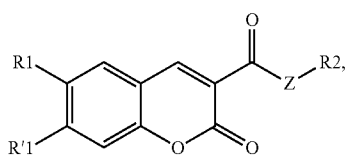

(I-1b)

wherein
Z represents O or S,
R1 represents at least one group chosen among the group consisting of:
  a linear or branched, saturated or not, C1-C7 alkyl, preferably a methyl group, substituted by a hydroxyl or a —O—R12 group, wherein R12 is a linear or branched, saturated or not, C1-C7 alkyl, preferably a hydroxyl,
  a group —O—R13, wherein R13 is chosen among hydrogen and a linear or branched, saturated or not, C1-C7 alkyl, R13 being preferably a hydrogen,
  an amine

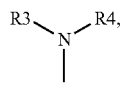

or a salt thereof, wherein R3 and R4, independently from each other, are chosen among hydrogen and a linear or branched, saturated or not, C1-C5 alkyl,
a group

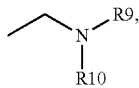

or a salt thereof, wherein R9 and R10, independently from each other, are chosen among:
hydrogen,
a linear or branched, saturated or not, C1-C5 alkyl,
—CO—R5, wherein R5 is chosen among a hydrogen atom, and a linear or branched, saturated or not, C1-C7 alkyl, substituted or not by at least one halogen chosen among Cl, F, I and Br,
—SO₂—R11, wherein R11 is a linear or branched, saturated or not, C1-C7 alkyl,
R'1 represents a group chosen among hydrogen and —O—R14, wherein R14 is chosen among hydrogen and a linear or branched, saturated or not, C1-C7 alkyl, R14 being preferably a hydrogen, R'1 being preferably a hydrogen,
provided that R'1 represents hydrogen when R1 does not represent a —O—R13 group,
and
R2 is chosen among the group consisting of:
  a linear or branched, saturated or not, C1-C7 alkyl, preferably a C1-C3 alkyl,
  a C3-C6 cycloalkyl, preferably a C4-C6 cycloalkyl, more preferably a cyclohexyl,
  an aryl group, preferably a phenyl or a naphthyl group, possibly mono or or polysubstituted, in particular disubstituted, by
    a halogen chosen among Cl, F, I and Br, or
    a linear or branched, saturated or not, C1-C7 alkyl, or
    a group —CO—R6, R6 being chosen among the group consisting of: —OH, —NH₂, or salt thereof, and —O—R7, R7 being a linear or branched, saturated or not, C1-C7 alkyl, or
    a group —O—R8, R8 being a linear or branched, saturated or not, C1-C7 alkyl, or
    a group —NO₂,
    a group —CN,
    a combination of the above,
and
  an heteroaryl group, preferably a pyridyl or an isoquinolinyl, possibly mono or polysubstituted, in particular disubstituted, by
    a halogen chosen among Cl, F, I and Br, or
    a linear or branched, saturated or not, C1-C7 alkyl, or
    a group —CO—R6, R6 being chosen among the group consisting of: —OH, —NH₂, or salt thereof, and —O—R7, R7 being a linear or branched, saturated or not, C1-C7 alkyl, or
    a group —O—R8, R8 being a linear or branched, saturated or not, C1-C7 alkyl, or
    a combination of the above,
provided that:
  if R2 is an aryl different from a naphthyl, or an hetero aryl, substituted by one a linear or branched, saturated or not, C1-C7 alkyl, said aryl or heteroaryl is also substituted by at least another group different from a C1-C7 alkyl,
  if R1 represents a group

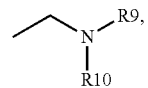

wherein R9 and R10 are independently chosen among hydrogen and a linear or branched, saturated or not, C1-C5 alkyl, or a salt thereof, R2 is different from a pyridyl, and represents in particular a phenyl, for its use for the treatment of pathologies involving an excess of activity of at least one member of the kallikrein family, preferably belonging to the group consisting of KLK5, KLK7 and KLK14, aforesaid pathologies belonging to the group consisting of psoriasis, atopic eczema and allergic contact dermatitis.

According to another embodiment, the present invention relates to compounds of formula (Ib) as presented below:

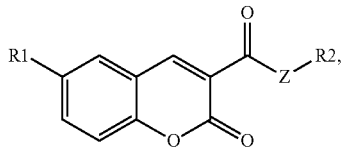

(Ib)

wherein
Z represents O or S,
R1 represents a group

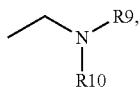

or a salt thereof, wherein R9 and R10, independently from each other, are chosen among:
hydrogen,
a linear or branched, saturated or not, C1-C5 alkyl,
and
R2 is a phenyl group, possibly mono or polysubstituted, in particular disubstituted, by
a halogen chosen among Cl, F, I and Br, or
a linear or branched, saturated or not, C1-C7 alkyl, or
a group —CO—R6, R6 being chosen among the group consisting of: —OH, —NH$_2$, or salt thereof, and —O—R7, R7 being a linear or branched, saturated or not, C1-C7 alkyl, or
a group —O—R8, R8 being a linear or branched, saturated or not, C1-C7 alkyl, or
a group —NO$_2$,
a group —CN,
a combination of the above,
provided that:
if R2 is substituted by one a linear or branched, saturated or not, C1-C7 alkyl, R2 is substituted by at least another group different from a C1-C7 alkyl,
for its use for the treatment of pathologies involving an excess of activity of at least one member of the kallikrein family, preferably belonging to the group consisting of KLK5, KLK7 and KLK14,
aforesaid pathologies belonging to the group consisting of psoriasis, atopic eczema and allergic contact dermatitis.

According to another embodiment, the present invention relates to compounds of formula (Ib) as presented below:

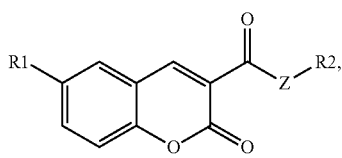

(Ib)

wherein
Z represents O or S,
R1 represents a group

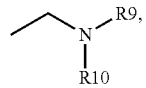

or a salt thereof, wherein R9 and R10, independently from each other, are chosen among:
hydrogen,
a linear or branched, saturated or not, C1-C5 alkyl,
—CO—R5, wherein R5 is chosen among a hydrogen atom, and a linear or branched, saturated or not, C1-C7 alkyl, substituted or not by at least one halogen chosen among Cl, F, I and Br,
at least one of R9 and R10 representing —CO—R5,
and
R2 is chosen among the group consisting of:
a linear or branched, saturated or not, C1-C7 alkyl, preferably a C1-C3 alkyl,
a C3-C6 cycloalkyl, preferably a C4-C6 cycloalkyl, more preferably a cyclohexyl,
an aryl group, preferably a phenyl group, possibly mono or polysubstituted, in particular disubstituted, by
a halogen chosen among Cl, F, I and Br, or
a linear or branched, saturated or not, C1-C7 alkyl, or
a group —CO—R6, R6 being chosen among the group consisting of: —OH, —NH$_2$, or salt thereof, and —O—R7, R7 being a linear or branched, saturated or not, C1-C7 alkyl, or
a group —O—R8, R8 being a linear or branched, saturated or not, C1-C7 alkyl, or
a group —NO$_2$,
a group —CN,
a combination of the above,
and
an heteroaryl group, preferably a pyridyl or an isoquinolinyl, possibly mono or polysubstituted, in particular disubstituted, by
a halogen chosen among Cl, F, I and Br, or
a linear or branched, saturated or not, C1-C7 alkyl, or
a group —CO—R6, R6 being chosen among the group consisting of: —OH, —NH$_2$, or salt thereof, and —O—R7, R7 being a linear or branched, saturated or not, C1-C7 alkyl, or
a group —O—R8, R8 being a linear or branched, saturated or not, C1-C7 alkyl, or
a combination of the above,
provided that:
if R2 is an aryl or an hetero aryl substituted by one a linear or branched, saturated or not, C1-C7 alkyl, said aryl or heteroaryl is also substituted by at least another group different from a C1-C7 alkyl,
for its use for the treatment of pathologies involving an excess of activity of at least one member of the kallikrein family, preferably belonging to the group consisting of KLK5, KLK7 and KLK14,
aforesaid pathologies belonging to the group consisting of psoriasis, atopic eczema and allergic contact dermatitis.

According to another embodiment, the present invention relates to compounds of formula (Ib) as presented below:

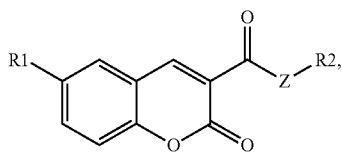

wherein
Z represents O or S,
R1 represents a group

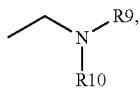

or a salt thereof, wherein R9 and R10, independently from each other, are chosen among:
hydrogen,
a linear or branched, saturated or not, C1-C5 alkyl,
—SO₂—R11, wherein R11 is a linear or branched, saturated or not, C1-C7 alkyl,
at least one of R9 and R10 representing —SO₂—R11,
and
R2 is chosen among the group consisting of:
a linear or branched, saturated or not, C1-C7 alkyl, preferably a C1-C3 alkyl,
a C3-C6 cycloalkyl, preferably a C4-C6 cycloalkyl, more preferably a cyclohexyl,
an aryl group, preferably a phenyl group, possibly mono or polysubstituted, in particular disubstituted, by
a halogen chosen among Cl, F, I and Br, or
a linear or branched, saturated or not, C1-C7 alkyl, or
a group —CO—R6, R6 being chosen among the group consisting of: —OH, —NH₂, or salt thereof, and —O—R7, R7 being a linear or branched, saturated or not, C1-C7 alkyl, or
a group —O—R8, R8 being a linear or branched, saturated or not, C1-C7 alkyl, or
a group —NO₂,
a group —CN,
a combination of the above,
and
an heteroaryl group, preferably a pyridyl or an isoquinolinyl, possibly mono or polysubstituted, in particular disubstituted, by
a halogen chosen among Cl, F, I and Br, or
a linear or branched, saturated or not, C1-C7 alkyl, or
a group —CO—R6, R6 being chosen among the group consisting of: —OH, —NH₂, or salt thereof, and —O—R7, R7 being a linear or branched, saturated or not, C1-C7 alkyl, or
a group —O—R8, R8 being a linear or branched, saturated or not, C1-C7 alkyl, or
a combination of the above,
provided that:
if R2 is an aryl or an hetero aryl substituted by one a linear or branched, saturated or not, C1-C7 alkyl, said aryl or heteroaryl is also substituted by at least another group different from a C1-C7 alkyl,
for its use for the treatment of pathologies involving an excess of activity of at least one member of the kallikrein family, preferably belonging to the group consisting of KLK5, KLK7 and KLK14,
aforesaid pathologies belonging to the group consisting of psoriasis, atopic eczema and allergic contact dermatitis.

According to another embodiment, the present invention relates to compounds of formula (Ib) as presented below:

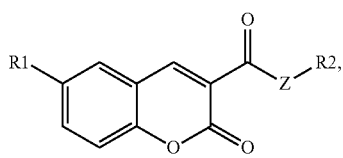

wherein
Z represents O or S,
R1 represents a linear or branched, saturated or not, C1-C7 alkyl, preferably a methyl group, substituted by a hydroxyl or a —O—R12 group, wherein R12 is a linear or branched, saturated or not, C1-C7 alkyl, preferably a hydroxyl, and
R2 is chosen among the group consisting of:
a linear or branched, saturated or not, C1-C7 alkyl, preferably a C1-C3 alkyl,
a C3-C6 cycloalkyl, preferably a C4-C6 cycloalkyl, more preferably a cyclohexyl,
an aryl group, preferably a phenyl group, possibly mono or polysubstituted, in particular disubstituted, by
a halogen chosen among Cl, F, I and Br, or
a linear or branched, saturated or not, C1-C7 alkyl, or
a group —CO—R6, R6 being chosen among the group consisting of: —OH, —NH₂, or salt thereof, and —O—R7, R7 being a linear or branched, saturated or not, C1-C7 alkyl, or
a group —O—R8, R8 being a linear or branched, saturated or not, C1-C7 alkyl, or
a group —NO₂,
a group —CN,
a combination of the above,
and
an heteroaryl group, preferably a pyridyl or an isoquinolinyl, possibly mono or polysubstituted, in particular disubstituted, by
a halogen chosen among Cl, F, I and Br, or
a linear or branched, saturated or not, C1-C7 alkyl, or
a group —CO—R6, R6 being chosen among the group consisting of: —OH, —NH₂, or salt thereof, and —O—R7, R7 being a linear or branched, saturated or not, C1-C7 alkyl, or
a group —O—R8, R8 being a linear or branched, saturated or not, C1-C7 alkyl, or
a combination of the above,
provided that:
if R2 is an aryl or an hetero aryl substituted by one a linear or branched, saturated or not, C1-C7 alkyl, said aryl or heteroaryl is also substituted by at least another group different from a C1-C7 alkyl,
for its use for the treatment of pathologies involving an excess of activity of at least one member of the kallikrein family, preferably belonging to the group consisting of KLK5, KLK7 and KLK14, aforesaid pathologies belonging to the group consisting of psoriasis, atopic eczema and allergic contact dermatitis.

According to another embodiment, the present invention relates to compounds of formula (Ib) as presented below:

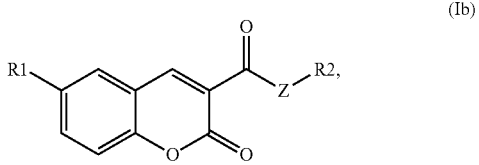

(Ib)

wherein
Z represents O or S,
R1 represents an amine

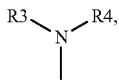

or a salt thereof, wherein R3 and R4, independently from each other, are chosen among hydrogen and a linear or branched, saturated or not, C1-C5 alkyl,
and
R2 is chosen among the group consisting of:
  a linear or branched, saturated or not, C1-C7 alkyl, preferably a C1-C3 alkyl,
  a C3-C6 cycloalkyl, preferably a C4-C6 cycloalkyl, more preferably a cyclohexyl,
  an aryl group, preferably a phenyl group, possibly mono or polysubstituted, in particular disubstituted, by
    a halogen chosen among Cl, F, I and Br, or
    a linear or branched, saturated or not, C1-C7 alkyl, or
    a group —CO—R6, R6 being chosen among the group consisting of: —OH, —NH$_2$, or salt thereof, and —O—R7, R7 being a linear or branched, saturated or not, C1-C7 alkyl, or
    a group —O—R8, R8 being a linear or branched, saturated or not, C1-C7 alkyl, or
    a group —NO$_2$,
    a group —CN,
    a combination of the above,
  and
  an heteroaryl group, preferably a pyridyl or an isoquinolinyl, possibly mono or polysubstituted, in particular disubstituted, by
    a halogen chosen among Cl, F, I and Br, or
    a linear or branched, saturated or not, C1-C7 alkyl, or
    a group —CO—R6, R6 being chosen among the group consisting of: —OH, —NH$_2$, or salt thereof, and —O—R7, R7 being a linear or branched, saturated or not, C1-C7 alkyl, or
    a group —O—R8, R8 being a linear or branched, saturated or not, C1-C7 alkyl, or
    a combination of the above,
  provided that:
    if R2 is an aryl or an hetero aryl substituted by one a linear or branched, saturated or not, C1-C7 alkyl, said aryl or heteroaryl is also substituted by at least another group different from a C1-C7 alkyl, for its use for the treatment of pathologies involving an excess of activity of at least one member of the kallikrein family, preferably belonging to the group consisting of KLK5, KLK7 and KLK14,
aforesaid pathologies belonging to the group consisting of psoriasis, atopic eczema and allergic contact dermatitis.

According to another embodiment, the present invention relates to compounds of formula (I-1b) as presented below:

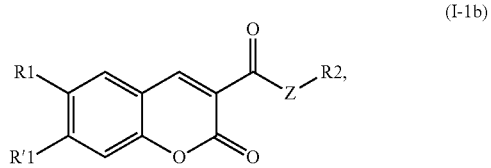

(I-1b)

wherein
Z represents O or S,
R1 represents a group —O—R13, wherein R13 is chosen among hydrogen and a linear or branched, saturated or not, C1-C7 alkyl, R13 being preferably a hydrogen,
R'1 represents a group chosen among hydrogen and —O—R14, wherein R14 is chosen among hydrogen and a linear or branched, saturated or not, C1-C7 alkyl, R14 being preferably a hydrogen, R'1 being preferably a hydrogen,
R2 is chosen among the group consisting of:
  a linear or branched, saturated or not, C1-C7 alkyl, preferably a C1-C3 alkyl,
  a C3-C6 cycloalkyl, preferably a C4-C6 cycloalkyl, more preferably a cyclohexyl,
  an aryl group, preferably a phenyl group, possibly mono or polysubstituted, in particular disubstituted, by
    a halogen chosen among Cl, F, I and Br, or
    a linear or branched, saturated or not, C1-C7 alkyl, or
    a group —CO—R6, R6 being chosen among the group consisting of: —OH, —NH$_2$, or salt thereof, and —O—R7, R7 being a linear or branched, saturated or not, C1-C7 alkyl, or
    a group —O—R8, R8 being a linear or branched, saturated or not, C1-C7 alkyl, or
    a group —NO$_2$,
    a group —CN,
    a combination of the above,
  and
  an heteroaryl group, preferably a pyridyl or an isoquinolinyl, possibly mono or polysubstituted, in particular disubstituted, by
    a halogen chosen among Cl, F, I and Br, or
    a linear or branched, saturated or not, C1-C7 alkyl, or
    a group —CO—R6, R6 being chosen among the group consisting of: —OH, —NH$_2$, or salt thereof, and —O—R7, R7 being a linear or branched, saturated or not, C1-C7 alkyl, or
    a group —O—R8, R8 being a linear or branched, saturated or not, C1-C7 alkyl, or
    a combination of the above,
  provided that:
    if R2 is an aryl or an hetero aryl substituted by one a linear or branched, saturated or not, C1-C7 alkyl, said aryl or heteroaryl is also substituted by at least another group different from a C1-C7 alkyl, for its use for the treatment of pathologies involving an excess of activity of at least one member of the kallikrein family, preferably belonging to the group consisting of KLK5, KLK7 and KLK14, aforesaid pathologies belonging to the group consisting of psoriasis, atopic eczema and allergic contact dermatitis.

According to another embodiment, the present invention relates to the above mentioned compounds having the following formula (I-n1):

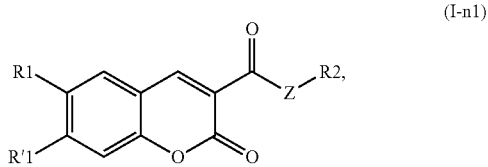
(I-n1)

wherein
Z represents O or S,
R1 represents at least one group chosen among the group consisting of:
hydrogen
a linear or branched, saturated or not, C1-C7 alkyl, preferably a methyl group, substituted, or not, by a halogen chosen among Cl, F, I and Br,
a linear or branched, saturated or not, C1-C7 alkyl, preferably a methyl group, substituted by a hydroxyl or a —O—R12 group, wherein R12 is a linear or branched, saturated or not, C1-C7 alkyl, preferably a hydroxyl,
a group —CH$_2$—O—CO—R5, wherein R5 is chosen among a hydrogen atom, and a linear or branched, saturated or not, C1-C7 alkyl, substituted or not by at least one halogen chosen among Cl, F, I and Br,
a group —O—R13, wherein R13 is chosen among hydrogen and a linear or branched, saturated or not, C1-C7 alkyl, R13 being preferably a hydrogen,
an amine

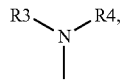

or a salt thereof, wherein R3 and R4, independently from each other, are chosen among hydrogen and a linear or branched, saturated or not, C1-C5 alkyl, and
a group

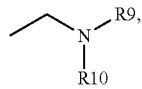

or a salt thereof, wherein R9 and R10, independently from each other, are chosen among:
hydrogen,
a linear or branched, saturated or not, C1-C5 alkyl,
—CO—R5, wherein R5 is chosen among a hydrogen atom, and a linear or branched, saturated or not, C1-C7 alkyl, substituted or not by at least one halogen chosen among Cl, F, I and Br,
—SO$_2$—R11, wherein R11 is a linear or branched, saturated or not, C1-C7 alkyl, R'1 represents a group chosen among hydrogen and —O—R14, wherein R14 is chosen among hydrogen and a linear or branched, saturated or not, C1-C7 alkyl, R14 being preferably a hydrogen, R'1 being preferably a hydrogen,
provided that R'1 represents hydrogen when R1 does not represent a —O—R13 group,
and
R2 is a naphthyl group, in particular a 1-naphthyl or a 2-naphthyl group, possibly mono or polysubstituted, in particular disubstituted, by
a halogen chosen among Cl, F, I and Br, or
a linear or branched, saturated or not, C1-C7 alkyl, or
a group —CO—R6, R6 being chosen among the group consisting of: —OH, —NH$_2$, or salt thereof, and —O—R7, R7 being a linear or branched, saturated or not, C1-C7 alkyl, or
a group —O—R8, R8 being a linear or branched, saturated or not, C1-C7 alkyl, or
a group —NO$_2$,
a group —CN,
a combination of the above,
for its use for the treatment of pathologies involving an excess of activity of at least one member of the kallikrein family, preferably belonging to the group consisting of KLK5, KLK7 and KLK14,
aforesaid pathologies belonging to the group consisting of Netherton syndrome, psoriasis, atopic eczema and allergic contact dermatitis, aforesaid pathologies being in particular Netherton syndrome.

According to another embodiment, the present invention relates to the above mentioned compounds having the following formula (I-n2):

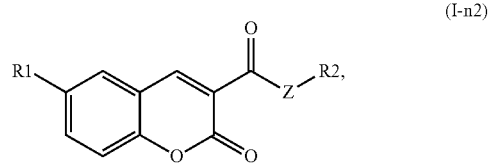
(I-n2)

wherein
Z represents O or S,
R1 represents at least one group chosen among the group consisting of:
hydrogen
a linear or branched, saturated or not, C1-C7 alkyl, preferably a methyl group, substituted, or not, by a halogen chosen among Cl, F, I and Br,
a linear or branched, saturated or not, C1-C7 alkyl, preferably a methyl group, substituted by a hydroxyl or a —O—R12 group, wherein R12 is a linear or branched, saturated or not, C1-C7 alkyl, preferably a hydroxyl,
a group —CH$_2$—O—CO—R5, wherein R5 is chosen among a hydrogen atom, and a linear or branched, saturated or not, C1-C7 alkyl, substituted or not by at least one halogen chosen among Cl, F, I and Br,
a group —O—R13, wherein R13 is chosen among hydrogen and a linear or branched, saturated or not, C1-C7 alkyl, R13 being preferably a hydrogen, an amine

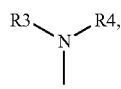

or a salt thereof, wherein R3 and R4, independently from each other, are chosen among hydrogen and a linear or branched, saturated or not, C1-C5 alkyl, and a group

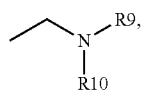

or a salt thereof, wherein R9 and R10, independently from each other, are chosen among:
hydrogen,
a linear or branched, saturated or not, C1-C5 alkyl,
—CO—R5, wherein R5 is chosen among a hydrogen atom, and a linear or branched, saturated or not, C1-C7 alkyl, substituted or not by at least one halogen chosen among Cl, F, I and Br,
—SO$_2$—R11, wherein R11 is a linear or branched, saturated or not, C1-C7 alkyl,
R2 is a naphthyl group, in particular a 1-naphthyl or a 2-naphthyl group, possibly mono or polysubstituted, in particular disubstituted, by
a halogen chosen among Cl, F, I and Br, or
a linear or branched, saturated or not, C1-C7 alkyl, or
a group —CO—R6, R6 being chosen among the group consisting of: —OH, —NH$_2$, or salt thereof, and —O—R7, R7 being a linear or branched, saturated or not, C1-C7 alkyl, or
a group —O—R8, R8 being a linear or branched, saturated or not, C1-C7 alkyl, or
a group —NO$_2$,
a group —CN,
a combination of the above,
for its use for the treatment of pathologies involving an excess of activity of at least one member of the kallikrein family, preferably belonging to the group consisting of KLK5, KLK7 and KLK14,
aforesaid pathologies belonging to the group consisting of Netherton syndrome, psoriasis, atopic eczema and allergic contact dermatitis, aforesaid pathologies being in particular Netherton syndrome.

According to another embodiment, the present invention relates to the above mentioned compounds having the following formula (I-n3):

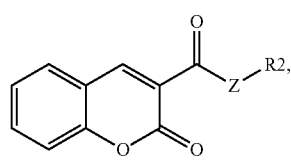

(I-n3)

wherein
Z represents O or S,
R2 is a naphthyl group, in particular a 1-naphthyl or a 2-naphthyl group, possibly mono or polysubstituted, in particular disubstituted, by
a halogen chosen among Cl, F, I and Br, or
a linear or branched, saturated or not, C1-C7 alkyl, or
a group —CO—R6, R6 being chosen among the group consisting of: —OH, —NH$_2$, or salt thereof, and —O—R7, R7 being a linear or branched, saturated or not, C1-C7 alkyl, or
a group —O—R8, R8 being a linear or branched, saturated or not, C1-C7 alkyl, or
a group —NO$_2$,
a group —CN,
a combination of the above,
for its use for the treatment of pathologies involving an excess of activity of at least one member of the kallikrein family, preferably belonging to the group consisting of KLK5, KLK7 and KLK14,
aforesaid pathologies belonging to the group consisting of Netherton syndrome, psoriasis, atopic eczema and allergic contact dermatitis, aforesaid pathologies being in particular Netherton syndrome.

According to another embodiment, the present invention relates to compounds of formula (I-h1) as presented below:

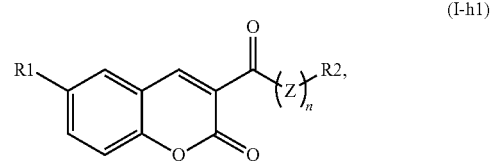

(I-h1)

wherein n equals 0 or 1,
and wherein
if n=1, Z represents O or S,
R1 represents —CH$_2$—Br or —CH$_2$—F,
R2 is chosen among the group consisting of:
a linear or branched, saturated or not, C1-C7 alkyl, preferably a C1-C3 alkyl,
a C3-C6 cycloalkyl, preferably a C4-C6 cycloalkyl, more preferably a cyclohexyl,
an aryl group, preferably a phenyl or a naphthyl group, possibly mono or or polysubstituted, in particular disubstituted, by
a halogen chosen among Cl, F, I and Br, or
a linear or branched, saturated or not, C1-C7 alkyl, or
a group —CO—R6, R6 being chosen among the group consisting of: —OH, —NH$_2$, or salt thereof, and —O—R7, R7 being a linear or branched, saturated or not, C1-C7 alkyl, or
a group —O—R8, R8 being a linear or branched, saturated or not, C1-C7 alkyl, or
a group —NO$_2$,
a group —CN,
a combination of the above,
and
an heteroaryl group, preferably a pyridyl or an isoquinolinyl, possibly mono or polysubstituted, in particular disubstituted, by
a halogen chosen among Cl, F, I and Br, or
a linear or branched, saturated or not, C1-C7 alkyl, or
a group —CO—R6, R6 being chosen among the group consisting of: —OH, —NH$_2$, or salt thereof, and —O—R7, R7 being a linear or branched, saturated or not, C1-C7 alkyl, or a group —O—R8, R8 being a linear or branched, saturated or not, C1-C7 alkyl, or a combination of the above, provided that when n=0, R2 is a methyl group or a cycloalkyl group, preferably a cyclohexyl group, when n=1, if R2 is an aryl different from a naphthyl, or an hetero aryl, substituted by one linear or branched, saturated or not, C1-C7 alkyl, said aryl or heteroaryl is also substituted by at least another group different from a C1-C7 alkyl, for its use for the treatment of pathologies involving an excess of activity of at least one member of the kallikrein family, preferably belonging to the group consisting of KLK5, KLK7 and KLK14, aforesaid pathologies belonging to the group consisting of Netherton syndrome, psoriasis, atopic eczema and allergic contact dermatitis, aforesaid pathologies being in particular Netherton syndrome.

According to another embodiment, the present invention relates to the above mentioned compounds having the following formula (I-h2):

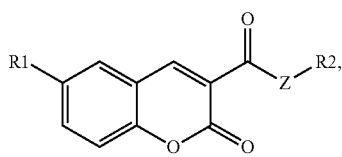

(I-h2)

wherein

Z represents O or S,

R1 represents —CH$_2$—Br or —CH$_2$—F,

R2 is chosen among the group consisting of:
  a linear or branched, saturated or not, C1-C7 alkyl, preferably a C1-C3 alkyl,
  a C3-C6 cycloalkyl, preferably a C4-C6 cycloalkyl, more preferably a cyclohexyl,
  an aryl group, preferably a phenyl or a naphthyl group, possibly mono or or polysubstituted, in particular disubstituted, by
    a halogen chosen among Cl, F, I and Br, or
    a linear or branched, saturated or not, C1-C7 alkyl, or
    a group —CO—R6, R6 being chosen among the group consisting of: —OH, —NH$_2$, or salt thereof, and —O—R7, R7 being a linear or branched, saturated or not, C1-C7 alkyl, or
    a group —O—R8, R8 being a linear or branched, saturated or not, C1-C7 alkyl, or
    a group —NO$_2$,
    a group —CN,
    a combination of the above,
and
  an heteroaryl group, preferably a pyridyl or an isoquinolinyl, possibly mono or polysubstituted, in particular disubstituted, by
    a halogen chosen among Cl, F, I and Br, or
    a linear or branched, saturated or not, C1-C7 alkyl, or
    a group —CO—R6, R6 being chosen among the group consisting of: —OH, —NH$_2$, or salt thereof, and —O—R7, R7 being a linear or branched, saturated or not, C1-C7 alkyl, or a group —O—R8, R8 being a linear or branched, saturated or not, C1-C7 alkyl, or a combination of the above, provided that if R2 is an aryl different from a naphthyl, or an hetero aryl, substituted by one linear or branched, saturated or not, C1-C7 alkyl, said aryl or heteroaryl is also substituted by at least another group different from a C1-C7 alkyl, for its use for the treatment of pathologies involving an excess of activity of at least one member of the kallikrein family, preferably belonging to the group consisting of KLK5, KLK7 and KLK14, aforesaid pathologies belonging to the group consisting of Netherton syndrome, psoriasis, atopic eczema and allergic contact dermatitis, aforesaid pathologies being in particular Netherton syndrome.

According to another embodiment, the present invention relates to the above mentioned compounds having the following formula (I-h3):

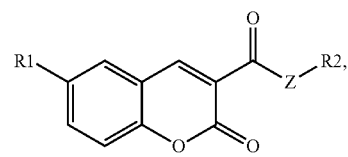

(I-h3)

wherein

Z represents O or S,

R1 represents —CH$_2$—Br or —CH$_2$—F,

R2 is an aryl group, preferably a phenyl or a naphthyl group, possibly mono or or polysubstituted, in particular disubstituted, by
  a halogen chosen among Cl, F, I and Br, or
  a linear or branched, saturated or not, C1-C7 alkyl, or
  a group —CO—R6, R6 being chosen among the group consisting of: —OH, —NH$_2$, or salt thereof, and —O—R7, R7 being a linear or branched, saturated or not, C1-C7 alkyl, or
  a group —O—R8, R8 being a linear or branched, saturated or not, C1-C7 alkyl, or
  a group —NO$_2$,
  a group —CN,
  a combination of the above, provided that if R2 is an aryl different from a naphthyl, or an hetero aryl, substituted by one linear or branched, saturated or not, C1-C7 alkyl, said aryl or heteroaryl is also substituted by at least another group different from a C1-C7 alkyl, for its use for the treatment of pathologies involving an excess of activity of at least one member of the kallikrein family, preferably belonging to the group consisting of KLK5, KLK7 and KLK14, aforesaid pathologies belonging to the group consisting of Netherton syndrome, psoriasis, atopic eczema and allergic contact dermatitis, aforesaid pathologies being in particular Netherton syndrome.

According to another embodiment, the present invention relates to the compound of formula (II1)

(CFL33)

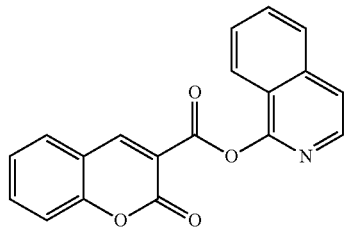

According to another embodiment, the present invention relates to a compound selected from the group comprising:

(SMB28)

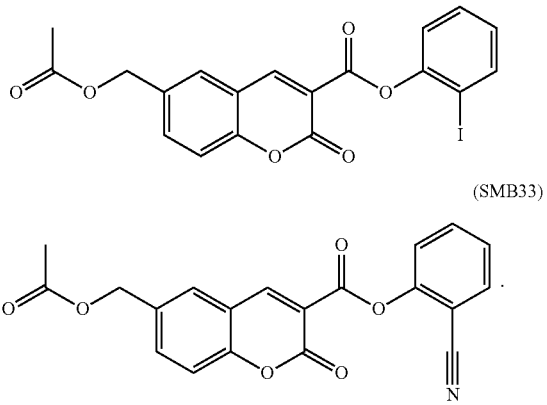

(SMB33)

According to another embodiment, the present invention relates to a compound selected from the group comprising:

(JFR5)

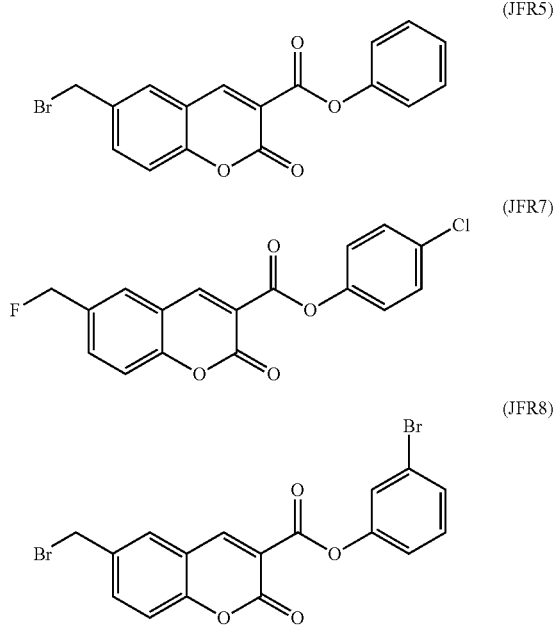

(JFR7)

(JFR8)

(JFR9)

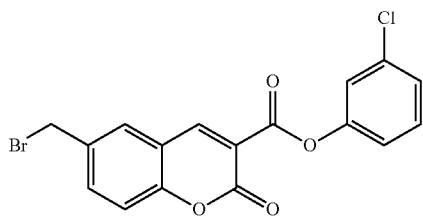

(JFR11.)

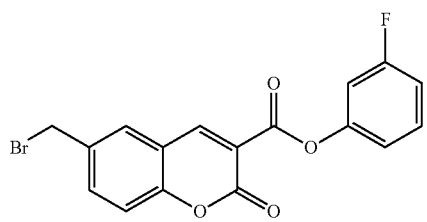

The synthesis of the coumarin derivatives of the invention is described in the patent of Reboud-Ravaux et al (WO9855472) and in the literature (Pochet L., Doucet C., Schynts M., Thierry N., Boggetto N., Pirotte B., Jiang K. I., Masereel B., de Tullio P., Delarge J., Reboud-Ravaux M., *J. Med. Chem*, 1996, 39, 2579-2585; Doucet C., Pochet L., Thierry N., Pirotte B., Delarge J., Reboud-Ravaux M., *J. Med. Chem*, 1999, 42, 4161-4171). On the other hand, the compound CFL33 is a new coumarin derivative. Its synthesis is described in the example 1.

Compounds SMB28 and SMB33 are new coumarin derivatives. Their synthesis is respectively described in examples 1.2 and 1.3.

Compounds JFR5, JFR7, JFR8, JFR9 and JFR11 are new coumarin derivatives. Their synthesis is described in examples 1.6 to 1.10.

According to another embodiment, the present invention relates to the compound of formula CFL33 for its use as drug.

According to another embodiment, the present invention relates to a compound selected from the group comprising SMB28 and SMB33, for its use as drug.

According to another embodiment, the present invention relates to a compound selected from the group comprising JFR5, JFR7, JFR8, JFR9 and JFR11, for its use as drug.

According to another embodiment, the present invention is therefore directed towards the preparation of a pharmaceutical composition comprising as active substance a compound of formula CFL33 in association with a pharmaceutically acceptable carrier.

According to another embodiment, the present invention is therefore directed towards the preparation of a pharmaceutical composition comprising as active substance a compound selected from the group comprising SMB28 and SMB33 in association with a pharmaceutically acceptable carrier.

According to another embodiment, the present invention is therefore directed towards the preparation of a pharmaceutical composition comprising as active substance a compound selected from the group comprising JFR5, JFR7, JFR8, JFR9 and JFR11 in association with a pharmaceutically acceptable carrier.

The invention is therefore directed towards the preparation of a pharmaceutical composition containing a compound of formula CFL33 as a drug in which said compound has a kallikrein-inhibitory activity. This composition is characterized in that it comprises, in a pharmaceutically acceptable carrier that is compatible with the method of administration selected for said composition, a compound of formula CFL33.

The invention is therefore directed towards the preparation of a pharmaceutical composition containing a compound selected from the group comprising SMB28 and SMB33 as a drug in which said compound has a kallikrein-inhibitory activity. This composition is characterized in that it comprises, in a pharmaceutically acceptable carrier that is compatible with the method of administration selected for said composition, aforesaid compound selected from the group comprising SMB28 and SMB33.

The invention is therefore directed towards the preparation of a pharmaceutical composition containing a compound selected from the group comprising JFR5, JFR7, JFR8, JFR9 and JFR11 as a drug in which said compound has a kallikrein-inhibitory activity. This composition is characterized in that it comprises, in a pharmaceutically acceptable carrier that is compatible with the method of administration selected for said composition, aforesaid compound selected from the group comprising JFR5, JFR7, JFR8, JFR9 and JFR11.

The term "pharmaceutically acceptable carrier" is intended to mean a medium that is compatible with the skin, the mucous membranes and systemic administration.

The composition according to the invention can be administered topically. Preferably, the pharmaceutical composition is packaged in a form suitable for topical application.

When used topically, the pharmaceutical composition according to the invention is more particularly for use in the treatment of the skin and the mucous membranes and may be in liquid, pasty or solid form, and more particularly in the form of ointments, creams, solutions or gels.

The compositions used for topical application have a concentration of compound according to the invention of generally between 0.001% and 20% by weight, relative to the total weight of the composition.

The composition according to the invention can be administered systemically. Preferably, the pharmaceutical composition is packaged in a form suitable for systemic administration. The routes of administration can be parenteral, digestive, rectal, transcutaneous.

More particularly, the composition according to the invention may be in the form of injectable solutions or suspensions, tablets, capsules, powders or preparation for trans dermal use.

The posology may vary according to the severity of the disease, the patient's age and weight and the route of administration. Generally, the unit dose may be of 1 to 200 mg per taking and the daily dose may be of 2 to 500 mg.

The pharmaceutical composition as described above may also contain inert additives or pharmacodynamically active additives as regards the pharmaceutical compositions, or combinations of theses additives.

According to another embodiment, the present invention relates to a composition comprising a compound of formula CFL33 for its use for the treatment of skin pathologies. According to another embodiment, the present invention relates to a composition comprising a compound selected from the group comprising SMB28 and SMB33 for its use for the treatment of skin pathologies.

According to another embodiment, the present invention relates to a composition comprising a compound selected from the group comprising JFR5, JFR7, JFR8, JFR9 and JFR11 for its use for the treatment of skin pathologies.

According to another embodiment, the present invention relates to a composition comprising a compound of formula CFL33 wherein said skin pathologies belong to the group consisting of Netherton syndrome, atopic dermatitis, psoriasis, eczema and peeling skin syndrome, preferably Netherton syndrome.

According to another embodiment, the present invention relates to a composition comprising a compound of formula CFL33 wherein said skin pathologies belong to the group consisting of Netherton syndrome, psoriasis, atopic eczema and allergic contact dermatitis, preferably Netherton syndrome.

According to another embodiment, the present invention relates to a composition comprising a compound selected from the group comprising SMB28 and SMB33 wherein said skin pathologies belong to the group consisting of Netherton syndrome, atopic dermatitis, psoriasis, eczema and peeling skin syndrome, preferably Netherton syndrome.

According to another embodiment, the present invention relates to a composition comprising a compound selected from the group comprising SMB28 and SMB33 wherein said skin pathologies belong to the group consisting of Netherton syndrome, psoriasis, atopic eczema and allergic contact dermatitis, preferably Netherton syndrome.

According to another embodiment, the present invention relates to a composition comprising a compound selected from the group comprising JFR5, JFR7, JFR8, JFR9 and JFR11 wherein said skin pathologies belong to the group consisting of Netherton syndrome, atopic dermatitis, psoriasis, eczema and peeling skin syndrome, preferably Netherton syndrome.

According to another embodiment, the present invention relates to a composition comprising a compound selected from the group comprising JFR5, JFR7, JFR8, JFR9 and JFR11 wherein said skin pathologies belong to the group consisting of Netherton syndrome, psoriasis, atopic eczema and allergic contact dermatitis, preferably Netherton syndrome.

The compound CFL33 according to the invention is suitable for use related to the treatment or prevention of skin disorders such as Netherton syndrome, atopic dermatitis, psoriasis, eczema and peeling skin syndrome, preferably Netherton syndrome.

The compound CFL33 according to the invention is suitable for use related to the treatment or prevention of skin disorders such as Netherton syndrome, psoriasis, atopic eczema and allergic contact dermatitis, preferably Netherton syndrome.

The compound selected from the group comprising SMB28 and SMB33 according to the invention is suitable for use related to the treatment or prevention of skin disorders such as Netherton syndrome, atopic dermatitis, psoriasis, eczema and peeling skin syndrome, preferably Netherton syndrome.

The compound selected from the group comprising SMB28 and SMB33 according to the invention is suitable for use related to the treatment or prevention of skin disorders such as Netherton syndrome, psoriasis, atopic eczema and allergic contact dermatitis, preferably Netherton syndrome.

The compound selected from the group comprising JFR5, JFR7, JFR8, JFR9 and JFR11 according to the invention is suitable for use related to the treatment or prevention of skin disorders such as Netherton syndrome, atopic dermatitis, psoriasis, eczema and peeling skin syndrome, preferably Netherton syndrome.

The compound selected from the group comprising JFR5, JFR7, JFR8, JFR9 and JFR11 according to the invention is suitable for use related to the treatment or prevention of skin disorders such as Netherton syndrome, psoriasis, atopic eczema and allergic contact dermatitis, preferably Netherton syndrome.

FIG. 1: This figure presents the activation cascade involving kallikreins. In Netherton syndrome LEKTI loses its faculty to efficiently control the KLK5, leading to an abnormal skin desquamation due to an increase of the degradation of the corneodesmosomes proteins. Synthetic inhibitors are susceptible to control the double KLK5 function, that is direct degradation and other proteases activation, KLK7 and KLK14, this one activating pro-elastase.

FIG. 2 and FIG. 3 present cell viability of normal human keratinocytes after treatment with some compounds of the present invention, respectively at 1 μM (FIG. 2) and 10 μM (FIG. 3).

FIG. 4 shows the mean+/−SD of the expression of the target genes relative to the expression of the housekeeping gene: (A) TSLP, (B) IL-8, (C) TNFα, (D) MDC and (E) TARC.

Figure 5:
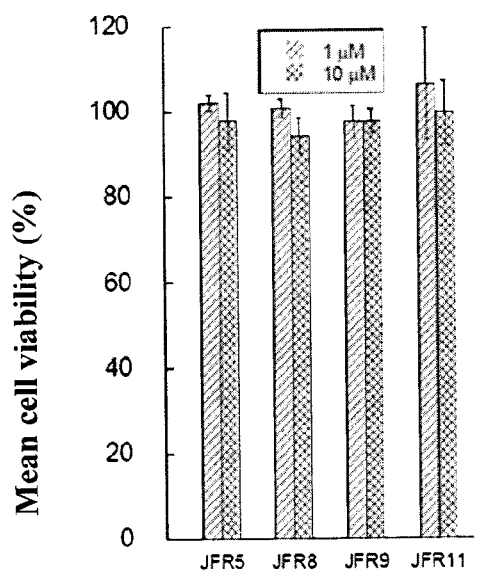

FIG. 5 presents the evaluation of the cytotoxic effect of coumarin compounds JFR5, JFR8, JFR9 and JFR11 on healthy human keratinocytes at 1 (hatched) and 10 (cross hatched) μM after a 48 h treatment and neutral red staining. Three independent experiments were performed for each compound.

Figure 6:
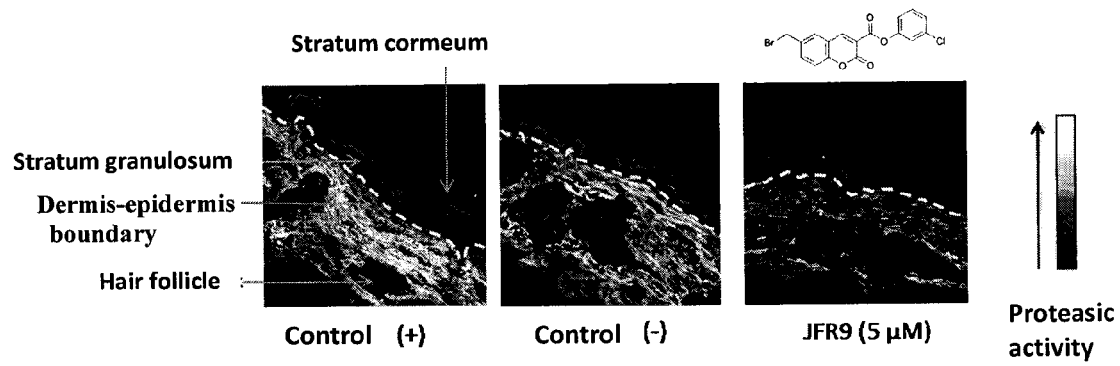

FIG. 6 illustrates the effect of JFR9 compound (5 μM) efficacy on the total protease activity of transgenic KLK5 mice skin section, by in situ zymography.

The protease activity is shown with a gradient of fluorescence. The fluorescence intensity represents the cleavage efficiency of a casein substrate coupled to a FITC group.

Control (+): no inhibitor added; control (−): addition of a coumarin compound that does not inhibit proteases.

EXAMPLES

Example 1

Synthesis of CFL33, isoquinolin-1-yl 2-oxo-2H-1-benzopyran-3-carboxylate 1.0 g of the commercially available 2-oxo-2H-1-benzopyran-3-carboxylic acid and 10 ml of thionyl chloride were refluxed for 3 h. The resulting solution was evaporated under reduced pressure. The residue was suspended in 10 ml anhydrous toluene. The solvent was eliminated by distillation under reduced pressure. The two last steps were repeated twice. The residue was dispersed in 10 ml dioxane. To this suspension were added 1-hydroxyquinoleine (1.1 éq.) and anhydrous pyridine (1.1 eq.). After 90 min stirring at room temperature, the solvent was removed by distillation under reduced pressure. The residue was solubilized in chloroform and the organic phase was washed three times with HCl 0.1N, then dried over $MgSO_4$. The solvent was evaporated under reduced pressure and the residue obtained was recrystallized in ethyl acetate.

white solid; m.p. 197-200° C.

$^1$H NMR (500 MHz) DMSO-$d_6$: 6.87 (d, 1H, 4-H isoquin.), 7.47 (t, 1H, 6-H coumar.), 7.52 (d, 1H, 8-H coumar.), 7.58 (t, 1H, 7-H isoquin.), 7.75 (m, 2H, 7-H coumar. +5-H isoquin.), 7.84 (m, 2H, 6-H+3-H isoquin.), 7.93 (d, 1H, 5-H coumar.), 8.16 (d, 1H, 8-H isoquin.), 8.56 (s, 1H, 4-H coumar.).

Example 1.2

Synthesis of SMB28, 2-iodophenyl 6-acetoxymethyl-2-oxo-2H-1-benzopyran-3-carboxylate To the suspension of the acid chloride of 6-acetoxymethyl-2-oxo-2H-1-benzopyran-3-carboxylic acid (4 mmol) obtained according to Pochet et al. (Bioorg. Med. Chem. 2000, 8, 1489) in anhydrous dioxane (10 mL) was added 2-iodophenol (5 mmol) and pyridine (0.4 mL). After 12 h stirring at room temperature, the solvent was evaporated under vacuum and the residue was suspended in methanol. The resulting precipitate was collected by filtration, washed with methanol and dried. The solid was crystallized in ethyl acetate (45%); mp: 156-158° C.

Example 1.3

Synthesis of SMB33, 2-cyanophenyl 6-acetoxymethyl-2-oxo-2H-1-benzopyran-3-carboxylate To the suspension of the acid chloride of 6-acetoxymethyl-2-oxo-2H-1-benzopyran-3-carboxylic acid (4 mmol) obtained according to Pochet et al. (Bioorg. Med. Chem. 2000, 8, 1489) in anhydrous dioxane (10 mL) was added 2-cyanophenol (5 mmol) and pyridine (0.4 mL). After 12 h stirring at room temperature, the solvent was evaporated under vacuum and the residue was suspended in methanol. The resulting precipitate was collected by filtration, washed with methanol and dried. The solid was crystallized in ethyl acetate (40%); mp: 181-183° C.

General synthetic pathway to naphthyl 2-oxo-2H-1-benzopyran-3-carboxylates dioxane (12 mL) was supplemented with 8 drops of piperidine and 4 drops of glacial acetic acid and stirred for 30 minutes at room temperature. At the end of the reaction, the solvent was removed by distillation under reduced pressure and the residue was triturated with cold methanol (20 mL). The resulting precipitate was collected by filtration, washed with cold methanol and dried. The white solid of the title compound was recrystallized in a mixture of methylene chloride and hexane (yields: 75-80%).

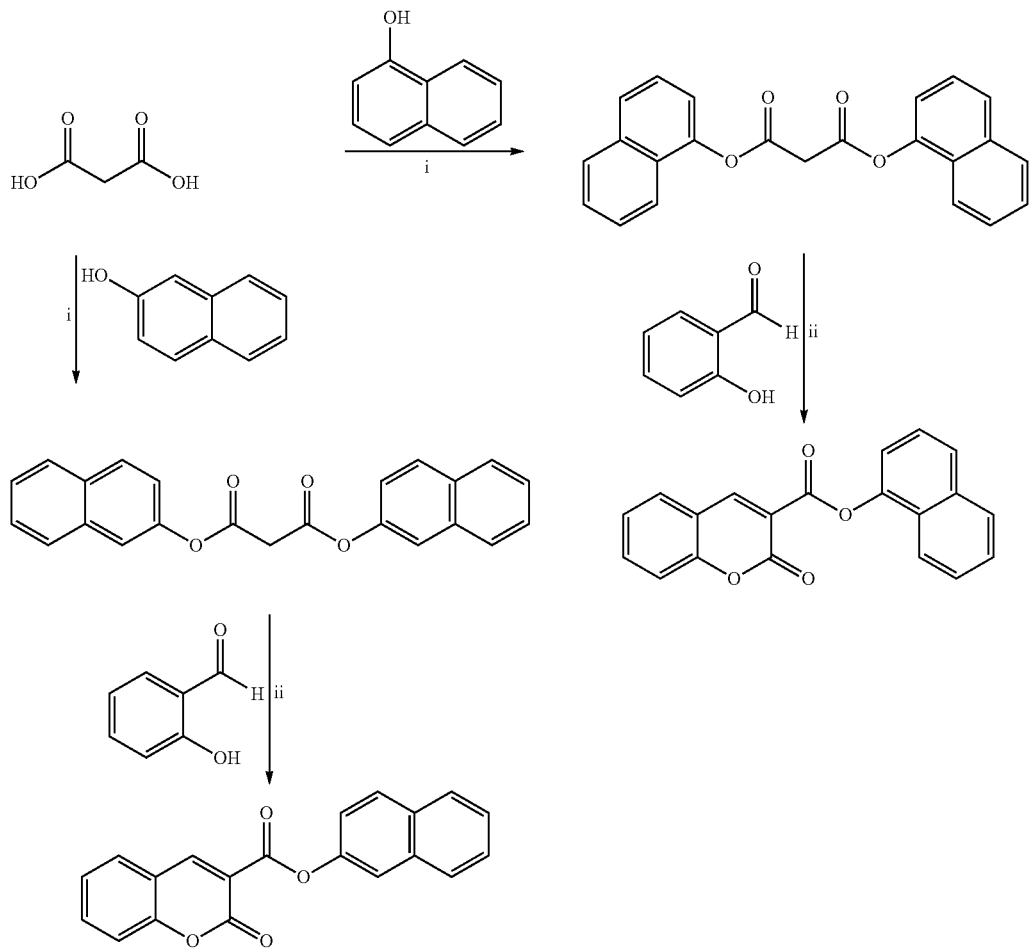

Reagents: i: OPCl₃; ii: piperidine, HOAc, dioxane.

Synthesis of Dinaphthyl Esters of Malonic Acid

The mixture of malonic acid (2 g, 19.2 mmol), the appropriate naphthol (2 eq., 38.4 mmol) and phosphoryl chloride (2 eq., 38.4 mmol) was heated at 100° C. for 90 minutes. The reaction mixture was then carefully poured on a cooled 1% w/v aqueous solution of sodium hydroxide (50 mL). The resulting precipitate of the title compound was collected by filtration, washed with water, dried and recrystallized in methanol (yields: 25-30%). The white solid of the title compound was used in the next step without further purification.

Synthesis of naphthyl 2-oxo-2H-1-benzopyran-3-carboxylates

The solution of salicylaldehyde (0.4 g, 3.28 mmol) and the appropriate dinaphthyl malonate (1.5 eq., 4.92 mmol) in Example 1.4

1-Naphthyl 2-oxo-2H-1-benzopyran-3-carboxylate (JFR1)

1-Naphthyl 2-oxo-2H-1-benzopyran-3-carboxylate (JFR1) was obtained according to the above-mentioned general procedure, starting from 1-naphthol.

m.p.: 159-160° C.

Example 1.5

2-Naphthyl 2-oxo-2H-1-benzopyran-3-carboxylate (JFR2)

2-Naphthyl 2-oxo-2H-1-benzopyran-3-carboxylate (JFR2) was obtained according to the above-mentioned general procedure, starting from 2-naphthol.

m.p.: 166-167° C.

General synthetic pathway to halophenyl
6-halomethyl-2-oxo-2H-1-benzopyran-3-carboxylates

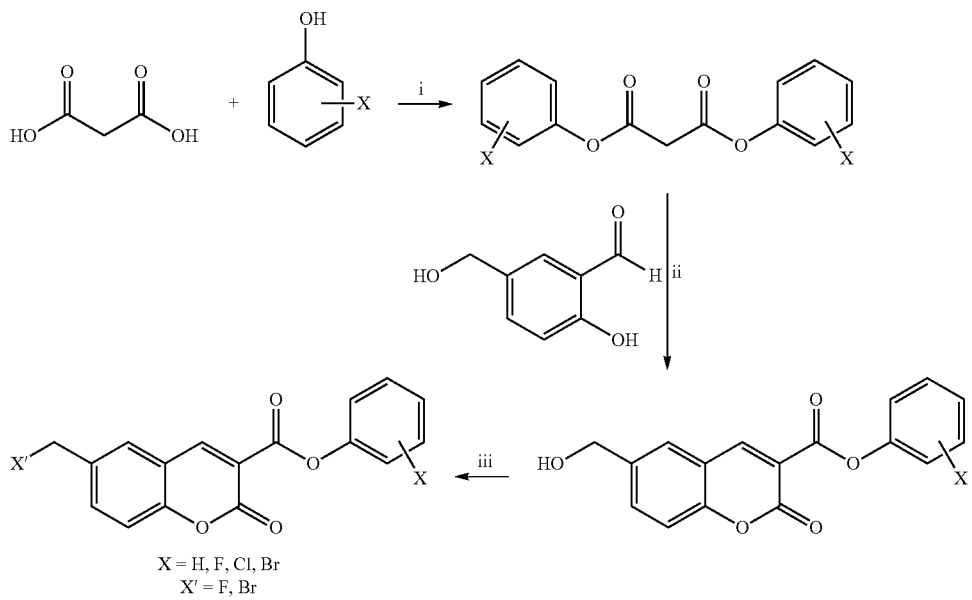

X = H, F, Cl, Br
X' = F, Br

Reagents: i: OPCl$_3$; ii: piperidine, HOAc, dioxane; iii: X' = F: Ishikawa's reagent, CH$_2$Cl$_2$; X' = Br: SOBr$_2$, pyridine, CH$_2$Cl$_2$.

Synthesis of Di(Halo)Phenyl Esters of Malonic Acid

The mixture of malonic acid (2 g, 19.2 mmol), the appropriate halophenol (2 eq., 38.4 mmol) and phosphoryl chloride (2 eq., 38.4 mmol) was heated at 100° C. for 90 minutes. The reaction mixture was then carefully poured on a cooled 1% w/v aqueous solution of sodium hydroxide (50 mL). The resulting precipitate of the title compound was collected by filtration, washed with water, dried and recrystallized in methanol (yields: 65-80%). The white solid of the title compound was used in the next step without further purification.

Synthesis of (halo)phenyl 6-hydroxymethyl-2-oxo-2H-1-benzopyran-3-carboxylates

The solution of 5-hydroxymethylsalicylaldehyde (Stoermer et al. Ber. 1901, 34, 2455-2460) (0.4 g, 2.62 mmol) and the appropriate di(halo)phenyl malonate (1.5 eq., 3.94 mmol) in dioxane (12 mL) was supplemented with 8 drops of piperidine and 4 drops of glacial acetic acid and stirred for 30 minutes at room temperature. At the end of the reaction, the solvent was removed by distillation under reduced pressure and the residue was triturated with cold methanol (10-20 mL). The resulting precipitate was collected by filtration, washed with cold methanol and dried (yields: 70-85%). The white solid of the title compound was used in the next step without further purification.

Synthesis of (halo)phenyl 6-bromomethyl-2-oxo-2H-1-benzopyran-3-carboxylates

The appropriate (halo)phenyl 6-hydroxymethyl-2-oxo-2H-1-benzopyran-3-carboxylate (0.4 g, ~0.7 mmol) was dissolved in methylene chloride (10 mL) and then supplemented with pyridine (1.0 eq.) and thionyl bromide (1.15 eq.). The reaction mixture was heated under reflux for 90 minutes. After cooling, the reaction medium was poured onto water (20 mL). The organic layer was collected, dried over magnesium sulfate, filtered and concentrated under reduced pressure. The residue of the title compound was recrystallized in a mixture of methylene chloride and hexane (yields: 15-50%).

Example 1.6

Phenyl 6-bromomethyl-2-oxo-2H-1-benzopyran-3-carboxylate (JFR5)

Phenyl 6-bromomethyl-2-oxo-2H-1-benzopyran-3-carboxylate (JFR5) was obtained according to the above-mentioned general procedure, starting from phenol.
m.p.: 186-187° C.

Example 1.7

3-Fluorophenyl 6-bromomethyl-2-oxo-2H-1-benzopyran-3-carboxylate (JFR11)

3-Fluorophenyl 6-bromomethyl-2-oxo-2H-1-benzopyran-3-carboxylate (JFR11) was obtained according to the above-mentioned general procedure, starting from 3-fluorophenol.
m.p.: 189-190° C.

Example 1.8

3-Chlorophenyl 6-bromomethyl-2-oxo-2H-1-benzopyran-3-carboxylate (JFR9)

3-Chlorophenyl 6-bromomethyl-2-oxo-2H-1-benzopyran-3-carboxylate (JFR9) was obtained according to the above-mentioned general procedure, starting from 3-chlorophenol.
m.p.: 186-187° C.

Example 1.9

3-Bromophenyl 6-bromomethyl-2-oxo-2H-1-benzopyran-3-carboxylate (JFR8)

3-Bromophenyl 6-bromomethyl-2-oxo-2H-1-benzopyran-3-carboxylate (JFR8) was obtained according to the above-mentioned general procedure, starting from 3-bromophenol.

m.p.: 185-186° C.

Synthesis of (halo)phenyl 6-fluoromethyl-2-oxo-2H-1-benzopyran-3-carboxylates The appropriate (halo)phenyl 6-hydroxymethyl-2-oxo-2H-1-benzopyran-3-carboxylate (0.4 g, ~0.7 mmol) was dissolved in methylene chloride (10 mL) and the resulting solution cooled on an ice bath was supplemented with Ishikawa's reagent (2.5 eq.). The reaction mixture was stirred for 30 minutes at 0° C. and then heated under reflux for 90 minutes. After cooling, the reaction medium was poured onto water (20 mL). The organic layer was collected, dried over magnesium sulfate, filtered and concentrated under reduced pressure. The residue of the title compound was purified by column chromatography on silicagel (eluent: methylene chloride) and then recrystallized in a mixture of methylene chloride and hexane (yields: 15-55%).

Example 1.10

4-Chlorophenyl 6-fluoromethyl-2-oxo-2H-1-benzopyran-3-carboxylate (JFR7)

4-Chlorophenyl 6-fluoromethyl-2-oxo-2H-1-benzopyran-3-carboxylate (JFR7) was obtained according to the above-mentioned general procedure, starting from 4-chlorophenol.

m.p.: 216-218° C.

Example 2

Biological Results, Enzyme and Inhibition Assays

In the examples described below:
DMSO means "dimethylsulfoxide"
Tris-HCl means "tris(hydroxymethyl)aminomethane, hydrogen chloride>>
Tween 20 refers to polysorbate 20 or polyoxyethylene (20) sorbitan monolaurate
The Hill number provides a way to characterize the binding of a ligand to a macromolecule.
Kallikreins KLK5, KLK7 and KLK14 activities were determined by monitoring the hydrolysis of the appropriate fluorogenic substrate ($\lambda_{exc}$=355, =460 nm) for 15 min at 37° C. in the presence of the untreated kallikrein (control) or kallikrein that had been incubated with a test compound. Substrate and compounds were previously dissolved in DMSO, with the final solvent concentration kept constant at 2% (v/v) (KLK 5 and 14), and 4% (v/v) (KLK7). The composition of the activity buffers (pH 8.0) was 100 mM Tris-HCl, 150 mM NaCl, 0.01% (v/v) Tween 20 for the KLK5 assay, and 100 mM Tris-HCl, 1M NaCl, 0.01% (v/v) Tween 20 in the KLK 7 and 14 assays. The final concentrations were 0.6 nM (KLK5) and 100 µM (Boc-Val-Pro-Arg-AMC) (KLK5 assay), 8 nM (KLK7) and 40 µM (Suc-Leu-Leu-Val-Tyr-AMC, AMC:7-amino-4-methyl-coumarin) (KLK7 assay), and 0.17 nM (KLK14) and 10 µM (Boc-Val-Pro-Arg-AMC) (KLK14 assay). Using the appropriate substrate, the coumarinic compounds (0.01-100 µM) were tested in duplicate for each inhibitor concentration to detect their inhibitory potential. The enzyme and the inhibitors were incubated for 15 min before the determination of the enzyme activity. Initial rates determined in control experiments ($V_0$) were considered to be 100% of the peptidase activity; initial rates below 100% were considered to be inhibitions. The inhibitory activity of compounds was expressed as $IC_{50}$ (inhibitor concentrations giving 50% inhibition). The values of $IC_{50}$ were calculated by fitting the experimental data to the equation:

% Inhibition=$100\times(1-V_i/V_0)=100[I]_0/(IC_{50}+[I]_0)$, or equation:

% Inhibition=$100[I]_0^{nH}/(IC_{50}^{nH}+[I]_0^{nH})$, $n_H$ is the Hill number.

Example 3

Characterization of the Inhibition Reversibility

To examine the putative covalent nature of the inhibition by coumarins, percentage of inhibition was monitored as function of time; a putative enzyme reactivation by hydroxylamine was detected. The reaction mixtures containing the inhibited enzyme were treated with 0.5 M hydroxylamine at pH 7.5 and 37° C. during 30 min. Enzyme activity of aliquots was monitored and compared to a control. The fast reactivation in the presence of hydroxylamine indicated the formation of a stable acyl-enzyme; the absence of reactivation was in agreement with a suicide inactivation.

The results obtained for the compounds of the invention are shown in tables A and A2.

The tests were realized at 37° C. after 15 min of incubation at pH 8.

In these tables, <<NI>> means non-inhibitor and ND non-determined

TABLE A

| molecule | name | IC$_{50}$ (µM) or % Inhibition | | |
|---|---|---|---|---|
| | | KLK5 | KLK7 | KLK14 |
| (structure) | MFS7 | 26% (50 µM) | 0.235 ± 0.009 | 45% (100 µM) |

83 84
TABLE A-continued
| molecule | name | IC$_{50}$ (μM) or % Inhibition | | |
|---|---|---|---|---|
| | | KLK5 | KLK7 | KLK14 |
| 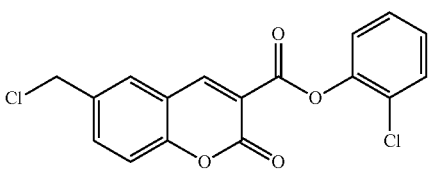 [SMILES: O=C(Oc1ccccc1Cl)c1cc2cc(CCl)ccc2oc1=O] | MFS36 | 50% (100 μM) | 0.209 ± 0.006 | 100% (100 μM) |
| 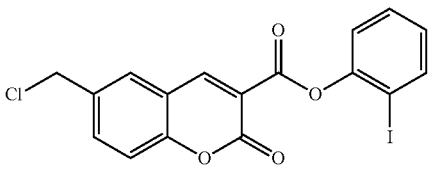 [SMILES: O=C(Oc1ccccc1I)c1cc2cc(CCl)ccc2oc1=O] | LP15 | NI | 1.9 ± 0.1 | 37% (100 μM) |
| 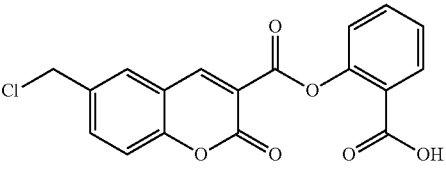 [SMILES: O=C(O)c1ccccc1OC(=O)c1cc2cc(CCl)ccc2oc1=O] | IK11 | 37.4% (50 μM) | 63% (100 μM) | 43 ± 4 |
| 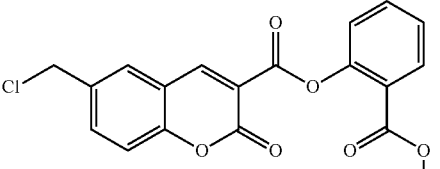 | IK1 | 26.3 ± 1.4 | 2.7 ± 0.1 | 38 ± 5 |
| 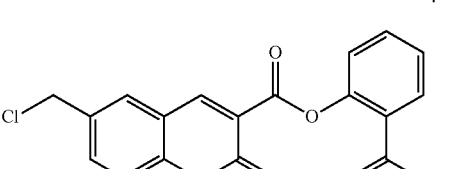 | IK3 | NI | NI | 77% (100 μM) |
| 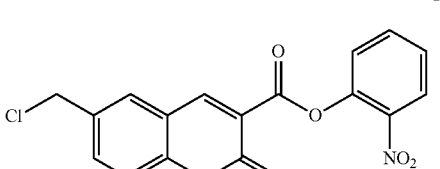 | LP60 | 112 ± 6 | 1.44 ± 0.02 | 46% (100 μM) |
| 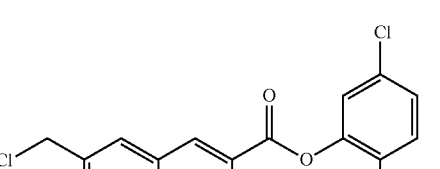 | IK5 | 36.9 ± 4.2 | 5.8 ± 0.2 | 89 ± 10 |
| 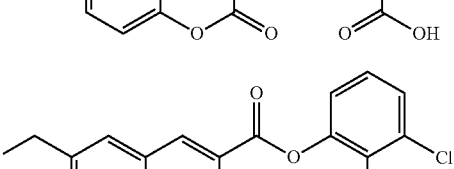 | LP73 | NI | 0.063 ± 0.004 | NI |

TABLE A-continued
| molecule | name | IC$_{50}$ (μM) or % Inhibition | | |
|---|---|---|---|---|
| | | KLK5 | KLK7 | KLK14 |
| 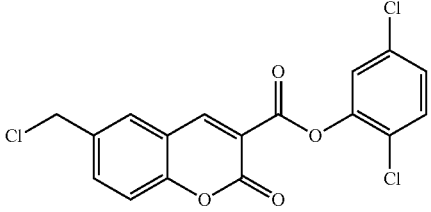 [SMILES: O=C(Oc1cc(Cl)ccc1Cl)c1cc2cc(CCl)ccc2oc1=O] | LP74 | 1.3 ± 0.2 | 0.195 ± 0.024 | 54 ± 6 μM |
| 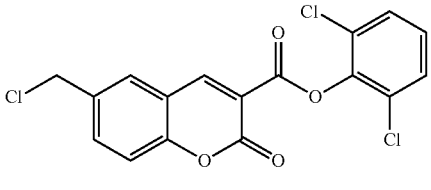 [SMILES: O=C(Oc1c(Cl)cccc1Cl)c1cc2cc(CCl)ccc2oc1=O] | LP72 | 59 ± 9 | 0.495 ± 0.037 | 50% (100 μM) |
| 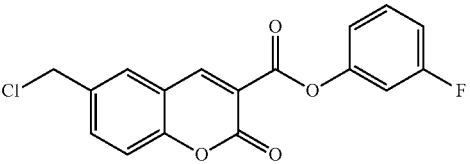 [SMILES: O=C(Oc1cccc(F)c1)c1cc2cc(CCl)ccc2oc1=O] | LP51 | 26% (50 μM) | 0.25 ± 0.01 | 30% (100 μM) |
| 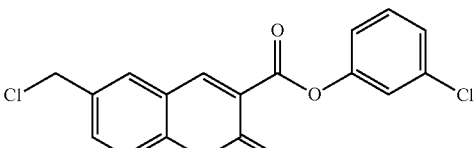 | LP8 | 49% (100 μM) | 0.103 ± 0.005 | 40% (100 μM) |
| 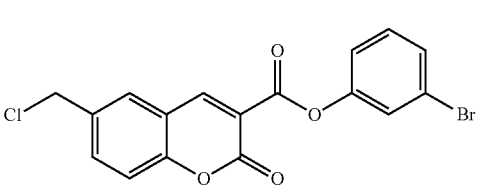 [SMILES: O=C(Oc1cccc(Br)c1)c1cc2cc(CCl)ccc2oc1=O] | LP53 | 34% (50 μM) | 0.065 ± 0.003 | 41% (100 μM) |
| 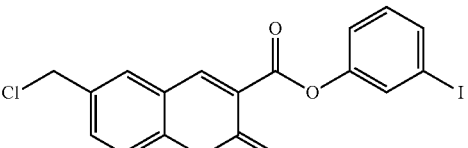 | LP14 | 48% (100 μM) | 0.077± 0.003 | 70% (100 μM) |
| 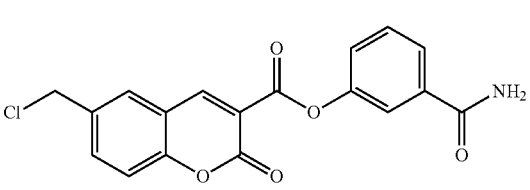 [SMILES: NC(=O)c1cccc(OC(=O)c2cc3cc(CCl)ccc3oc2=O)c1] | IK4 | 21.6 ± 5 | 7.8 ± 0.6 | 30 ± 8 |
| 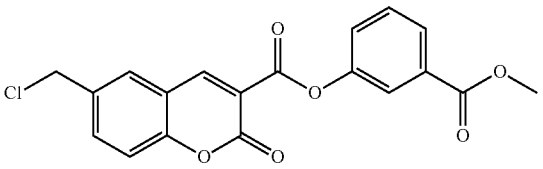 [SMILES: COC(=O)c1cccc(OC(=O)c2cc3cc(CCl)ccc3oc2=O)c1] | IK2 | NI | 0.68 ± 0.01 | 67% (100 μM) |

TABLE A-continued
| molecule | name | IC$_{50}$ (μM) or % Inhibition | | |
| --- | --- | --- | --- | --- |
| | | KLK5 | KLK7 | KLK14 |
| 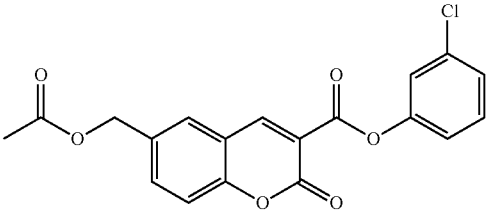 [SMILES: CC(=O)OCc1ccc2oc(=O)c(C(=O)Oc3cccc(Cl)c3)cc2c1] | LP46 | 31% (50 μM) | ND | 31 ± 6 |
| 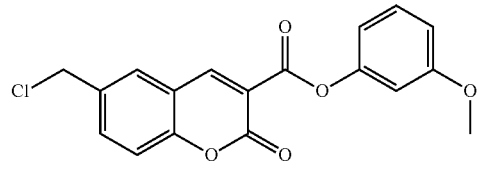 [SMILES: COc1cccc(OC(=O)c2cc3cc(CCl)ccc3oc2=O)c1] | LP55 | NI | 8.4 ± 0.2 | NI |
| 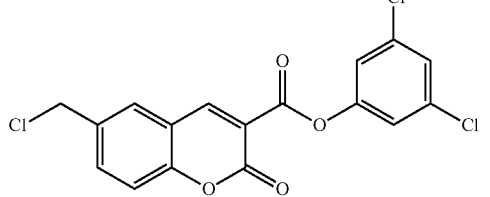 | LP75 | 80 ± 8 | 0.136 ± 0.012 | NI |
| 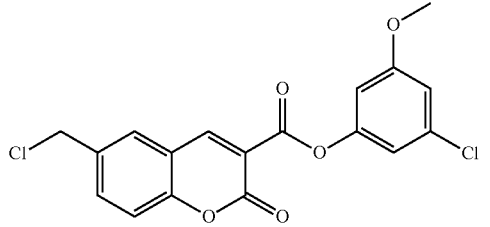 [SMILES: COc1cc(Cl)cc(OC(=O)c2cc3cc(CCl)ccc3oc2=O)c1] | LP61 | NI | 0.130 ± 0.005 | NI |
| 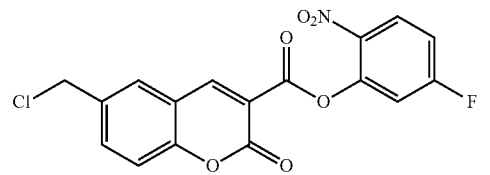 [SMILES: O=C(Oc1cc(F)ccc1[N+](=O)[O-])c1cc2cc(CCl)ccc2oc1=O] | CFL16 | 40% (100 μM) | 0.9 ± 0.4 | 73% (100 μM) |
| 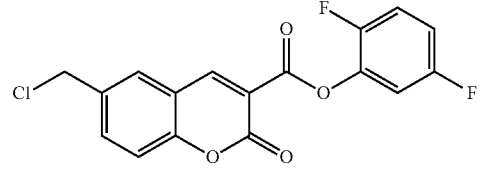 [SMILES: O=C(Oc1cc(F)ccc1F)c1cc2cc(CCl)ccc2oc1=O] | CFL5 | 35% (100 μM) | 0.50 ± 0.04 | 39 ± 4 |
| 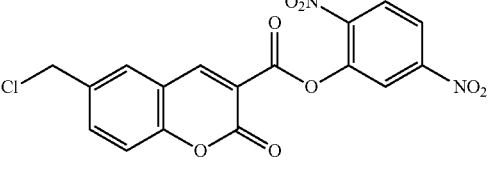 | CFL21 | [121 ± 5] | 22% (100 μM) | 43% (100 μM) |

TABLE A-continued

| molecule | name | IC$_{50}$ (μM) or % Inhibition | | |
|---|---|---|---|---|
| | | KLK5 | KLK7 | KLK14 |
| (structure) | CFL25 | 44 ± 10 | ND | 68 ± 9 |
| (structure) | CFL15 | 47% (100 μM) | 0.352 ± 0.055 | 45% (100 μM) |
| (structure) | CFL7 | NI | 33% (100 μM) | 33% (100 μM) |
| (structure) | MFS35 | NI | 55% (100 μM) | 71% (100 μM) |
| (structure) | IK8 | ≈40 | 64.3 ± 2.7 | 64% (100 μM) |
| (structure) | IK10 | 23% (50 μM) | NI | NI |
| (structure) | IK9 | 22% (50 μM) | NI | NI |
| (structure) | CFL4 | NI | 5.01 ± 0.4 | 60% (50 μM) |

TABLE A-continued
| molecule | name | IC$_{50}$ (μM) or % Inhibition | | |
|---|---|---|---|---|
| | | KLK5 | KLK7 | KLK14 |
| 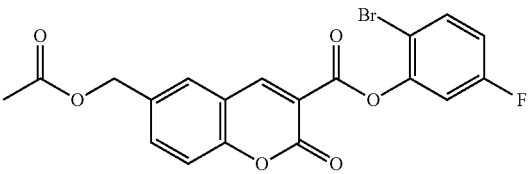 [SMILES: CC(=O)OCc1ccc2oc(=O)c(C(=O)Oc3cc(F)ccc3Br)cc2c1] | CFL17 | NI | 33% (100 μM) | 50% (50 μM) |
| 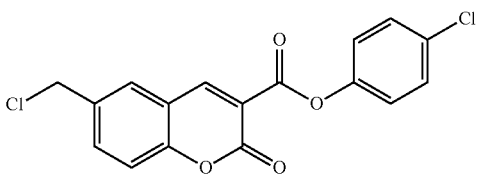 [SMILES: O=C(Oc1ccc(Cl)cc1)c1cc2cc(CCl)ccc2oc1=O] | LP7 | NI | 0.463 ± 0.007 | NI |
| 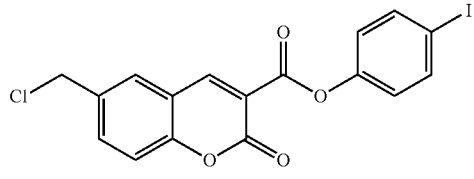 [SMILES: O=C(Oc1ccc(I)cc1)c1cc2cc(CCl)ccc2oc1=O] | LP16 | NI | 47% (50 μM) | NI |
| 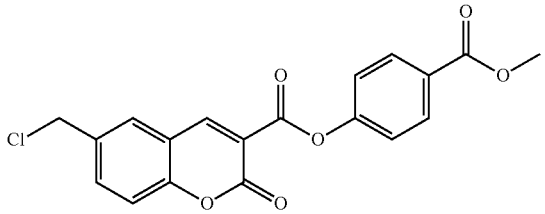 [SMILES: COC(=O)c1ccc(OC(=O)c2cc3cc(CCl)ccc3oc2=O)cc1] | IK13 | NI | 34% (100 μM) | 72% (100 μM) |
| 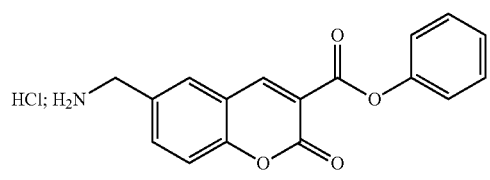 | LP71 | 182 ± 14 | NI | NI |
| 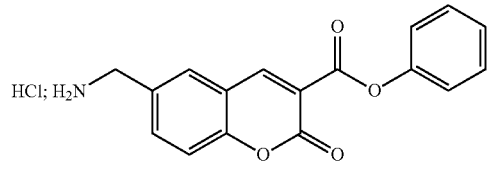 | LP18 | 78 ± 12 | 4.9 ± 0.3 | 30 ± 2 |
| 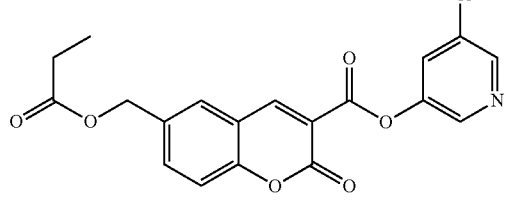 | LP42 | 22% (50 μM) | 52% (100 μM) | NI |

TABLE A-continued

| molecule | name | IC$_{50}$ (μM) or % Inhibition | | |
|---|---|---|---|---|
| | | KLK5 | KLK7 | KLK14 |
| (structure) | LP76 | 30% (50 μM) | 25% (50 μM) | 35% (50 μM) |
| (structure) | LP2 | NI | 0.128 ± 0.030 | NI |
| (structure) | D5 | 90% (100 μM) | 61% (100 μM) | 38% (100 μM) |
| (structure) | MFS2 | 54 ± 2 | 26.8 ± 1.5 | 73 ± 14 |
| (structure) | MFS3 | 39% (50 μM) | 20.9 ± 0.9 | 48% (100 μM) |
| (structure) | LP43 | 49% (100 μM) | 30% (100 μM) | 49% (100 μM) |
| (structure) | D9 | 80% (100 μM) | NI | 40% (100 μM) |
| (structure) | CFL33 | 7.0 ± 0.4 | NI | 61% (100 μM) |

TABLE A-continued

| molecule | name | IC$_{50}$ (μM) or % Inhibition | | |
|---|---|---|---|---|
| | | KLK5 | KLK7 | KLK14 |
| (structure) | LP41 | 32% (100 μM) | 0.39 ± 0.03 | 67% (100 μM) |
| (structure) | IK48 | 27% (50 μM) | 9.7 ± 1.3 | 32% (50 μM) |
| (structure) | MH30 | 25% (50 μM) | 33.2 ± 1.4 | 32% (50 μM) |
| (structure) | SMB27 | NI | 42% (50 μM) | 27% (50 μM) |
| (structure) | SMB26 | NI | 52% (10 μM) | NI |
| (structure) | SMB28 | NI | 82.2 ± 13.2 | NI |
| (structure) | IK53 | NI | 54% (10 μM) | NI |
| (structure) | MH52 | NI | 58% (10 μM) | NI |

TABLE A-continued
| molecule | name | IC$_{50}$ (μM) or % Inhibition | | |
|---|---|---|---|---|
| | | KLK5 | KLK7 | KLK14 |
| 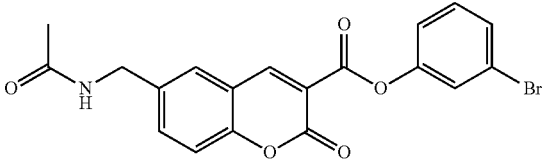 [SMILES: CC(=O)NCc1ccc2oc(=O)c(C(=O)Oc3cccc(Br)c3)cc2c1] | IK49 | NI | 54% (10 μM) | NI |
| 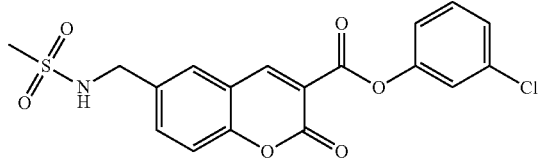 [SMILES: CS(=O)(=O)NCc1ccc2oc(=O)c(C(=O)Oc3cccc(Cl)c3)cc2c1] | MH24 | NI | 33.2 ± 1.4 | 42% (50 μM) |
| 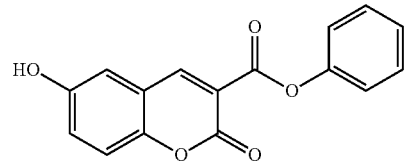 [SMILES: O=C(Oc1ccccc1)c1cc2cc(O)ccc2oc1=O] | MH8 | NI | 25% (50 μM) | NI |
| 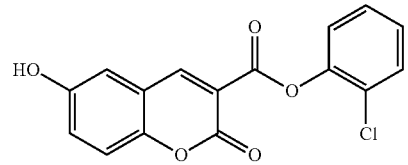 [SMILES: O=C(Oc1ccccc1Cl)c1cc2cc(O)ccc2oc1=O] | MH14 | NI | 35% (50 μM) | NI |
| 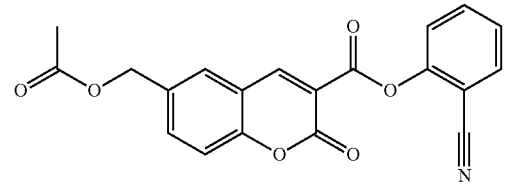 [SMILES: CC(=O)OCc1ccc2oc(=O)c(C(=O)Oc3ccccc3C#N)cc2c1] | SMB33 | NI | NI | 27% (50 μM) |
| 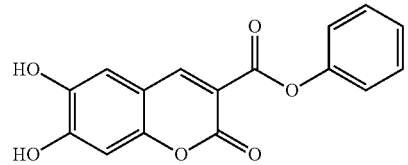 [SMILES: O=C(Oc1ccccc1)c1cc2cc(O)c(O)cc2oc1=O] | MH22 | 32% (50 μM) | 100% (50 μM) | 85% (50 μM) |
TABLE A2
| Compound | IC$_{50}$ (nM) or % d'inhibition | | |
|---|---|---|---|
| | KLK5 | KLK7 | KLK14 |
| 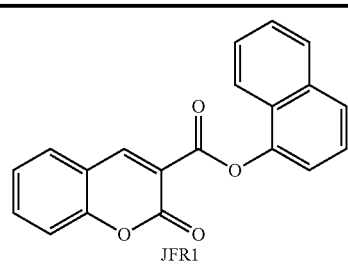 | ni | 53% (50 μM) | ni |

TABLE A2-continued
| Compound | IC$_{50}$ (nM) or % d'inhibition | | |
|---|---|---|---|
| | KLK5 | KLK7 | KLK14 |
| 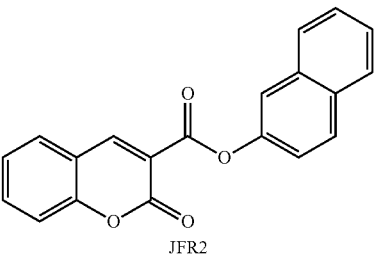 JFR2 | ni | 30% (50 µM) | ni |
| 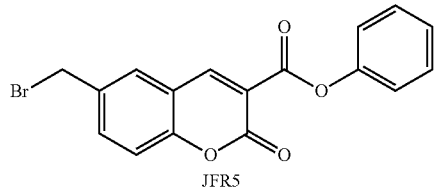 JFR5 | 34% (50 µM) | 249 ± 3.5 | 53% (50 µM) |
| 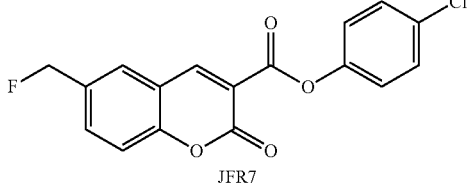 JFR7 | ni | 30% (50 µM) | ni |
| 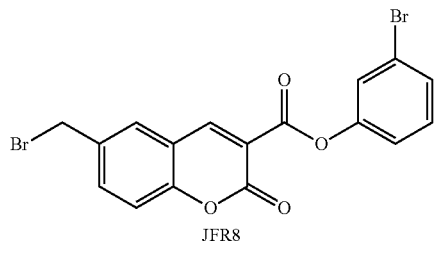 JFR8 | 1470 ± 60 | 57 ± 2 | 3000 ± 100 |
| 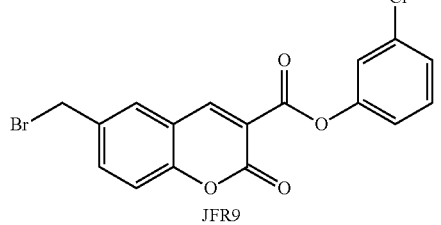 JFR9 | 920 ± 70 | 63.7 ± 1.7 | 2900 ± 100 |
| 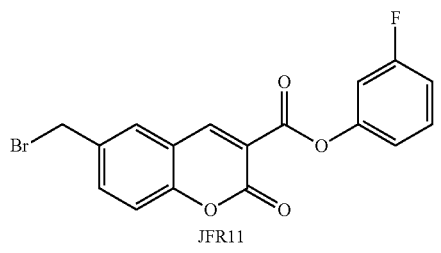 JFR11 | 42% (50 µM) | 198 ± 8 | 48% (50 µM) |

TABLE A2-continued

| | IC$_{50}$ (nM) or % d'inhibition | | |
|---|---|---|---|
| Compound | KLK5 | KLK7 | KLK14 |
| MFS33 (6-(chloromethyl)-2-oxo-2H-chromene-3-carboxylic acid pyridin-3-yl ester) | 62% (100 µM) | 5.7 ± 0.3 | 60% (100 µM) |

Examples of coumarin derivatives presenting a selective activity against KLK5, KLK7 and KLK14 are listed in Table B.

An acceptable threshold of inhibition corresponds for example to 30% at 100 µM.

TABLE B

| Enzyme | Molecule |
|---|---|
| KLK5 | LP71, CFL33, IK9, IK10, D9 |
| KLK7 | LP2, LP42, LP51, LP55, LP72, LP74, MFS7, CFL15, SMB26, SMB28, IK53, MH52, IK49, MH8, MH14, JFR1, JFR2, JFR7, LP14, LP8, IK2, MFS36, LP53, LP73, JFR9, JFR8 |
| KLK14 | MFS35, CFL21, CFL17, IK3, IK13, SMB33 |

Example 4

Cytotoxicity in Human Keratinocytes Using the Neutral Red Uptake (NRU) Cytotoxicity Test The NRU cytotoxicity assay procedure is a cell survival/viability chemosensitivity assay based on the ability of viable cells to incorporate and bind neutral red (NR), a supravital dye. NR is a weak cationic dye that readily penetrates cell membranes by non-ionic diffusion and accumulates intracellularly in lysosomes. Alterations of the cell surface or the sensitive lysosomal membrane lead to lysosomal fragility and other changes that gradually become irreversible. Such changes caused by the action of xenobiotics result in a decreased uptake and binding of NR. It is thus possible to distinguish between viable, damaged, or dead cells, which is the basis of this assay. After treatment with the small-molecules inhibitors, NR uptake in cells will be measured by spectrophotometry at 540±10 nm.

Day 0: Cell Preparation

Keratinocytes from healthy persons or patients with Netherton syndrome are seeded at the density of 4000 cells in 125 µL of medium per well in 96-well plates.

The culture medium is made of:
  half of complete Green medium: 60% (Dulbecco's Modified Eagle Media), 30% Ham's F12, 10% FCS, 180 mM adenin, 5 µg/mL insulin, 0.4 µg/mL hydrocortisone, 10 nM cholera toxin, 2 nM triiodothyronin, 10 ng/mL human recombinant EGF, 100 U/mL penicillin G/streptomycin.
  half of a basal medium (Epilife—Cascade Biologics) allowing keratinocytes culture without feeders.

2—Day 2: Cell Treatment

After seeding, cells are incubated for 48 hours in the following experimental conditions: 37° C.±1° C., 90%±5.0% humidity, and 5%±1% $CO_2$/air. This incubation period allows for cell recovery and adherence and progression to exponential growth phase.

Prepare inhibitors solutions 2-fold more concentrated than desired. Add 125 µL of these solutions to the wells without changing or removing the medium (125 µL).

A control with the vehicle alone (DMSO) is made.

A minimum of 3 wells per each experimental condition is done.

3—Day 4: NRU Measurement 48 h hours after the beginning of the treatment, carefully remove the medium (containing the tested inhibitor) and rinse the cells very carefully with 250 µL pre-warmed PBS.

Add 250 µL NR medium and incubate (37° C.±1° C., 90%±5% humidity, and 5.0%±1% $CO_2$/air) for 3±0.1 h. NR medium is the culture medium containing 33 µg/mL of NR. After incubation, remove the NR medium, and carefully rinse cells with 250 µL pre-warmed PBS.

Decant and blot PBS from the plate.

Add exactly 100 µL NR Desorb (50% ETOH/1% acetic acid) solution to all wells, including blanks.

Shake microtiter plate rapidly on a microtiter plate shaker for 20-45 min to extract NR from the cells and form a homogeneous solution. Plates should be protected from light by using a cover during shaking.

Plates should be still for at least five minutes after removal from the plate shaker.

Measure the absorption (within 60 minutes after adding NR Desorb solution) of the resulting colored solution at 540 nm±10 nm in a microtiter plate reader (spectrophotometer), using the blank as a reference.

4—Data Analysis

The experiments are performed three times on three different days for each inhibitor.

A calculation of cell viability expressed as NRU is made for each concentration of the tested inhibitor by using the mean NRU of the three replicate values per each concentration. This value is compared with the mean NRU of all vehicle values. Relative cell viability is then expressed as percent of untreated vehicle control (DMSO).

Example 5

Cell Viability

Normal human keratinocytes were seeded in a 96-well tissue culture plate. At 20% of confluence, molecules were added in the culture medium and incubated for 48 h. Neutral red medium was added to every well for an incubation period of 3 h, then the dye was extracted with acidified ethanol solution. Data (FIGS. 2 and 3) represent the mean cell viability after treatment+/−SD compared to mean viability of cells treated with the vehicle only (DMSO). Data represent the mean of 5 individual experiments.

No noticeable cytotoxicity on human normal keratinocytes was observed at 1 and 10 µM when assayed using the neutral red uptake test for LP7, LP14, LP41, LP53, LP55, LP61, LP73, LP76, MFS7, MFS33, CFL5, CFL33, IK2 and IK4.

No noticeable cytotoxicity on human normal keratmocytes was observed at 1 and 10 mM when assayed using the neutral red uptake test for JFR5, 8, 9 and 11 (FIG. 5).

Toxicity was observed for IK3 at 1 and 10 µM reaching 16.09±8.32% at 1 µM and 47.1±4.43% at 10 µM.

Example 6

Inhibitory Effect of Compounds of the Invention on the Expression of Pro-Allergic and Inflammatory Molecules in Netherton Syndrome Patient Keratinocytes 1—Cell Preparation:
250,000 keratinocytes from a Netherton syndrome patient (NSK) were seeded in 6 well plates in 2 mL of medium made of: (a) half of complete Green medium: (Dulbecco's Modified Eagle Media) 60%; Ham's F12 30%; FCS 10%; adenin 180 mM; insulin 5 µg/mL; hydrocortisone 0.4 µg/mL; cholera toxin 10 nM; triiodothyronin 2 nM; human recombinant EGF 10 ng/mL; penicillin G/streptomycin 100 U/mL; (b) half of a basal medium (Epilife—Cascade Biologics).

When confluent, cells were washed 5 times with PBS and 2 mL of complete Green medium without FCS (fetal calf serum) were added per well.
2—Treatment of Cells with Inhibitors:
Inhibitors were added in the culture medium 24 h after medium renewal.
3—Arrest of the Cell Culture and RNA Extraction 72 h after Beginning of the Treatment The supernatant was removed and cells were washed once with PBS.
350 µL of RLT lysis buffer (Mini Kit QIAGEN)+β-mercapto-ethanol (0.1%) were added per well to extract total RNA. The cell lysate was kept at −80° C. before RNA extraction (Mini Kit QIAGEN).
4—Measurement of KLK5 Activity Inhibition In this in cellulo test, KLK5 activity was evaluated by an indirect method. Indeed KLK5 induces TSLP (thymic stromal lymphopoietin), TNFα (tumor necrosis factor alpha) and IL-8 (interleukin 8) expression. If KLK5 activity is inhibited, the expression of these cytokines will be reduced.

The relative amount of TSLP, TNFα and IL-8 transcripts [relative to HPRT (hypoxanthine phosphoribosyltransferase 1) housekeeping gene] was compared between cells treated or not treated with the inhibitors. The ratio <<treated/not treated>> relative to housekeeping gene reflects KLK5 inhibition.

Two other genes showed increased expression in NSK i.e. MDC (macrophage derived cytokine or CCL22) and TARC (thymus and activation regulated chemokine or CCL17). Their expression had also been studied even if their mechanism of induction is not known yet.
5—Results The effect of LP73 and CFL33 on the expression of the described pro-allergic and inflammatory cytokines was analyzed on keratinocytes from two different NS patients. Each experiment was performed twice (FIG. 4).

LP73 at the dose of 1 µM significantly inhibited the expression of TSLP (p=0.0088), IL-8 (p=0.0269), TNFα (p=0.0004), MDC (p<0.0001) and TARC (p=0.0004) whereas at the dose of 10 µM, it only inhibited the expression of TSLP (p=0.002) and TARC (p=0.0461).

CFL33 at the dose of 1 µM significantly inhibited the expression of IL-8 (p=0.0309), MDC (p<0.0001) and TARC (p=0.0078) only.

Example 6bis

Study on a Mouse Model of Netherton Syndrome

JFR9 efficacy has been assayed on transgenic KLK5 mice skin section by in situ zymography (FIG. 6). These mice overexpress KLK5 and reproduce the phenotypic characteristics of Netherton syndrome. It has been shown that JFR9 molecule (5 µM) decreased significantly the total protease activity of the transgenic KLK5 mice skin section.

Example 7

Evaluation of the Efficacy of Coumarin Derivatives of the Invention on Psoriasis, Atopic Eczema and Allergic Contact Dermatitis Skin Pathologies To analyze whether coumarin derivatives have an efficacy on psoriasis, atopic eczema and allergic contact dermatitis skin pathologies, in situ zymographies on skin sections can be performed. The total protease activity can be visualized, as well as specific KLK5 and KLK7 activities directly in the tissue.

In situ zymography allows the study of protease activity in tissue. Skin sections of lesional skin are incubated in the presence, or not, of the tested compound and incubated 0/N with a specific substrate coupled to a fluorochrome (casein can be used as substrate to assess total protease activity or KLK5 and KLK7 specific substrates can be used to evaluate KLK5 and KLK7 activities. When the substrate is cleaved, the fluorochrome is released. The inhibition of the fluorochrome release is then analysed and quantified by confocal microscopy analysis.

The protocol is the following: frozen sections of lesional skin (5-µm thickness) are rinsed with a washing solution (2% Tween 20 in PBS, 2 min, followed by 5 min in PBS) and incubated or not with the tested compound and incubated at 37° C. overnight with 100 µl of BODIPY FL casein (10 µg/ml) using the EnzChek Ultra Protease Assay kit (Invitrogen) in 100 mM Tris-Cl, pH 8, in order to visualize global protease activity.

To assess KLK5 and KLK7 activities, cryostat sections after incubation or not with the tested compound, are incubated in the same conditions with 100 µl of Boc-Val-Pro-Arg-AMC or Suc-Leu-Leu-Val-Tyr-AMC (Sigma-Aldrich) at 100 µM and 40 µM respectively in Tris 50 mM, CaCl2 10 mM for the detection of trypsin-(KLK5) and chymotrypsin-like (KLK7) activity, respectively.

After incubation overnight at 37° C. with the substrate, sections are rinsed with PBS solution and visualized with the Axiovert 200 inverted high-end microscope (Zeiss) for KLK5 and KLK7 activities and Leica TCS SP5 AOBS for global protease activity. Images are analyzed with Image J software.

Should the coumarin derivatives inhibit KLK5 and KLK7 activities, a decrease of the release of the fluorochrome will be observed.

The invention claimed is:
1. A method for the treatment of a pathology involving an excess of activity of at least one member of the kallikrein family, comprising administering to a patient in need thereof a composition comprising an effective amount of a compound selected from the group consisting of:

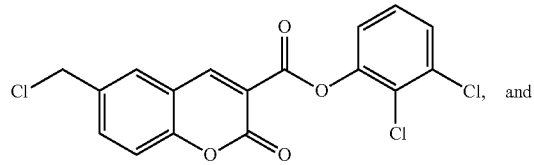
(LP73)

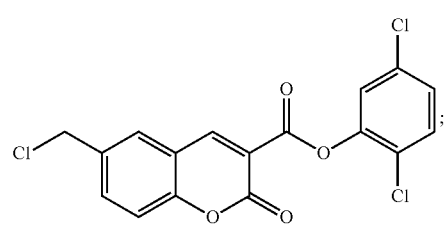
(LP74)

said at least one member of the kallikrein family being selected from the group consisting of kallikrein-5 and kallikrein-7;

said pathology being selected from the group consisting of Netherton syndrome, psoriasis, atopic eczema and allergic contact dermatitis.

2. The method according to claim 1, wherein said compound is

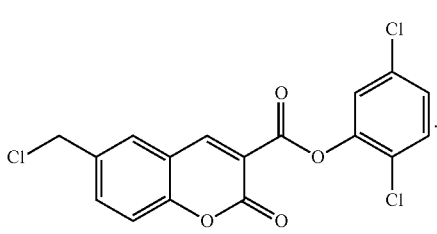
(LP74)

3. The method according to claim 1, wherein said compound is:

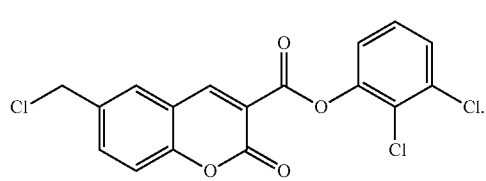
(LP73)

4. The method according to claim 1, wherein said pathology is Netherton syndrome.

* * * * *